United States Patent
Wu

(10) Patent No.: US 9,393,221 B2
(45) Date of Patent: Jul. 19, 2016

(54) METHODS AND COMPOUNDS FOR REDUCING INTRACELLULAR LIPID STORAGE

(75) Inventor: Sean Wu, Brookline, MA (US)

(73) Assignee: THE GENERAL HOSPITAL CORPORATION, Boston, MA (US)

( * ) Notice: Subject to any disclaimer, the term of this patent is extended or adjusted under 35 U.S.C. 154(b) by 748 days.

(21) Appl. No.: 13/552,975

(22) Filed: Jul. 19, 2012

(65) Prior Publication Data

US 2013/0023488 A1  Jan. 24, 2013

Related U.S. Application Data

(60) Provisional application No. 61/509,890, filed on Jul. 20, 2011.

(51) Int. Cl.

| | |
|---|---|
| C12N 5/00 | (2006.01) |
| C12N 5/02 | (2006.01) |
| A61K 31/137 | (2006.01) |
| A61K 31/215 | (2006.01) |
| A61K 31/4375 | (2006.01) |
| A61K 31/439 | (2006.01) |
| A61K 31/4458 | (2006.01) |
| A61K 31/4709 | (2006.01) |
| A61K 31/706 | (2006.01) |
| C40B 30/06 | (2006.01) |
| G01N 33/50 | (2006.01) |
| G01N 33/92 | (2006.01) |

(52) U.S. Cl.
CPC ............. *A61K 31/137* (2013.01); *A61K 31/215* (2013.01); *A61K 31/439* (2013.01); *A61K 31/4375* (2013.01); *A61K 31/4458* (2013.01); *A61K 31/4709* (2013.01); *A61K 31/706* (2013.01); *C40B 30/06* (2013.01); *G01N 33/5061* (2013.01); *G01N 33/5073* (2013.01); *G01N 33/92* (2013.01)

(58) Field of Classification Search
None
See application file for complete search history.

(56) References Cited

U.S. PATENT DOCUMENTS

| 7,449,482 B2 | 11/2008 | Cheng et al. |
| 7,855,289 B2 | 12/2010 | Nunes et al. |
| 2001/0048980 A1 | 12/2001 | Kishimoto et al. |
| 2007/0275997 A1 | 11/2007 | Frenneaux |
| 2009/0324682 A1 | 12/2009 | Popowski |
| 2011/0048980 A1 | 3/2011 | Seman |

FOREIGN PATENT DOCUMENTS

WO  WO2007096251  8/2007

OTHER PUBLICATIONS

Onyesom and Agho, Asian J. Sci. Res., Oct. 2010, vol. 4, No. 1, p. 78-83.*
Davis et al., Br J Clin Pharmacol., 1996, vol. 4, p. 415-421.*
Schweiger et al., Am J Physiol Endocrinol Metab, 2009, vol. 279, E289-E296.*
Maryam Ahmadian et al., Desnutrin/ATGL is regulated by AMPK and is required for a brown adipose phenotype, Cell Metabolism, vol. 13, pp. 739-748, 2011.
Mohammadreza Bozorgmanesh et al., Diabetes prediction, lipid accumulation product, and adiposity measures; 6-year follow-up: Tehran lipid and glucose study, Lipids in Health and Disease, vol. 9, pp. 1-9, 2010.
Judith Fischer et al., The gene encoding adipose triglyceride lipase (PNPLA2) is mutated in neutral lipid storage disease with myopathy, Nature Genetics, vol. 39, pp. 28-30, 2007.
Astrid Gruber et al., The N-terminal region of comparative gene identification-58 (CGI-58) is important for lipid droplet binding and activation of adipose triglyceride lipase, vol. 285, pp. 12289-12298, 2010.
Ken-Ichi Hirano et al., Triglyceride deposit cardiomyovasculopathy, The New England Journal of Medicine, vol. 359, pp. 2396-2398, 2008.
John D. Horowitz et al., Perhexiline and hypertrophic cardiomyopathy: A new horizon for metabolic modulation, Circulation, vol. 122, pp. 1547-1549, 2010.
Sally Inglis et al., Metabolic therapeutics in angina pectoris: history revisited with perhexiline, European Journal of Cardiovascular Nursing, vol. 5, pp. 175-184, 2006.
Kunihisa Kobayashi et al., The lack of the C-terminal domain of adipose triglyceride lipase causes neutral lipid storage disease through impaired interactions with lipid droplets, The Journal of Clinical Endocrinology and Metabolism, vol. 93, pp. 2877-2884, 2008.
Leong Lee et al., Metabolic modulation with perhexiline in chronic heart failure: A randomized, controlled trial of short-term use of a novel treatment, Circulation, vol. 112, pp. 3280-3288, 2005.
Krishnakant G. Soni et al., Coatomer-dependent protein delivery to lipid droplets, Journal of Cell Science, vol. 122, pp. 1834-1841, 2009.
John R. Ussher et al., Targeting malonyl CoA inhibition of mitochondrial fatty acid uptake acid uptake,as an approach to treat cardiac ischemia/reperfusion, Basic Research in Cardiology, vol. 104, pp. 203-210, 2009.

* cited by examiner

*Primary Examiner* — Kade Ariani
(74) *Attorney, Agent, or Firm* — Nixon Peabody LLP

(57) ABSTRACT

Compounds and compositions for reducing intracellular lipid accumulation in a cell are described herein. These compounds are useful for the treatment and prevention of lipid/glycogen disorders, as well as for the treatment and prevention of obesity. A high throughput screen for identifying compounds that reduce intracellular lipid accumulation in cells is also provided.

9 Claims, 15 Drawing Sheets

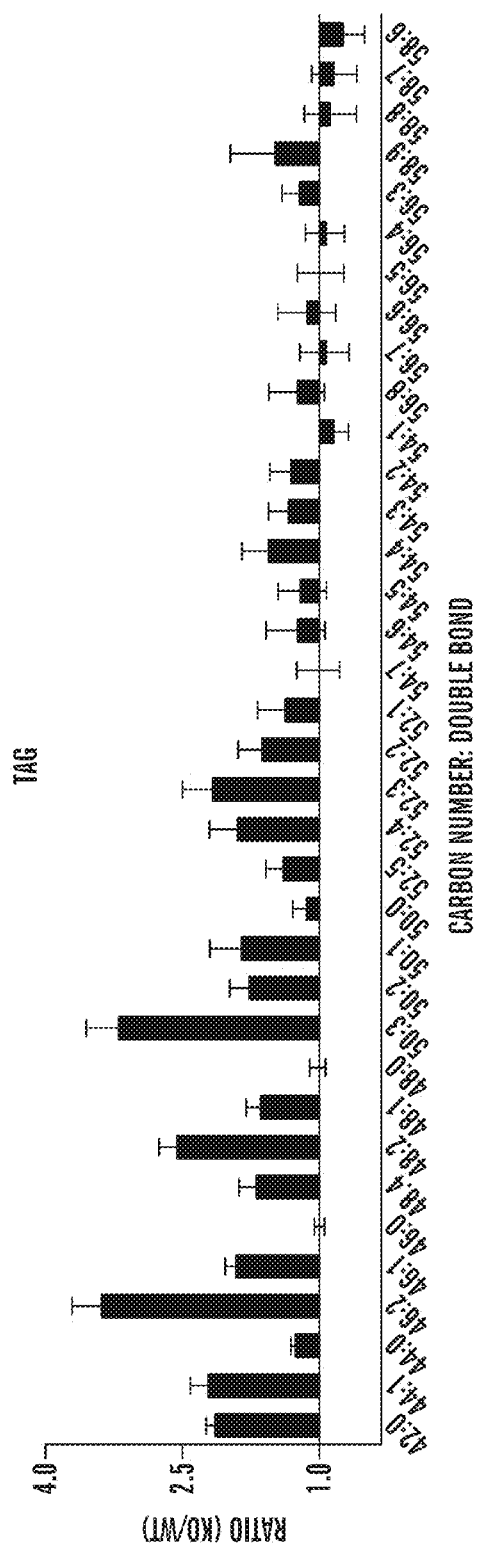
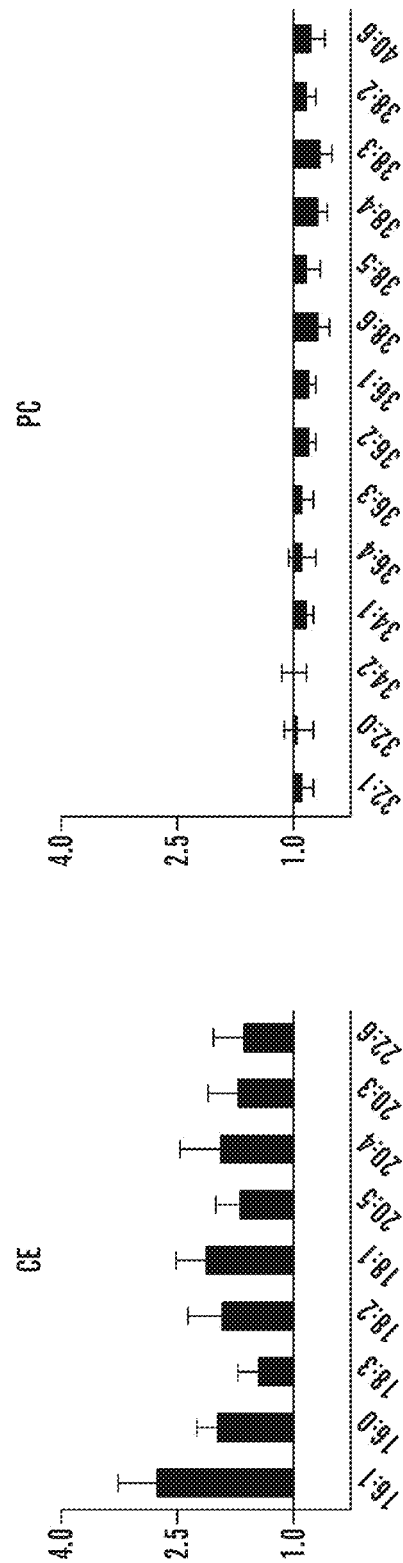
FIG. 4A
FIG. 4B
FIG. 4C

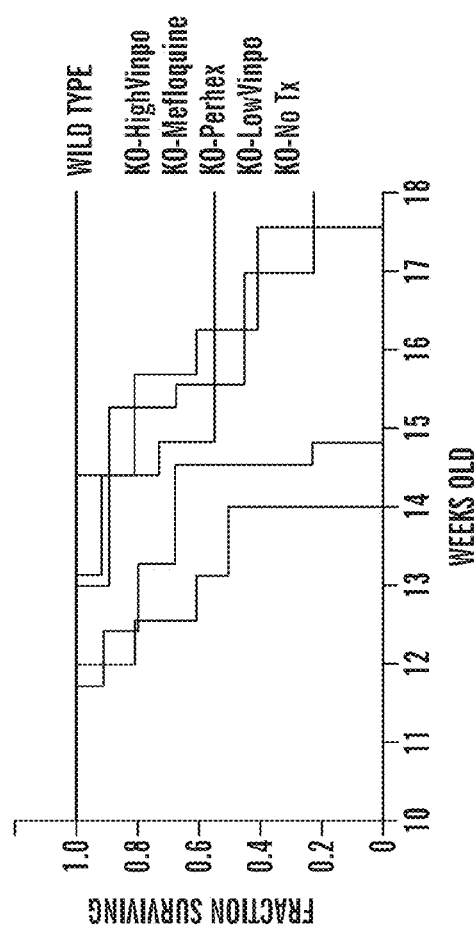
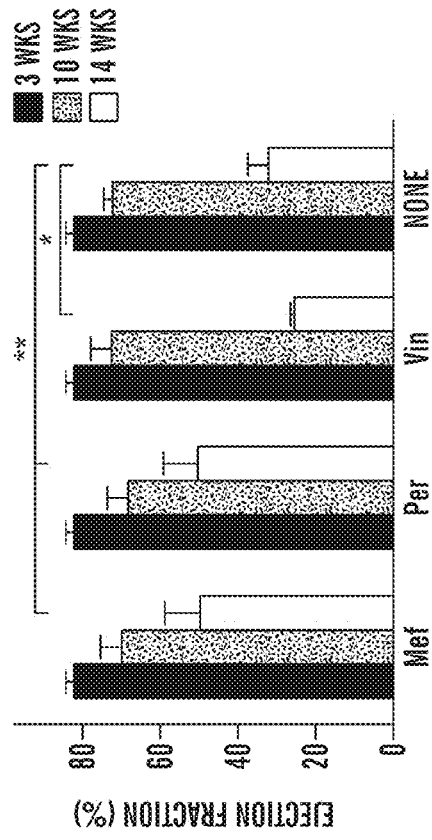
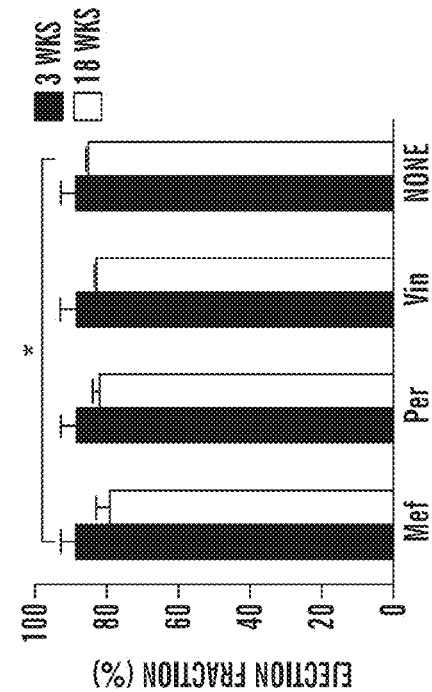
FIG. 8A
FIG. 8B
FIG. 8C

METHODS AND COMPOUNDS FOR REDUCING INTRACELLULAR LIPID STORAGE

CROSS-REFERENCE TO RELATED APPLICATIONS

This application claims the benefit under 35 U.S.C §119(e) of U.S. Provisional Application No. 61/509,890, filed Jul. 20, 2011, which is herein incorporated by reference in its entirety.

SEQUENCE LISTING

The instant application contains a Sequence Listing which has been submitted in ASCII format via EFS-Web and is hereby incorporated by reference in its entirety. Said ASCII copy, created on Jul. 25, 2012, is named 071061US.txt and is 12,530 bytes in size.

FIELD OF INVENTION

The invention relates to methods, compounds and compositions for the treatment of lipid/glycogen storage disorders and obesity.

BACKGROUND

Metabolic disorders, such as lipid storage disease and glycogen storage disease, can have devastating effects on patients. The Lipid storage diseases represent a group of disorders in which harmful amounts of lipids accumulate in various cells and tissues in the body. Glycogen storage disease is the result of defects in the processing of glycogen synthesis or breakdown within cells. Individuals with lipid/glycogen storage disorders either do not produce enough of one of the enzymes needed to break down (metabolize) lipids, or glycogen, or they produce enzymes that do not work properly. Over time, this excessive storage of fats and glycogen can cause permanent cellular and tissue damage, for example, in the heart, muscle, brain, peripheral nervous system, liver, spleen, and bone marrow.

Neutral lipid storage disease myopathy subtype (NLSD-M) is caused by loss-of-function mutations in PNPLA2, which encodes adipose triglyceride lipase (ATGL, also known as desnutrin) (Fischer et al., 2007). ATGL is expressed in a variety of tissues, including cardiac and skeletal muscle (Lake et al., 2005; Pinent et al., 2008), and as it cleaves the first ester bond in triacylglycerol (TAG), it is the rate-limiting enzyme in the breakdown of intracellular TAG droplets to provide free fatty acid for cellular energy metabolism (Haemmerle et al., 2006). Consistent with this function, the dominant phenotype of NLSD-M is excessive intracellular TAG accumulation in multiple tissues, notably in cardiac and skeletal muscle, which then go on to develop myopathy (Fischer et al. 2007; Kobayashi, K. et al., 2008). ATGL-knockout (ATGL-KO) mice exhibit an NLSD-M-like phenotype and suffer from fatal cardiac myopathy secondary to massive fat accumulation in the heart (Haemmerle et al., 2006).

Currently there is a lack of specific treatments available for most of the lipid/glycogen storage disorders and restricting one's diet does not prevent lipid/glycogen buildup in cells and tissues. Enzyme replacement therapy is available for some, e.g. patients with type 1 and type 3 Gaucher disease. However, most available treatments for storage disorders are preventative of secondary symptoms. For example, individuals having lipid storage disease associated with anemia may require blood transfusions and, in some patients, an enlarged spleen must be removed to improve cardiopulmonary function. For patients with Fabry disease, the drugs phenyloin and carbamazepine may be prescribed to help treat pain (including bone pain).

Given the lack of specific therapies for lipid/glycogen storage diseases, there is need in the art for compositions and methods for treatment of these disorders.

SUMMARY

Embodiments of the present invention are based, in part, on the establishment of a high throughput assay for the identification of compounds capable of modulating intracellular lipid storage. The inventors have generated both a murine and human induced pluripotent stem cell (iPSC) model system of neutral lipid storage disease, myopathy subtype (NLSD-M), a condition characterized by aberrant lipid accumulation in cardiac and skeletal muscle that results from the loss of functional adipose triglyceride lipase (ATGL). They demonstrate that differentiated ATGL-knockout (KO) iPSCs and human mutant iPSCs exhibit significantly increased lipid accumulation compared to differentiated control iPSCs, and using a high throughput platform for iPSC differentiation and small molecule screening have identified compounds that reduce lipid accumulation within both mouse and human NLSD-M iPSCs and extended the mean life span of ATGK knock out mice by 30% (from 13 to 17 weeks). They have also determined that inhibitors of intracellular lipid storage shift cellular energy metabolism from fatty acid oxidation to glycolysis. Thus, compounds selected using the high throughput screen are useful for the treatment and prevention of a variety of lipid/glycogen storage disorders, as well are useful for the treatment of obesity.

Accordingly, in one aspect, the invention provides for a method of reducing intracellular lipid accumulation in a cell comprising a contacting the cell with an effective amount of a compound selected from Table 1. In one embodiment, the compound is selected from a compound listed in Table 2. In one embodiment the compound is selected from a compound listed in Table 3. In one embodiment, the compound shifts cellular energy metabolism from fatty acid oxidation to glycolysis.

Intracellular lipid accumulation may be reduced in any cell type. In one embodiment the cell is selected from the group consisting of, a skeletal muscle cell, a heart muscle cell, a smooth muscle cell, a neuronal cell, a leukocyte cell, a bone marrow cell, an epithelial cell, and an endothelial cell.

In one embodiment, the cells to be contacted do not express functional adipose triglyceride lipase (ATGL), expresses only partially functional ATGL, or expresses a mutant form of ATGL. In one embodiment, the cell comprises a loss of function mutation in the gene PNPLA2 or lacks the gene PNPLA2.

The compounds may further comprise a pharmaceutically acceptable carrier and the cells may be contacted with the compound either in vitro or in vivo (e.g. in a subject in need of reduction of pathological intracellular lipid accumulation).

In one embodiment, the In vivo contact comprises administering a therapeutically effective amount of the compound to a subject using a administration route selected from the group consisting of: oral, subcutaneous, intravenous, intramuscular, intraperitoneal, intranasal, and topical. In one embodiment, the in vivo contact comprises administering the compound locally to the heart. In one embodiment the subject is a mammal, e.g. human. In one embodiment, the human subject is selected as being obese, or selected for being at risk of being obese. In one embodiment, the human subject is selected for treatment of a lipid/glycogen storage disorder.

In one embodiment, the lipid/glycogen storage disorder is characterized by increased intracellular lipid accumulation as compared to a normal healthy individual. In one embodiment, the lipid/glycogen storage disorder is associated with myopathy, e.g. neutral lipid storage disease (NLSD) or neutral lipid storage disease with myopathy (NLSD-M).

In some embodiments, the lipid/glycogen storage disorder is selected from the group consisting of: Activator Deficiency/GM2 Gangliosidosis, Alpha-mannosidosis, Aspartylglucosaminuria, Cholesteryl ester storage disease, Chronic Hexosaminidase A Deficiency, Cystinosis, Danon disease, Fabry disease, Farber disease, Fucosidosis, Galactosialidosis, Gaucher Disease, GM1 gangliosidosis, I-Cell disease/Mucolipidosis II, Infantile Free Sialic Acid Storage Disease/ISSD, Juvenile Hexosaminidase A Deficiency, Krabbe disease, Lysosomal acid lipase deficiency, Metachromatic Leukodystrophy, a Mucopolysaccharidoses disorder, Multiple sulfatase deficiency, Niemann-Pick Disease, a Neuronal Ceroid Lipofuscinoses, Pompe disease/Glycogen storage disease type II, Hypertrophic cardiomyopathy, Pycnodysostosis, Sandhoff disease/GM2 Gangliosidosis, Schindler disease, Salla disease/Sialic Acid Storage Disease, Tay-Sachs/GM2 gangliosidosis, and Wolman disease.

In one embodiment, the compound is Perhexyline, Fendiline hydrochloride, Vinpocetine, Mefloquine hydrochloride, Dicyclomine hydrochloride, Tomatine, or Clidinium bromide.

In another aspect of the invention, a high throughput assay for screening of compounds or agents that reduce intracellular accumulation of lipid within cells is provided. The assay comprising: (a) contacting a test population of induced pluripotent stem cells (iPSC's) derived from a somatic that lacks expression of functional adipose triglyceride lipase (ATGL), or that comprises a mutation in PNPLA2 gene, with a test compound; (b) differentiating the cells of step (a) in the presence of the test compound; and (c) selecting a compound that decreases lipid accumulation within the cells as compared to a differentiated control population of induced pluripotent stem cells (iPSC's) that has not been contacted with a test compound.

In one embodiment, the control population of cells is derived from the same somatic cell as the test population.

In one embodiment, the somatic cell is from a subject that has neutral lipid storage disease with myopathy (NLSD-M).

In one embodiment, the somatic cell is from an knock out animal that has had the gene for adipose triglyceride lipase (ATGL) deleted from its genome, or is a cell with a mutation in the gene for ATGL, wherein the gene for adipose triglyceride lipase (ATGL) is PNPLA2.

In one embodiment, the iPSC is differentiated into a cell selected from the group consisting of, a cardiac myocyte, a smooth muscle cell, and a skeletal muscle cell.

In one embodiment, lipid accumulation is determined by the use of Oil Red O (ORO) staining.

In one embodiment, the test compound or agent is selected from the group consisting of a small molecule, a nucleic acid, a protein, a peptide, an antibody, and antibody-fragment.

In one embodiment, the test compound or agent has a concentration in the range of 0.1 nM to 1000 mM.

In one embodiment, the test compound decreases lipid accumulation by at least 5%, 10%, 20%, 30%, 40%, 50%, 50%, 70%, 80%, 90%, 1-fold, 1.1-fold, 1.5-fold, 2-fold, 3-fold, 4-fold, 5-fold, 10-fold, 50-fold, 100-fold or more relative to the control.

Another aspect of the invention provides a method for treating or preventing a lipid/glycogen disorder comprising administrating a therapeutically effective amount of recombinant ATGL protein to a subject in need thereof.

Still another aspect of the invention provides a method for treating or preventing of obesity comprising administrating a therapeutically effective amount of recombinant ATGL protein to a subject in need thereof.

BRIEF DESCRIPTION OF THE DRAWINGS

FIG. 2a depicts Oct4 expression. FIG. 2b depicts Nestin expression. FIG. 2c depicts FoxA2 expression. FIG. 2d depicts Mlc2v expression. FIG. 2e depicts Brachury expression.

FIGS. 4a-4d depict bar graphs showing comprehensive profiling of changes in lipid species in ATGL¬KO vs. WT iPSCs a measured by mass spectrometry. The amounts of individual (FIG. 4a) triacylglycerol (TAG), (FIG. 4b) cholesterol ester (CE), and (FIG. 4c) phosphatidylcholine (PC) species were quantified in day 12 differentiated ATGL-KO and WT iPSCs plotted as ratios of KO levels over WT levels. The molecular species are denoted by their total acyl carbon number and total double bond number (total acyl carbon: total unsaturated bonds). (FIG. 4d) The ratio of aggregate levels of TAG, CE, diacylglycerols (DAG), phosphatidylethanolamines (PE), sphingomyelins (SM), lysophosphatidylcholines (LPC), lysophosphatidylethanolamines (LPE), and PC in KO vs. WT cells. Data are plotted as mean±standard error, n=6.

(FIG. 5a) A schematic of the screening protocol. (FIG. 5b) Graphic summary of screening results plotted as Z-score values for each compound. Negative scores indicate a decrease in ORO uptake compared to DMSO-treated cells. Inset shows the functional classification of the top 50 hits. (FIG. 5c) Compound set enrichment analysis, showing graphic depiction of enrichment of glycolytic switch inducers among the top hits (most negative Z-scores). The red-blue bar depicts the ranked list of analyzed compounds. Each vertical line shows the position of a glycolytic switch compound in the rank list. The blue rectangle indicates the region of greatest enrichment of glycolytic switch compounds among the top-scoring compounds from the ORO screen (i.e. 9 out of the top 50 and 5 out of the top 10 are potential glycolytic switch compounds). See also FIG. 6 for secondary validation of 7 of the top hits representing different functional classes.

(FIG. 6a) show bar graphs for relative ORO uptake for Fendiline, Vinpocetine, Dicyclomine, Clidinium, Perhexyline, Methoquine, and Tomatine respectively. ATGL-KO iPSCs were treated with low (5 nM) and high (3-75 M) doses of selected compounds from days 1 to 6 of differentiation in a monolayer, 96-well plate format. Data are plotted as the mean (n=12) normalized ORO levels relative to the ORO levels of DMSO-treated ATGL-KO iPSCs (set to 1.0) and WT iPSCs (set to 0.0) differentiated in parallel with the drug-treated KO cells. (FIG. 6b) is a bar graph of relative ORO uptake in KO iPSCs (x-axis) after treatment from days 7-12 of differentiation with the compounds (y-axis). Data are plotted as means (n=3) relative to the levels in untreated KO cells WT cells, as in (a) ($*P<0.05$, student's t-test when compared to DMSO-treated KO cells). (FIG. 6c) RT-PCR for cTnT, FoxA2, and Nestin in ATGL-KO iPSCs treated with compounds fendiline (F), vinpocetin, (V), dicyclomine (D), tomatine (T), mefloquine (M), and DMSO(S) from days 1-7 (D7) or days 7-12 (D12) of differentiation. Undifferentiated (D0) and differentiated but untreated WT (W) and KO (K) iPSCs served as controls. H=no template control.

FIGS. 8a-8f show graphs of the in vivo validation of the drug hit efficacy on ATGL-KO mice. (FIG. 8a) Kaplan-Meier survival plot of ATGL-KO mice treated with Mefloquine (N=15), Perhexyline (N=15), Vinpocetin low dose (N=15), Vinpocetin high dose (N=15), or water alone (N=15) (FIG. 8b) Contractile function of wild type mice treated with Mefloquine (Mef), Perhexyline (Per), Vinpocetin (Vin), and water (None) at 3 weeks of age before drug treatment (black) and at 18 weeks of age (white) after drug treatment. (FIG. 8c) Contractile function of ATGL-KO mice treated with Mef, Per, Vin, and water at 3 weeks of age before drug treatment (black) and at 10 (gray), and 14 (white) weeks of age after drug treatment. (FIG. 8d) Measurement of triglyceride content in hearts of 14 weeks old wild type (WT) and ATGL-KO (KO) mice after treatment with the indicated drugs. V (H)—vinpocetin high dose, V (L)—vinpocetin low dose. (FIG. 8e) Measurement of triglyceride content in the liver, lung, and kidney of WT mice (gray) and ATGL-KO mice treated with Per (red), Mef (green), V (H) (blue), V (L) (orange), or water (black). (FIG. 8f) Quantitative PCR analysis of metabolic gene expression in the hearts of 14 weeks old ATGL-KO mice treated with water (black), Per (red), and Mef (green) and in the hearts of age-matched WT mice (gray).

(FIG. 9a) A genomic map of the homozygous mutation in exon 5 (LC1) and exon 7 (LC2) of two Japanese patients. (FIG. 9b) Determination of TG content in differentiated human iPSCs treated with Mef, Per, Vin, and WY14643, a PPAR-alpha agonist.

DETAILED DESCRIPTION

Figure 2A:
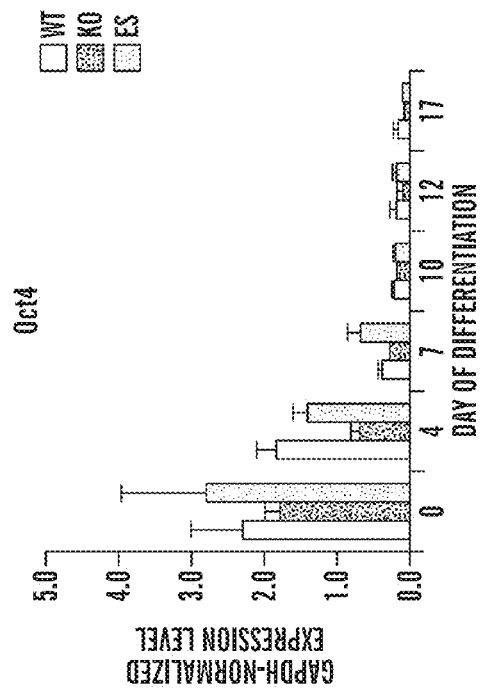
FIGS. 2a-2e depict bar graphs of quantitative PCR for the expression of embryonic germ layer markers during in vitro differentiation. ATGL-KO and WT iPSCs and control ES cells were differentiated as EBs and harvested at the indicated days to assess RNA expression levels of the indicated lineage markers. The expression level of each gene is normalized against the corresponding expression level of GAPDH in each sample. Data are displayed as mean±s.d. (n=3). *=not detected.
Figure 2B:
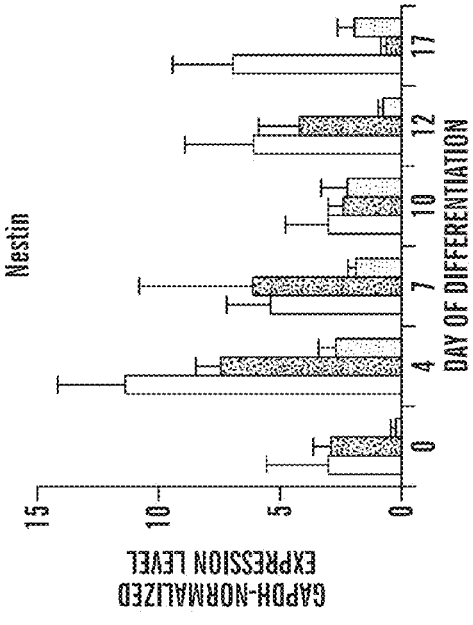

Embodiments of the invention provide methods and compositions for the reduction of lipid accumulation within cells, either in vitro or in vivo. The methods comprise contacting the cell, either in vitro or in vivo, with an effective amount of a compound described herein, e.g. a compound selected from Tables 1-3.

As used herein, the phrase "reducing intracellular lipid accumulation" refers to a decrease in lipid accumulation within cells as compared to a reference. In some embodiments, contacting of a cell with a compound described herein results in at least about 10%, at least about 20%, at least about 30%, at least about 40%, at least about 50% at least about 60%, at least about 70%, at least about 80%, at least about 90%, or at least about 95% reduction of lipid accumulation, or about 2-fold, about 3-fold, about 4-fold, about 5-fold or more decrease in lipid accumulation as compared to control not treated with the compound.

Intracellular lipid accumulation can be assessed by means well known to those of skill in the art, for example in vitro (e.g., tissue samples or cells) by using colorimetric lipid staining assays such as Oil Red O (ORO) staining of cells (e.g. tissue sample) as described herein, or by commercially available triglyceride assay kits, e.g. TG-1™ kits from Zen-Bio, Inc. Research Triangle Park, N.C. 27709. Triglyceride assay kits provide quantitative data on triglyceride accumulation in cultured or in primary cells (Whittaker, et al. *Journal of biomolecular screening*, 2010, 15: 798-805). ORO staining of cells and tissue samples is described in, e.g., Fischer et al. *Nature Genetics*, 2007, 39(1): 28-30; and Hirano et al. *N Engl J Med*, 2008, 359:2396-2398, which are herein incorporated by reference in their entirety.

Intracellular lipid accumulation can be assessed in vivo by assessing lipid deposition in a subject, e.g. by assessing the body mass index (BMI) or the "lipid accumulation product" (LAP) (Khan et al. *BMC Cardiovascular Disorders*, 2005, 5: 26). LAP is a simple index for estimating lipid overaccumulation among adults, designated the "lipid accumulation product" (LAP), based on a combination of two measurements: 1) waist circumference (WC), a measure of truncal fat that includes the visceral (intra-abdominal) depot and 2) the fasting concentration of circulating triglycerides (TGs) (Bozorgmanesh et al., Diabetes prediction, lipid accumulation product, and adiposity measures; 6-year follow-up: Tehran lipid and glucose study, *Lipids in Health and Disease*, 2010, 9:45).

Contacting of Cells with Compounds

Cells can be contacted with the compounds described herein in a cell culture e.g., in vitro or ex vivo, or administrated to a subject, e.g., in vivo. In some embodiments of the invention, a compound described herein is administrated to a subject to treat or prevent a lipid/glycogen storage disorder including. In some embodiments of the invention, a compound described herein is administered to treat or prevent obesity.

The term "contacting" or "contact" as used herein in connection with contacting a cell includes subjecting the cell to an appropriate culture media which comprises the indicated compound or agent. Where the cell is in vivo, "contacting" or "contact" includes administering the compound or agent in a pharmaceutical composition to a subject via an appropriate administration route such that the compound or agent contacts the cell in vivo.

For in vitro methods, cells can be obtained from different sources. For example, the contacted cell can be obtained from a subject, or the cell can be derived from a subject's embryonic stem cells (ESCs), or from a somatic cell, e.g. an induced pluripotent stem cell (undifferentiated or differentiated). In some embodiments, the subject is suffering from a lipid/glycogen storage disorder. In some embodiments, the subject is human. In some embodiments, the subject is mouse. In some embodiments, mouse is a transgenic mouse, e.g. a gene knock out mouse (KO), or mouse comprising a mutated lipid/glycogen storage disease gene.

For in vivo methods, a therapeutically effective amount of a compound described herein can be administered to a subject. Methods of administering compounds to a subject are known in the art and easily available to one of skill in the art.

As one of skill in the art is aware, reducing lipid accumulation within cells in a subject can lead to treatment, prevention or amelioration of a number of lipid/glycogen storage disorders. As used herein, a "lipid/glycogen storage disorder" refers to any disease or disorder caused by or associated with excess (pathological) accumulation of lipid, or glycogen, within cells of the body, wherein the lipid/glycogen storage disorder is not obesity. All types of cells within the body can be affected (e.g. smooth muscle, skeletal muscle, adipocytes, neuronal, epithelial cells, etc.). Representative examples lipid/glycogen storage disorders are described herein.

Reducing lipid accumulation within cells in a subject can also lead to treatment, prevention or amelioration, of obesity in a subject. As used herein, the term "obesity" is a condition in which an individual has an excess of body fat. Guidelines for determination of obesity in a subject are well established in the art, e.g. as determined by body mass index (BMI). The Body Mass Index (BMI) is calculated as body weight per height in meters squared ($kg/m^2$). "Obesity" refers to a condition whereby an otherwise healthy subject has a Body Mass Index (BMI) greater than or equal to 30 $kg/m^2$. An "obese subject" is an otherwise healthy subject with a Body Mass Index (BMI) greater than or equal to 30 $kg/m^2$ or is a subject with at least one co-morbidity with a BMI greater than or equal to 27 kg/m2. A "subject at risk of obesity" is an otherwise healthy subject with a BMI of 25 $kg/m^2$ to less than 30 $kg/m^2$. In one embodiment, obesity is characterized by central obesity (excessive fat tissue in and around the abdomen). Central obesity in males correlates to waist to hip ratio higher than 0.90; central obesity in females correlates to a waist to hip ratio higher than 0.85.

By "treating" a disorder (e.g. lipid/glycogen storage disorder or obesity) is meant reversing, alleviating, ameliorating, inhibiting, slowing down or stopping the progression, of the storage disorder, i.e. the severity of the storage disorder. By "preventing" a disorder (e.g. lipid/glycogen storage disorder or obesity) is meant delaying or preventing the onset of such a disorder (e.g. delaying or preventing the onset of pathological lipid deposition).

In one aspect, the invention described herein features a method for treating or preventing a lipid/glycogen storage disorder in a subject, the method comprising: administering a therapeutically effective amount of a compound to a subject in need of treatment, wherein the compound is selected from Table 1, Table 2, or Table 3, and wherein the compound reduces accumulation of lipids within cells.

In one embodiment, treatment of a lipid/glycogen storage disorder alleviates lipid accumulation within cells by at least 20%, at least 30%, at least 40%, or at least 50%, by at least 70%, by at least 80%, or by at least 90%, as measured by a reduction in the abnormal lipid accumulation within cells (e.g. as determined by ORO staining). In one embodiment, one or more symptoms of a lipid/glycogen storage disorder are alleviated by at least 20%, at least 30%, at least 40%, or at least 50%. In one embodiment, a symptom of a lipid/glycogen storage disorder is alleviated by more that 50%. In one embodiment, the symptom of a lipid/glycogen storage disorder is alleviated by 80%, 90%, or greater. In some embodiments, the symptoms of lipid/glycogen storage disorder improves by at least about 10%, 20%, 30%, 40%, 50%, 60%, 70% or more. Clinicians are well versed in determination of symptom alleviation.

In one embodiment, in lipid/glycogen disorders associated with myopathy, muscular function is improved by at least about 10%, 20%, 30%, 40%, 50%, 60%, 70% or more.

Examples of lipid/glycogen storage disorders include, but are not limited to: Activator Deficiency/GM2 Gangliosidosis, Alpha-mannosidosis, Aspartylglucosaminuria, Cholesteryl ester storage disease, Chronic Hexosaminidase A Deficiency, Cystinosis, Danon disease, Fabry disease, Farber disease, Fucosidosis, Galactosialidosis, Gaucher Disease (e.g. Type I, Type II, or Type III), GM1 gangliosidosis (e.g. Infantile, Late infantile/Juvenile, Adult/Chronic), I-Cell disease/Mucolipidosis II, Infantile Free Sialic Acid Storage Disease/ISSD, Juvenile Hexosaminidase A Deficiency, Krabbe disease (e.g. Infantile Onset, Late Onset) Lysosomal acid lipase deficiency (e.g. Early onset or Late onset), Metachromatic Leukodystrophy, a Mucopolysaccharidoses disorder (e.g. Pseudo-Hurler polydystrophy/Mucolipidosis IIIA, MPSI Hurler Syndrome, MPSI Scheie Syndrome, MPS I Hurler-Scheie Syndrome, MPS II Hunter syndrome, Sanfilippo syndrome Type A/MPS III A, Sanfilippo syndrome Type B/MPS III B, Sanfilippo syndrome Type C/MPS III C, Sanfilippo syndrome Type D/MPS III D, Morquio Type A/MPS IVA, Morquio Type B/MPS IVB, MPS IX Hyaluronidase Deficiency, MPS VI Maroteaux-Lamy, MPS VII Sly Syndrome, Mucolipidosis I/Sialidosis, Mucolipidosis IIIC, Mucolipidosis type IV), Multiple sulfatase deficiency, Niemann-Pick Disease (e.g. Type A, Type B, or Type C), a Neuronal Ceroid Lipofuscinoses disorder (e.g., CLN6 disease (e.g. Atypical Late Infantile, Late Onset variant, Early Juvenile), Batten-Spielmeyer-Vogt/Juvenile NCL/CLN3 disease, Finnish Variant Late Infantile CLN5, Jansky-Bielschowsky disease/Late infantile CLN2/TPP1 Disease, Kufs/Adult-onset NCL/CLN4 disease, Northern Epilepsy/variant late infantile CLN8, Santavuori-Haltia/Infantile CLN1/PPT disease, Beta-mannosidosis), Pompe disease/Glycogen storage disease type II, Hypertrophic cardiomyopathy (e.g. due to glycogen storage from AMPK-gamma2 or LAMP2 mutation), Pycnodysostosis, Sandhoff disease/Adult Onset/GM2 Gangliosidosis, Sandhoff disease/GM2 gangliosidosis-Infantile, Sandhoff disease/GM2 gangliosidosis, Juvenile, Schindler disease, Salla disease/Sialic Acid Storage Disease, Tay-Sachs/GM2 gangliosidosis, and Wolman disease.

Lipid/glycogen storage disorders are well known to those of skill in the art and described in e.g.: A clinical guide to inherited metabolic diseases by Joe T. R. Clarke, Cambridge University Press (2006); and in Inborn Metabolic Diseases: Diagnosis and Treatment, Springer Medzin Verieg (Germany), by John Fernandes, Jean-Marie Saudubray, and Georges Van Den Berghe 4$^{th}$ edition, 2008., which are herein incorporated by reference. A subset of lipid/glycogen storage disorders are described herein.

Lipid Storage Disorders

Lipid storage disorders are a group of metabolic disorders in which harmful amounts of lipids accumulate in various cells and tissues in the body and include, but are not limited to: Neutral lipid Storage disease, Gaucher disease, Niemann-Pick disease, Fabry disease, Farber's disease, GM1 and GM2 (e.g. Tay-Sachs disease, and Sandhoff disease) gangliosidoses, Krabbé disease, Metachromatic leukodystrophy, and Wolman's disease. Symptoms that can be alleviated and improved in a subject and the enzyme deficiencies associated with various lipid storage disorders are described in more detail below.

In one aspect of the invention, the compounds of the invention are used to treat or prevent a lipid storage disease. The method comprises administering a therapeutically effective amount of a compound selected from Table 1, from Table 2, or from Table 3, to a subject in need of treatment.

Neutral Lipid Storage Disease and Symptoms

In one embodiment the lipid storage disorder is Neutral lipid storage disease (NLSD) (also known as "Chanarin-Dorfman syndrome"). NLSD is an autosomal recessive disorder in which lipids are stored abnormally in organs and tissues throughout the body characterized by accumulation of triglycerides in the cytoplasm of leukocytes, muscle, liver, fibroblasts, and other tissue. NLSD. Individuals with NLSD suffer from cardiac and skeletal myopathy and hepatic steatosis due to the accumulation of fats in muscle tissue. Other features of NLSD include fatty liver, a weakened and enlarged heart (cardiomyopathy), inflammation of the pancreas (pancreatitis), and reduced thyroid activity (hypothyroidism). Mutations in adipocyte triglyceride lipase (ATGL) regulatory protein CGI-58 cause NLSD-I, with additional symptoms of neurological defects (Lefevre et al. Am. J. Hum. Genet. 2001). In one embodiment, the lipid storage disorder is neutral lipid storage disease with myopathy (NLSD-M). Mutations in the PNPLA2 gene cause NLSD-M, which is characterized by more severe myopathy than NLSD. The PNPLA2 gene encodes the enzyme adipose triglyceride lipase (ATGL), which plays a role in breaking triglycerides, the main source of stored energy in cells. PNPLA2 gene mutations impair the ATGL enzyme's ability to break down triglycerides, which then accumulate in muscle and tissues throughout the body, resulting in the signs and symptoms of neutral lipid storage disease with myopathy. Two out of six patients identified with NLSD-M die from heart failure (Fischer et al. Nat. Genet. 2007).

Gaucher Disease and Symptoms.

In one embodiment the lipid storage disorder is Gaucher disease. Gaucher disease is the most common of the lipid storage diseases and is caused by a deficiency of the enzyme glucocerebrosidase. Fatty material often collects in the spleen, liver, kidneys, lungs, brain, and bone marrow. Symptoms may include enlarged spleen and liver, liver malfunction, skeletal disorders and bone lesions that may cause pain and fractures, severe neurologic complications, swelling of lymph nodes and (occasionally) adjacent joints, distended abdomen, a brownish tint to the skin, anemia, low blood platelets, and yellow spots in the eyes. Persons affected most seriously may also be more susceptible to infection. The disease affects males and females equally.

Gaucher disease has three common clinical subtypes. Type 1 (or normeuropathic type) is the most common form of the disease. It occurs most often among persons of Ashkenazi Jewish heritage.

Symptoms of Gaucher disease may begin early in life or in adulthood and include enlarged liver and grossly enlarged spleen, which can rupture and cause additional complications. Skeletal weakness and bone disease may be extensive. The brain is not affected, but there may be lung and, rarely, kidney impairment. Patients in this group usually bruise easily due to low blood platelets and experience fatigue due to anemia. Depending on disease onset and severity, type 1 patients may live well into adulthood. Many patients have a mild form of the disease or may not show any symptoms. Type 2 (or acute infantile neuropathic Gaucher disease) typically begins within 3 months of birth. Symptoms include an enlarged liver and spleen, abnormal eye movement, extensive and progressive brain damage, spasticity, seizures, limb rigidity, and a poor ability to suck and swallow. Affected children usually die before age 2. Type 3 (the chronic neuronopathic form) can begin at any time in childhood or even in adulthood. It is characterized by slowly progressive but milder neurologic symptoms compared to the acute or Type 2 Gaucher disease. Major symptoms include an enlarged spleen and/or liver, seizures, poor coordination, skeletal irregularities, eye movement disorders, blood disorders including anemia, and respiratory problems. Patients often live to their early teen years and, in some cases, into adulthood.

In some embodiments, the compounds of the invention are administered in conjunction with additional therapies known to be effective in the disorder. For example, for type 1 and most type 3 Gaucher disease patients, enzyme replacement treatment can be given intravenously every two weeks and can dramatically decrease liver and spleen size, reduce skeletal abnormalities, and reverse other manifestations. Surgery to remove the spleen may be required on rare occasions (if the patient is anemic or when the enlarged organ affects the patient's comfort). Blood transfusion may benefit some anemic patients. Other patients may require joint replacement surgery to improve mobility and quality of life.

Niemann-Pick Disease and Symptoms

In one embodiment the lipid storage disorder is a Niemann-Pick disease. Niemann-Pick disease is a group of autosomal recessive disorders caused by an accumulation of fat and cholesterol in cells of the liver, spleen, bone marrow, lungs, and, in some patients, brain. Neurological complications may include ataxia, eye paralysis, brain degeneration, learning problems, spasticity, feeding and swallowing difficulties, slurred speech, loss of muscle tone, hypersensitivity to touch, and some corneal clouding. A characteristic cherry-red halo develops around the center of the retina in 50 percent of patients.

Niemann-Pick disease is currently subdivided into four categories. Onset of type A, the most severe form, is in early infancy. Infants appear normal at birth but develop an enlarged liver and spleen, swollen lymph nodes, nodes under the skin (xanthemas), and profound brain damage by 6 months of age. The spleen may enlarge to as much as 10 times its normal size and can rupture. These children become progressively weaker, lose motor function, may become anemic, and are susceptible to recurring infection. They rarely live beyond 18 months. This form of the disease occurs most often in Jewish families. In the second group, called type B (or juvenile onset), enlargement of the liver and spleen characteristically occurs in the pre-teen years. Most patients also develop ataxia, peripheral neuropathy, and pulmonary difficulties that progress with age, but the brain is generally not affected. Type B patients may live a comparatively long time but many require supplemental oxygen because of lung involvement. Niemann-Pick types A and B result from accumulation of the fatty substance called sphingomyelin, due to deficiency of an enzyme called sphingomyelinase.

Niemann-Pick disease also includes two other variant forms called types C and D. These may appear early in life or develop in the teen or even adult years. Niemann-Pick disease types C and D are not caused by a deficiency of sphlingomyelinase but by a lack of the NPC1 or NPC2 proteins. As a result, various lipids and particularly cholesterol accumulate inside nerve cells and cause them to malfunction. Patients with types C and D have only moderate enlargement of their spleens and livers. Brain involvement may be extensive, leading to inability to look up and down, difficulty in walking and swallowing, and progressive loss of vision and hearing. Type D patients typically develop neurologic symptoms later than those with type C and have a progressively slower rate of loss of nerve function. Most type D patients share a common ancestral background in Nova Scotia. The life expectancies of patients with types C and D vary considerably. Some patients die in childhood while others who appear to be less severely affected can live into adulthood. Children usually die from infection or progressive neurological loss.

In some embodiments of the invention, the compounds of the invention are administered in conjunction with additional therapies, e.g. patients with types C and D are frequently placed on a low-cholesterol diet and/or cholesterol lowering drugs, although research has not shown these interventions change the abnormal cholesterol metabolism or halt progression of the disease.

Fabry Disease and Symptoms

In one embodiment the lipid storage disorder is Fabry disease. Fabry disease, also known as alpha-galactosidase-A deficiency, causes a buildup of fatty material in the autonomic nervous system, eyes, kidneys, and cardiovascular system. Fabry disease is the only X-linked lipid storage disease. Males are primarily affected although a milder form is common in females. Occasionally, affected females have severe manifestations similar to those seen in males with the disorder. Onset of symptoms is usually during childhood or adolescence. Neurological signs include burning pain in the arms and legs, which worsens in hot weather or following exercise, and the buildup of excess material in the clear layers of the cornea (resulting in clouding but no change in vision). Fatty storage in blood vessel walls may impair circulation, putting the patient at risk for stroke or heart attack. Other manifestations include heart enlargement, progressive kidney impairment leading to renal failure, gastrointestinal difficulties, decreased sweating, and fever. Angiokeratomas (small, non-cancerous, reddish-purple elevated spots on the skin) may develop on the lower part of the trunk of the body and become more numerous with age. Patients with Fabry disease often die prematurely of complications from heart disease, renal failure, or stroke.

In some embodiments, the compounds are administered in conjunction with additional therapies, e.g. drugs such as phenyloin and carbamazepine are often prescribed to treat pain that accompanies Fabry disease and metoclopramaide or Lipisorb (a nutritional supplement) can ease gastrointestinal distress that often occurs in Fabry patients, and some individuals may require kidney transplant or dialysis. Enzyme replacement can reduce storage, ease pain, and improve organ function in patients with Fabry disease.

Farber's Disease and Symptoms

Farber's disease, also known as Farber's lipogranulomatosis, describes a group of rare autosomal recessive disorders that cause an accumulation of fatty material in the joints, tissues, and central nervous system. The disorder affects both males and females. Disease onset is typically in early infancy but may occur later in life. Children who have the classic form of Farber's disease develop neurological symptoms within the first few weeks of life. These symptoms may include moderately impaired mental ability and problems with swallowing. The liver, heart, and kidneys may also be affected. Other symptoms may include vomiting, arthritis, swollen lymph nodes, swollen joints, joint contractures (chronic shortening of muscles or tendons around joints), hoarseness, and xanthemas which thicken around joints as the disease progresses. Patients with breathing difficulty may require insertion of a breathing tube. Most children with the disease die by age 2, usually from lung disease. In one of the most severe forms of the disease, an enlarged liver and spleen (hepatosplenomegaly) can be diagnosed soon after birth. Children born with this form of the disease usually die within 6 months.

Farber's disease is caused by a deficiency of the enzyme called ceramidase. Currently there is no specific treatment for Farber's disease. Corticosteroids may be prescribed to relieve pain. Bone marrow transplants may improve granulomas (small masses of inflamed tissue) on patients with little or no lung or nervous system complications. Older patients may have granulomas surgically reduced or removed.

Gangliosidoses and Symptoms

In one embodiment the lipid storage disorder is a gangliosidose. The gangliosidoses are comprised of two distinct groups of genetic diseases. Both are autosomal recessive and affect males and females equally. The GM1 gangliosidoses are caused by a deficiency of the enzyme beta-galactosidase, resulting in abnormal storage of acidic lipid materials particularly in the nerve cells in the central and peripheral nervous systems. GM1 gangliosidosis has three clinical presentations: early infantile, late infantile, and adult. Signs of early infantile GM1 (the most severe subtype, with onset shortly after birth) may include neurodegeneration, seizures, liver and spleen enlargement, coarsening of facial features, skeletal irregularities, joint stiffness, distended abdomen, muscle weakness, exaggerated startle response, and problems with gait. About half of affected patients develop cherry-red spots in the eye. Children may be deaf and blind by age 1 and often die by age 3 from cardiac complications or pneumonia. Onset of late infantile GM1 gangliosidosis is typically between ages 1 and 3 years. Neurological signs include ataxia, seizures, dementia, and difficulties with speech. Onset of adult GM1 gangliosidosis is between ages 3 and 30. Symptoms include muscle atrophy, neurological complications that are less severe and progress at a slower rate than in other forms of the disorder, corneal clouding in some patients, and dystonia (sustained muscle contractions that cause twisting and repetitive movements or abnormal postures). Angiokeratomas may develop on the lower part of the trunk of the body. The size of the liver and spleen in most patients is normal.

The GM2 gangliosidoses also cause the body to store excess acidic fatty materials in tissues and cells, most notably in nerve cells. These disorders result from a deficiency of the enzyme beta-hexosaminidase. The GM2 disorders include Tay-Sachs disease and Sandhoff diseases.

Tay-Sachs disease (also known as GM2 gangliosidosis-variant B). Tay-Sachs and its variant forms are caused by a deficiency in the enzyme hexosaminidase A. The incidence is particularly high among Eastern European and Ashkenazi Jewish populations, as well as certain French Canadians and Louisianan Cajuns. Affected children appear to develop normally for the first few months of life. Symptoms begin by 6 months of age and include progressive loss of mental ability, dementia, decreased eye contact, increased startle reflex to noise, progressive loss of hearing leading to deafness, difficulty in swallowing, blindness, cherry-red spots in the retinas, and some paralysis. Seizures may begin in the child's second year. Children may eventually need a feeding tube and they often die by age 4 from recurring infection. No specific treatment is available. Anticonvulsant medications may initially control seizures. Other supportive treatment includes proper nutrition and hydration and techniques to keep the airway open. A rarer form of the disorder, called late-onset Tay-Sachs disease, occurs in patients in their twenties and early thirties and is characterized by unsteadiness of gait and progressive neurological deterioration.

Sandhoff disease (variant AB). This is a severe form of Tay-Sachs disease. Onset usually occurs at the age of 6 months and is not limited to any ethnic group. Neurological signs may include progressive deterioration of the central nervous system, motor weakness, early blindness, marked startle response to sound, spasticity, myoclonus (shock-like contractions of a muscle), seizures, macrocephaly (an abnormally enlarged head), and cherry-red spots in the eye. Other symptoms may include frequent respiratory infections, murmurs of the heart, doll-like facial features, and an enlarged liver and spleen. There is no specific treatment for Sandhoff disease. As with Tay-Sachs disease, supportive treatment includes keeping the airway open and proper nutrition and hydration. Anticonvulsant medications may initially control seizures. Children generally die by age 3 from respiratory infections.

Krabbé Disease and Symptoms

In one embodiment the lipid storage disorder is Krabbé disease. Krabbé disease (also known as globoid cell leukodystrophy and galactosylceramide lipidosis) is an autosomal recessive disorder caused by deficiency of the enzyme galactocerebrosidase. The disease most often affects infants, with onset before age 6 months, but can occur in adolescence or adulthood. The buildup of undigested fats affects the growth of the nerve's protective myelin sheath and causes severe deterioration of mental and motor skills. Other symptoms include muscle weakness, hypertonia (reduced ability of a muscle to stretch), myoclonic seizures (sudden, shock-like contractions of the limbs), spasticity, irritability, unexplained fever, deafness, optic atrophy and blindness, paralysis, and difficulty when swallowing. Prolonged weight loss may also occur. The disease may be diagnosed by its characteristic grouping of cells into globoid bodies in the white matter of the brain, demyelination of nerves and degeneration, and destruction of brain cells. In infants, the disease is generally fatal before age 2. Patients with a later onset form of the disease have a milder course of the disease and live significantly longer.

Metachromatic Leukodystrophy and Symptoms

In one embodiment the lipid storage disease is a Metachromatic leukodystrophy (MLD). MLD is a group of disorders marked by storage buildup in the white matter of the central nervous system and in the peripheral nerves and to some extent in the kidneys. Similar to Krabbé disease, MLD affects the myelin that covers and protects the nerves. This autosomal recessive disorder is caused by a deficiency of the enzyme arylsulfatase A. Both males and females are affected by this disorder.

MLD has three characteristic phenotypes: late infantile, juvenile, and adult. The most common form of the disease is late infantile, with onset typically between 12 and 20 months following birth. Infants may appear normal at first but develop difficulty in walking and a tendency to fall, followed by intermittent pain in the arms and legs, progressive loss of vision leading to blindness, developmental delays, impaired swallowing, convulsions, and dementia before age 2. Children also develop gradual muscle wasting and weakness and eventually lose the ability to walk. Most children with this form of the disorder die by age 5. Symptoms of the juvenile form typically begin between ages 3 and 10. Symptoms include impaired school performance, mental deterioration, ataxia, seizures, and dementia. Symptoms are progressive with death occurring 10 to 20 years following onset. In the adult form, symptoms begin after age 16 and may include impaired concentration, depression, psychiatric disturbances, ataxia, seizures, tremor, and dementia. Death generally occurs within 6 to 14 years after onset of symptoms.

Bone marrow transplantation may delay progression of the disease in some cases. Considerable progress has been made with regard to gene therapies in animal models of MLD.

Wolman's Disease and Symptoms

In one embodiment the lipid storage disorder is Wolman's disease. Wolman's disease, also known as acid lipase deficiency, is a severe lipid storage disorder that is usually fatal by age 1. This autosomal recessive disorder is marked by accumulation of cholesteryl esters (normally a transport form of cholesterol) and triglycerides (a chemical form in which fats exist in the body) that can build up significantly and cause damage in the cells and tissues. Both males and females are affected by this disorder. Infants are normal and active at birth but quickly develop progressive mental deterioration, enlarged liver and grossly enlarged spleen, distended abdomen, gastrointestinal problems including steatorrhea (excessive amounts of fats in the stools), jaundice, anemia, vomiting, and calcium deposits in the adrenal glands, causing them to harden.

Cholesteryl Ester Storage Disease and Symptoms

In one embodiment the lipid storage disorder is Cholesteryl ester storage disease, which is characterized by an acid lipase deficiency. Cholesteryl ester storage disease results from storage of cholesteryl esters and triglycerides in cells in the blood and lymph and lymphoid tissue. Children develop an enlarged liver leading to cirrhosis and chronic liver failure before adulthood. Children may also have calcium deposits in the adrenal glands and may develop jaundice late in the disorder.

Glycogen Storage Disorders

Herein, the inventors have identified compounds that shift cellular energy metabolism from fatty acid oxidation to glycolysis. Such compounds render a cell more likely to utilize glucose substrates more readily as an energy source. Accordingly, in one aspect of the invention, the compounds of the invention are used to treat or prevent a glycogen storage disease. The method comprises administering a therapeutically effective amount of the compound to a subject in need of treatment, wherein the compound is selected from Table 1, from Table 2, or from Table 3.

Glycogen storage disease (GSD) (also glycogenosis and dextrinosis) is the result of defects in the processing of glycogen synthesis or breakdown within muscles, liver, and other cell types. GSD may be genetic and acquired. Genetic GSD is caused by any inborn error of metabolism (genetically defective enzymes) involved in these processes. In livestock, acquired GSD is caused by intoxication with the alkaloid castanospermine. Non-limiting examples of glycogen storage diseases include von Gierke's disease, Pompe's disease, Cori's disease or Forbes' disease, Andersen disease, McArdle disease, Hers' disease, Tarui's disease, Fanconi-Bickel syndrome.

A person with a Glycogen Storage Disease (GSD) has an absence or deficiency of one of the enzymes responsible for making or breaking down glycogen in the body. This is called an enzyme deficiency. The enzyme deficiency causes either abnormal tissue concentrations of glycogen (too much or too little) or incorrectly or abnormally formed glycogen (shaped wrong). Depending on the type of GSD a person has, their enzyme deficiency may be important in all parts of the body, or only in some parts of the body, like the liver or muscle. Typically, the forms of GSD are described by the part of the body that has trouble because of the enzyme deficiency. The categories most often are: the liver only, the muscles only, or both the liver and the muscles. Other systems that may be involved include blood cells (red blood cells, white blood cells, and platelets), heart, and kidneys amongst others.

All types of GSD cause the body to either not be able to make enough glucose, or not be able to use glucose as a form of energy. Determining what type of GSD a person has (diagnosis) depends on an individual's symptoms. Typically a doctor will do a physical examination and some blood and urine testing. Occasionally, a muscle and/or liver biopsy will be needed to measure the amount of a certain enzyme in that part of the body.

Pompe Disease and Symptoms

In one embodiment the glycogen storage disorder is Pompe disease (also known as GSD II). Pompe disease is an inherited and often fatal disorder that disables the heart and muscles. It is caused by mutations in a gene that makes an enzyme called alpha-glucosidase (GAA). Normally, the body uses GAA to break down glycogen, a stored form of sugar used for energy. But in Pompe disease, mutations in the GAA gene reduce or completely eliminate this essential enzyme. Excessive amounts of glycogen accumulate everywhere in the body, but the cells of the heart and skeletal muscles are the most seriously affected. Researchers have identified up to 70 different mutations in the GAA gene that cause the symptoms of Pompe disease, which can vary widely in terms of age of onset and severity. The severity of the disease and the age of onset are related to the degree of enzyme deficiency.

Early onset (or infantile Pompe disease is the result of complete or near complete deficiency of GAA. Symptoms begin in the first months of life, with feeding problems, poor weight gain, muscle weakness, floppiness, and head lag. Respiratory difficulties are often complicated by lung infections. The heart is grossly enlarged. More than half of all infants with Pompe disease also have enlarged tongues. Most babies with Pompe disease die from cardiac or respiratory complications before their first birthday.

Late onset (or juvenile/adult) Pompe disease is the result of a partial deficiency of GAA. The onset can be as early as the first decade of childhood or as late as the sixth decade of adulthood. The primary symptom is muscle weakness progressing to respiratory weakness and death from respiratory failure after a course lasting several years. The heart may be involved but it will not be grossly enlarged. A diagnosis of Pompe disease can be confirmed by screening for the common genetic mutations or measuring the level of GAA enzyme activity in a blood sample.

von Gierke Disease and Symptoms

In one embodiment the glycogen storage disorder is von Gierke disease (also known as Glycogen storage disease (GSD) type I or hepatorenal glycogenosis). GSD type I is divided into GSD type Ia caused by a glucose-6-phosphatase (G6Pase) deficiency and GSD type Ib resulting from deficiency of a specific translocase T1. Patients with GSD type Ib have altered neutrophil functions predisposing them to gram-positive bacterial infections. GSD type Ic is deficiency of translocase T2 that carries inorganic phosphates from microsomes into the cytosol and pyrophosphates from the cytosol into microsomes. GSD type Id is deficiency in a transporter that translocates free glucose molecules from microsomes into the cytosol. GSD type Ia demonstrates deficient G6Pase activity in the fresh and frozen liver tissue. GSD type Ib demonstrates normal G6Pase activity in the frozen tissue samples and lowered activity in the fresh specimens.

People with Type I GSD are able to store glucose as glycogen but not able to release it normally, with time the stores of glycogen build up in the liver causing the liver to swell (hepatomegaly). Levels of hormones, lactic acid, triglycerides, lipids (fats), uric acid and other by-products of metabolism increase in the blood as the body tries to raise blood sugar. Fats get stored in the liver along with the glycogen, which leads to the enlargement of the liver. The liver does its many other functions normally, and there is not usually any evidence of liver failure. The kidneys are also enlarged due to increased glycogen storage. The continued presence of low blood sugar can eventually leads to delayed growth and development as well as abnormal levels of some metabolites (substances) in the blood and urine. High blood pressure has also been seen in a number of individuals and when this occurs, appropriate treatment is needed.

In addition to the problems described above, individuals with Glycogen Storage Disease Type Ib can develop frequent bacterial and fungal infections, due to abnormal functioning of the white blood cells called neurophils. These are the fighter cells of the body. Therefore, people with GSD Ib can have low levels of neutrophils in their blood (a finding called neutropenia). Many people with GSD Ib use a medicine called GCSF to increase the number of neutrophils in the body. People with Glycogen Storage Disease Type Ib may also develop chronic pancreatitis, chronic inflammatory bowel disease, and Crohn's disease.

Patients with Type I Glycogen Storage Disease may develop benign tumors in the liver called hepatic adenomas. Adenomas are usually first noted around the time of puberty. They typically do not cause symptoms and are identified by routine imaging studies of the liver. In rare instances these can develop into liver cancer.

Renal (kidney) disease is another complication in GSD I patients, and most patients with type I glycogen storage disease older than age 20 yr have proteinuria (proteins excreted in urine). Many also have hypertension (high blood pressure), and kidney stones, among other changes in kidney functions. More severe kidney injury may occur with large amounts of protein in the urine, high blood pressure, and decreased ability of the kidneys to filter waste products due to damage to the filtering units of the kidney (glomeruli). In some patients with the advancement of renal/kidney disease, kidney failure can happen which can require dialysis and eventually kidney transplantation. Other complications can include pulmonary hypertension, radiographic (X-ray) evidence of osteopenia (weak bones), and fractures.

Type I GSD can be diagnosed through blood studies such as blood glucose, cholesterol, triglycerides, lactate, and uric acid, measurements of growth, and ultrasound or other imaging studies to measure the size of the liver and kidneys. By looking for changes in the genes associated with GSD I, genetic (DNA) testing can be used to diagnose the majority of individuals with GSD Type Ia and Ib. Sometimes liver biopsy analysis will be needed to examine the enzyme levels of someone suspected to have Type I Glycogen Storage Disease, especially in situations when DNA testing is negative and the clinical suspicion of GSD I is high.

Forbes-Cori Disease and Symptoms

In one embodiment the glycogen storage disorder is Forbes-Cori disease (also known as GSD type III or limit dextrinosis). In contrast to GSD type I, liver and skeletal muscles are involved in GSD type III. Glycogen deposited in these organs has an abnormal structure. Differentiating patients with GSD type III from those with GSD type I solely on the basis of physical findings is not easy.

There are two types of GSD III known as type Ma and type Mb. Most patients with Type III GSD have enzyme deficiency (i.e. glycogen debrancher enzyme (GDE) deficiency) in liver and skeletal muscle. Patients that have enzyme deficiency in liver and muscle (including sometimes the heart muscle) have what is know as type GSD Ma. Some patients (<15%) have debranching enzyme deficiency only in the liver which is type GSD Mb. During early years of infancy and childhood, the disease may present clinically just like GSD I: small stature, large liver, poor muscle tone (hypotonia) and hypoglycemia. Some liver symptoms (enlarged liver) often improve with age and may disappear after puberty. However, in some patients liver cirrhosis (damage to liver cells) can occur due to accumulation of abnormal glycogen.

Children with GSD III are often first diagnosed because they have swollen (distended) abdomens (belly) due to a very large liver. Some children have problems with low blood sugars when fasting (not eating for 4 hours) but this is not as common or as severe as in GSD I. Growth may be delayed or slow during childhood but most individuals reach a normal adult height. Muscle weakness (GSD Ma) is commonly present in childhood and can, at times, become severe in adult age (requiring use of a wheel chair for mobility by 50-60 years). Although the enzyme defect does not go away, the liver often returns to a smaller size at puberty.

Elevated glycogen content is present in liver and muscle cells. A definite diagnosis and sub-typing (determining Ma versus IIIb type) requires either liver biopsies or DNA based genetic testing. Biopsy of the liver shows inflammatory changes (swollen liver cells) with great elevations of abnormal-structured glycogen content and a deficiency of the debrancher enzyme (GDE). In GSD Ma, biopsy of muscle and liver shows an accumulation of abnormal-structured glycogen and deficiency of debrancher enzyme. However, if only the liver is examined, the type of GSD cannot be determined. If genetic testing is performed and the person has a gene change in the area associated with GSD Mb, a doctor may be able to use the mutation information and clinical information to determine GSD III type (type a versus type b).

Other complications associated with GSD III can include radiographic (X-ray) evidence of osteopenia (weak bones) and fractures. Often, a DEXA bone scan will be required to measure bone density. Also, chemical analysis of the blood usually shows low blood sugar and elevated levels of fat (cholesterol/lipids). However, uric acid and lactic acid levels, which are usually elevated in GSD I patients, are usually normal.

Andersen Disease and Symptoms

In one embodiment, the glycogen storage disorder is Andersen disease. GSD type IV, also known as amylopectinosis or Andersen disease, is a rare disease that leads to early death. In 1956, Andersen reported the first patient with progressive hepatosplenomegaly and accumulation of abnormal polysaccharides. The main clinical features are liver insufficiency and abnormalities of the heart and nervous system.

In Type IV GSD there is not an increased amount of glycogen in the tissues, as in other forms of GSD. Instead, the glycogen that does accumulate has very long outer branches, because there is a genetic deficiency of the branching enzyme. This structural abnormality of the glycogen is thought to trigger the body's immune system, causing the body to actually attack the glycogen and the tissues in which it is stored. The result is tremendous scarring (cirrhosis) of the liver as well as other organs, such as muscle. The typical symptomatology of this disease is the result of the scarring process.

A baby with the typical Type IV GSD appears to be normal at birth. The first indication of a problem is a failure to thrive. The rate of growth and mental progress of the baby stops at a certain point and does not continue normally. The liver and spleen enlarge, there is little weight gain, and muscles develop poor tone. The course of the disease is one of progressive cirrhosis and associated problems. Death typically occurs by five years of age.

McArdle Disease and Symptoms

In one embodiment, the glycogen storage disorder is McArdel disease, GSD type V, also known as McArdle disease, affects the skeletal muscles. Initial signs of the disease usually develop in adolescents or adults. Muscle phosphorylase deficiency adversely affects the glycolytic pathway in skeletal musculature causes GSD type V. Like other forms of GSD, McArdle disease is heterogeneous.

People with Type V GSD experience problems performing and completing most exercises, especially anaerobic exercises. Because they lack the enzyme to metabolize glycogen, which is the main source of energy for anaerobic activity, their body struggles to find other sources of energy to complete a given activity or exercise. Under these circumstances, the body breaks down muscle when trying to attain energy. This causes many symptoms such as muscle pain, muscle cramping, muscle fatigue, and muscle tenderness. With the breakdown of muscle (rhabdomyolysis) and the release of the red protein myoglobin, myoglobinuria may develop, as evidenced by dark-red or red-brown urine. Serum creatine kinase levels will be greatly elevated.

The physical exam of patients with Type V glycogen storage disease is normal. They complain of painful muscle cramps after exercise. These persons are commonly muscular; they do not have large livers, and are normal in height. Their liver phosphorylase activity is normal, and they do not have hypoglycemia. A muscle biopsy will show increased concentrations of glycogen, and a deficiency of the phosphorylase enzyme.

Hers Disease and Symptoms

In one embodiment, the glycogen storage disorder Hers disease. GSD type VI, also known as Hers disease, belongs to the group of hepatic glycogenoses. Hepatic phosphorylase deficiency or deficiency of other enzymes that form a cascade necessary for liver phosphorylase activation cause the disease.

Clinically, this form of glycogen storage disease appears to be similar to, but is usually considerably milder than glucose-6-phosphatase deficiency GSD (type I GSD) since glucose can be made from protein. These patients present with hepatomegaly (liver enlargement) and growth retardation early in childhood. Since people with Type VI GSD are able to store glucose as glycogen but not able to release it normally, with time the stores of glycogen build up in the liver causing the liver to swell (hepatomegaly). Hypoglycemia (low blood sugars) and elevated ketone concentrations in the blood and urine after a period of fasting are the hallmarks of these disorders. Hyperlipidemia (elevated cholesterol and fats in the blood) and abnormalities in the liver function tests are usually mild if present. Lactic acid and uric acid are normal. The heart and skeletal muscles are not involved. The hepatomegaly improves with good metabolic control. Hepatic adenomas are rare in well treated individuals with GSD VI, and liver failure does not occur.

The diagnosis of this disease can be made by genetic testing from DNA extracted from blood or saliva. Liver biopsies to measure phosphorylase activity, which is reduced in this disease, are not necessary in most cases and not recommended if type VI GSD is suspected.

Tarui Disease and Symptoms

In one embodiment, the glycogen storage disorder Tarui disease. GSD type VII, also known as Tarui disease, arises as a result of phosphofructokinase (PFK) deficiency. The enzyme is located in skeletal muscles and erythrocytes. The clinical and laboratory features are similar to those of GSD type V. Patients experience early onset of fatigue and muscle pain with exercise. The body breaks down muscle when trying to attain energy, which causes many symptoms such as muscle pain, muscle cramping, muscle fatigue, and muscle tenderness. With the breakdown of muscle (rhabdomyolysis) and the release of the red protein myoglobin, myoglobinuria may develop, as evidenced by dark-red or red-brown urine. However, exercise intolerance is evident in childhood and symptoms are more severe than in Type V GSD. Diagnosis of Type VII Glycogen Storage Disease is done by muscle biopsy, with a deficiency of the muscle phosphofructokinase enzyme and a modest accumulation of glycogen found. Patients may also display a hemolytic anemia.

In one embodiment, the lipid/glycogen storage disorder is characterized by myopathy. In one embodiment the myopathy is a lipid storage myopathy.

In one embodiment, the myopathy is cardiomyopathy.

In one embodiment, the lipid/glycogen storage disorder characterized by myopathy is neutral lipid storage disease (NLSD). In one embodiment, the lipid/glycogen storage disorder characterized by myopathy is neutral lipid storage disease associated with myopathy (NLSD-M). Thus, in one aspect of the invention, a method is provided for treating or preventing neutral lipid storage disease (e.g. NLSD or NLSD-M) in a subject in need of treatment, the method comprising administering to a subject a therapeutically effective amount of compound selected from Table 1, Table 2, or Table 3. In one embodiment, the compound is selected from Table 1. In one embodiment the compound is selected from Table 2. In on embodiment, the compound is selected from Table 3.

In some embodiments of the methods described herein further comprise selecting a subject diagnosed with a lipid/glycogen storage disorder. Diagnosis can be made through clinical examination, biopsy, genetic testing (for mutations predictive of the disorder), molecular analysis of cells or tissues, and enzyme assays (testing a variety of cells or body fluids for enzyme deficiency). A subject suffering from a lipid/glycogen storage disorder can further be selected based on the symptoms presented. For example, a subject diagnosed as suffering from Gaucher disease may based on the presence of an enlarged spleen and liver, liver malfunction, skeletal disorders and bone lesions that may cause pain and fractures, severe neurologic complications, swelling of lymph nodes and (occasionally) adjacent joints, distended abdomen, a brownish tint to the skin, anemia, low blood platelets, and yellow spots in the eyes, and/or the presence of a deficiency of the enzyme glucocerebrosidase. Symptoms and enzyme deficiencies of other various lipid/glygogen disorders are described herein.

Biopsy for lipid or glycogen storage diseases involves removing a small sample of the liver or other tissue and studying it under a microscope, or subjecting the tissue sample to quantitative/qualitative assays. In this procedure, a physician will administer a local anesthetic and then remove a small piece of tissue either surgically or by needle biopsy (a small piece of tissue is removed by inserting a thin, hollow needle through the skin). The tissue sample is analyzed for e.g. lipid deposition, or enzymatic activity. Genetic testing for lipid/glycogen storage disease may be done to determine if they are carrying a mutated gene that causes the disorder.

Treatment and Prevention of Obesity

In another aspect, the invention described herein features a method for treating or preventing obesity in a subject, the method comprising: administering a therapeutically effective amount of a compound to a subject (e.g. a compound selected from Table 1, Table 2, or Table 3), wherein the compound reduces accumulation of lipids within cells. In one embodiment, the lipid deposition in obesity is alleviated by at least 20%, at least 30%, at least 40%, or at least 50%, e.g. as measured by a reduction in Body Mass Index (BMI). In one embodiment, one more symptoms associated with obesity are alleviated by at least 20%, at least 30%, at least 40%, or at least 50%. In one embodiment, the lipid deposition in obesity is alleviated is alleviated by more that 50%. In some embodiments, the symptoms of obesity improves by at least about 10%, 20%, 30%, 40%, 50%, 60%, 70% or more.

Symptoms of obesity include, but are not limited to, difficulty in doing daily activities, lethargy, breathlessness, increased weight, and secondary problems, e.g. heart disease, high blood pressure, type 2 diabetes, gallstones, breathing problems, and certain cancers.

In some embodiments, the methods described herein further comprise selecting a subject diagnosed with obesity. Diagnosis of obesity can be made through clinical evaluation. In one embodiment diagnosis is based upon n a Body Mass Index (BMI) greater than or equal to 30 kg/m$^2$. In one embodiment diagnosis is made based upon excessive fat tissue in and around the abdomen, i.e. a waist to hip ratio higher than 0.90 in men or a waist to hip ratio higher than 0.85 in women.

Compounds

The compounds of the present invention are useful in the methods described herein for reducing the accumulation of lipids within cells, and accordingly are useful for the treatment and prevention of a lipid/glycogen storage diseases, as well as for the treatment and prevention of obesity. In one embodiment, the compound for use in methods of the present invention is a compound selected from the compounds listed in Table 1. In one embodiment, the compound for use in methods of the present invention is a compound selected from the compounds listed in Table 2. In one embodiment, the compound for use in methods of the present invention is a compound selected from the compounds listed in Table 3.

The compounds described herein are positive hits from a screen using the Prestwick Collection™ of off-patent drugs (generic), and all are commercially available. Commercial sources of the compounds include, for example, Prestwick Chemical, Washington, D.C.; and Sigma-Aldrich Co., St. Louis, Mo. Alternatively, the compounds described herein can be synthesized using means well known to those of skill in the art. The compounds may be formulated in combination with additional compounds (e.g. compounds useful for treatment of symptoms of lipid/glycogen storage disorders) and may be formulated as pharmaceutically acceptable compositions, See the heading "Formulations and administration", herein.

In one embodiment, the compound used in methods for reducing lipid accumulation with in cells is selected from the group consisting of: Fendiline hydrochloride, Vinpocetine, Mefloquine hydrochloride, Perhexyline maleate, Gossypol, Butylparaben, Clotrimazole, Fluspirilen, Cinnarizine, Ebselen, Ethynodiol diacetate, Thiethylperazine malate, Tamoxifen citrate, Chrysene-1,4-quinone, Biperiden hydrochloride, Clemastine fumarate, GBR 12909 dihydrochloride, Chlorprothixene hydrochloride, Clomipramine hydrochloride, Homosalate, Pimozide, Sulconazole nitrate, Naftifine hydrochloride, Piperidolate hydrochloride, Sertaconazole nitrate, Menadione, Phenformin hydrochloride, Cyclobenzaprine hydrochloride, Triflupromazine hydrochloride, Methiothepin maleate, Phenoxybenzamine hydrochloride, (1-[(4-Chlorophenyl)phenyl-methyl]-4-methylpiperazine), Merbromin, Ascorbic acid, Bisacodyl, Altretamine, Testosterone propionate, Cloperastine hydrochloride, Pregnenolone, Clomiphene citrate (Z,E), Nifuroxazide.

In some embodiments, the compound to reduce lipid accumulation in a cell is not one of the compounds selected from the following list of compounds: Fendiline hydrochloride, Vinpocetine, Mefloquine hydrochloride, Perhexyline maleate, Gossypol, Butylparaben, Clotrimazole, Fluspirilen, Cinnarizine, Ebselen, Ethynodiol diacetate, Thiethylperazine malate, Tamoxifen citrate, Chrysene-1,4-quinone, Biperiden hydrochloride, Clemastine fumarate, GBR 12909 dihydrochloride, Chlorprothixene hydrochloride, Clomipramine hydrochloride, Homosalate, Pimozide, Sulconazole nitrate, Naftifine hydrochloride, Piperidolate hydrochloride, Sertaconazole nitrate, Menadione, Phenformin hydrochloride, Cyclobenzaprine hydrochloride, Triflupromazine hydrochloride, Methiothepin maleate, Phenoxybenzamine hydrochloride, (1-[(4-Chlorophenyl)phenyl-methyl]-4-methylpiperazine), Merbromin, Ascorbic acid, Bisacodyl, Altretamine, Testosterone propionate, Cloperastine hydrochloride, Pregnenolone, Clomiphene citrate (Z,E), Nifuroxazide.

In one aspect, the invention described herein features a method of treating a lipogen/glycogen storage disorder in a subject. The method comprises administering to a subject a therapeutically effective amount of a compound selected from Table 1, from Table 2, or from Table 3.

In one embodiment the lipid/glycogen storage disorder to be treated with a compound selected from Table 1, or from Table 2, or from Table 3, is not Activator Deficiency/GM2 Gangliosidosis.

In one embodiment the lipid/glycogen storage disorder to be treated with a compound selected from Table 1, or from Table 2, or from Table 3, is not Alpha-mannosidosis.

In one embodiment the lipid/glycogen storage disorder to be treated with a compound selected from Table 1, or from Table 2, or from Table 3, is not Aspartylglucosaminuria.

In one embodiment the lipid/glycogen storage disorder to be treated with a compound selected from Table 1, or from Table 2, or from Table 3, is not Cholesteryl ester storage disease.

In one embodiment the lipid/glycogen storage disorder to be treated with a compound selected from Table 1, or from Table 2, or from Table 3, is not Chronic Hexosaminidase A Deficiency.

In one embodiment the lipid/glycogen storage disorder to be treated with a compound selected from Table 1, or from Table 2, or from Table 3, is not Cystinosis.

In one embodiment the lipid/glycogen storage disorder to be treated with a compound selected from Table 1, or from Table 2, or from Table 3, is not Danon disease.

In one embodiment the lipid/glycogen storage disorder to be treated with a compound selected from Table 1, or from Table 2, or from Table 3, is not Fabry disease.

In one embodiment the lipid/glycogen storage disorder to be treated with a compound selected from Table 1, or from Table 2, or from Table 3, is not Farber disease.

In one embodiment the lipid/glycogen storage disorder to be treated with a compound selected from Table 1, or from Table 2, or from Table 3, is not Fucosidosis.

In one embodiment the lipid/glycogen storage disorder to be treated with a compound selected from Table 1, or from Table 2, or from Table 3, is not Galactosialidosis.

In one embodiment the lipid/glycogen storage disorder to be treated with a compound selected from Table 1, or from Table 2, or from Table 3, is not Gaucher Disease (e.g. Type I, Type II, or Type III).

In one embodiment the lipid/glycogen storage disorder to be treated with a compound selected from Table 1, or from Table 2, or from Table 3, is not GM1 gangliosidosis (e.g. Infantile, Late infantile/Juvenile, Adult/Chronic).

In one embodiment the lipid/glycogen storage disorder to be treated with a compound selected from Table 1, or from Table 2, or from Table 3, is not I-Cell disease/Mucolipidosis II.

In one embodiment the lipid/glycogen storage disorder to be treated with a compound selected from Table 1, or from Table 2, or from Table 3, is not infantile Free Sialic Acid Storage Disease/ISSD.

In one embodiment the lipid/glycogen storage disorder to be treated with a compound selected from Table 1, or from Table 2, or from Table 3, is not Juvenile Hexosaminidase A Deficiency.

In one embodiment the lipid/glycogen storage disorder to be treated with a compound selected from Table 1, or from Table 2, or from Table 3, is not Krabbe disease (e.g. Infantile Onset, Late Onset).

In one embodiment the lipid/glycogen storage disorder to be treated with a compound selected from Table 1, or from Table 2, or from Table 3, is not Lysosomal acid lipase deficiency (e.g. Early onset or Late onset).

In one embodiment the lipid/glycogen storage disorder to be treated with a compound selected from Table 1, or from Table 2, or from Table 3, is not Metachromatic Leukodystrophy.

In one embodiment the lipid/glycogen storage disorder to be treated with a compound selected from Table 1, or from Table 2, or from Table 3, is not a Mucopolysaccharidoses disorder (e.g. Pseudo-Hurler polydystrophy/Mucolipidosis IIIA, MPSI Hurler Syndrome.

In one embodiment the lipid/glycogen storage disorder to be treated with a compound selected from Table 1, or from Table 2, or from Table 3, is not MPSI Scheie Syndrome, MPS I Hurler-Scheie Syndrome.

In one embodiment the lipid/glycogen storage disorder to be treated with a compound selected from Table 1, or from Table 2, or from Table 3, is not MPS II Hunter syndrome, Sanfilippo syndrome Type A/MPS III A.

In one embodiment the lipid/glycogen storage disorder to be treated with a compound selected from Table 1, or from Table 2, or from Table 3, is not Sanfilippo syndrome Type B/MPS III B.

In one embodiment the lipid/glycogen storage disorder to be treated with a compound selected from Table 1, or from Table 2, or from Table 3, is not Sanfilippo syndrome Type C/MPS III C.

In one embodiment the lipid/glycogen storage disorder to be treated with a compound selected from Table 1, or from Table 2, or from Table 3, is not Sanfilippo syndrome Type D/MPS III D.

In one embodiment the lipid/glycogen storage disorder to be treated with a compound selected from Table 1, or from Table 2, or from Table 3, is not Morquio Type A/MPS IVA or Morquio Type B/MPS IVB.

In one embodiment the lipid/glycogen storage disorder to be treated with a compound selected from Table 1, or from Table 2, or from Table 3, is not MPS IX Hyaluronidase Deficiency.

In one embodiment the lipid/glycogen storage disorder to be treated with a compound selected from Table 1, or from Table 2, or from Table 3, is not MPS VI Maroteaux-Lamy.

In one embodiment the lipid/glycogen storage disorder to be treated with a compound selected from Table 1, or from Table 2, or from Table 3, is not MPS VII Sly Syndrome.

In one embodiment the lipid/glycogen storage disorder to be treated with a compound selected from Table 1, or from Table 2, or from Table 3, is not Mucolipidosis I/Sialidosis.

In one embodiment the lipid/glycogen storage disorder to be treated with a compound selected from Table 1, or from Table 2, or from Table 3, is not Multiple sulfatase deficiency.

In one embodiment the lipid/glycogen storage disorder to be treated with a compound selected from Table 1, or from Table 2, or from Table 3, is not Niemann-Pick Disease (e.g. Type A, Type B, or Type C).

In one embodiment the lipid/glycogen storage disorder to be treated with a compound selected from Table 1, or from Table 2, or from Table 3, is not a Neuronal Ceroid Lipofuscinoses disorder (e.g., CLN6 disease (e.g. Atypical Late Infantile, Late Onset variant, Early Juvenile).

In one embodiment the lipid/glycogen storage disorder to be treated with a compound selected from Table 1, or from Table 2, or from Table 3, is not Batten-Spielmeyer-Vogt/Juvenile NCL/CLN3 disease.

In one embodiment the lipid/glycogen storage disorder to be treated with a compound selected from Table 1, or from Table 2, or from Table 3, is not Finnish Variant Late Infantile CLN5.

In one embodiment the lipid/glycogen storage disorder to be treated with a compound selected from Table 1, or from Table 2, or from Table 3, is not Jansky-Bielschowsky disease/Late infantile CLN2/TPP1 Disease.

In one embodiment the lipid/glycogen storage disorder to be treated with a compound selected from Table 1, or from Table 2, or from Table 3, is not Kufs/Adult-onset NCL/CLN4 disease.

In one embodiment the lipid/glycogen storage disorder to be treated with a compound selected from Table 1, or from Table 2, or from Table 3, is not Northern Epilepsy/variant late infantile CLN8.

In one embodiment the lipid/glycogen storage disorder to be treated with a compound selected from Table 1, or from Table 2, or from Table 3, is not Santavuori-Haltia/Infantile CLN1/PPT disease, Beta-mannosidosis).

In one embodiment the lipid/glycogen storage disorder to be treated with a compound selected from Table 1, or from Table 2, or from Table 3, is not Pompe disease/Glycogen storage disease type II.

In one embodiment the lipid/glycogen storage disorder to be treated with a compound selected from Table 1, or from Table 2, or from Table 3, is not Hypertrophic cardiomyopathy (e.g. due to glycogen storage from AMPK-gamma2 or LAMP2 mutation).

In one embodiment the lipid/glycogen storage disorder to be treated with a compound selected from Table 1, or from Table 2, or from Table 3, is not Pycnodysostosis.

In one embodiment the lipid/glycogen storage disorder to be treated with a compound selected from Table 1, or from Table 2, or from Table 3, is not GM2 Gangliosidosis.

In one embodiment the lipid/glycogen storage disorder to be treated with a compound selected from Table 1, or from Table 2, or from Table 3, is not GM1 Gangliosidosis.

In one embodiment the lipid/glycogen storage disorder to be treated with a compound selected from Table 1, or from Table 2, or from Table 3, is not Schindler disease.

In one embodiment the lipid/glycogen storage disorder to be treated with a compound selected from Table 1, or from Table 2, or from Table 3, is not Salla disease/Sialic Acid Storage Disease.

In one embodiment the lipid/glycogen storage disorder to be treated with a compound selected from Table 1, or from Table 2, or from Table 3, is not Tay-Sachs/GM2 gangliosidosis.

In one embodiment the lipid/glycogen storage disorder to be treated with a compound selected from Table 1, or from Table 2, or from Table 3, is not Wolman disease.

In one aspect, the invention teaches a method for treating or preventing obesity in a subject. The method comprises administering to a subject a compound selected from Table 1, from Table 2, or from Table 3.

In some embodiments, the compound to treat obesity is not one of the compounds selected from the following list of compounds: Fendiline hydrochloride, Vinpocetine, Mefloquine hydrochloride, Perhexyline maleate, Gossypol, Butylparaben, Clotrimazole, Fluspirilen, Cinnarizine, Ebselen, Ethynodiol diacetate, Thiethylperazine malate, Tamoxifen citrate, Chrysene-1,4-quinone, Biperiden hydrochloride, Clemastine fumarate, GBR 12909 dihydrochloride, Chlorprothixene hydrochloride, Clomipramine hydrochloride, Homosalate, Pimozide, Sulconazole nitrate, Naftifine hydrochloride, Piperidolate hydrochloride, Sertaconazole nitrate, Menadione, Phenformin hydrochloride, Cyclobenzaprine hydrochloride, Triflupromazine hydrochloride, Methiothepin maleate, Phenoxybenzamine hydrochloride, (1-[(4-Chlorophenyl)phenyl-methyl]-4-methylpiperazine), Merbromin, Ascorbic acid, Bisacodyl, Altretamine, Testosterone propionate, Cloperastine hydrochloride, Pregnenolone, Clomiphene citrate (Z,E), Nifuroxazide.

In some embodiments, the compound to treat obesity is not one of the compounds selected from the compounds listed in Table 1.

In other aspects of the invention, methods for treating lipid/glycogen storage disorders and methods for treating obesity are provided; these methods comprise administering a therapeutically effective amount of recombinant ATGL protein to a subject in need thereof (e.g. a subject diagnosed with, or predisposed to having, a lipid/glycogen disorder or obesity (e.g. prophylactic administration)).

As used herein, recombinant ATGL refers to refers to adipose triglyceride lipase enzyme (ATGL, also known as desnutrin) protein, or a fragment ATGL protein, that has been produced using protein expression techniques well known to those of skill in the art, where the recombinant ATGL (which may be a fragment thereof) is capable of cleaving the first ester bond in triacylglycerol (TAG) within cells (i.e. functional ATGL). Methods for expressing functional ATGL are described in, e.g., Duncan et al., Characterization of desnutrin functional domains: critical residues for triacylglycerol hydrolysis in cultured cells *J. Lipid Res.* 2010 51:(2) 309-317. Methods for assessing ATGL enzyme activity are well known to those of skill in the art, e.g. as described in Zimmermann et al. *Science*: Vol. 306 no. 5700 pp. 1383-1386.

In one embodiment, the recombinant ATGL is a fusion protein comprising functional ATGL and a targeting moiety. The recombinant ATGL can comprise more that one targeting moiety. The targeting moiety may be an amino acid sequence that binds to the cell surface, or it may be an amino acid sequence that binds to a subcellular compartment within a cell (e.g. early or late endosomes, ER, Golgi, lipid droplets, lysosomes, nucleus). In some embodiments, the targeting moiety binds to a specific cell surface receptor, e.g. to aid in delivery of the recombinant ATGL into a cell. In some embodiment, the targeting moiety binds to a subcellular compartment of a cell (e.g. lysosome or lipid droplet, e.g. binds to a receptor or molecule found on a subcellular compartment).

In some embodiments, the fusion protein further comprises a linker amino acid sequence. In one embodiment the linker amino acid sequence is capable of being cleaved by an intracellular cellular protease. The fusion protein can further comprise a penetration peptide sequence, e.g. to aid in escape of the ATGL fusion from cellular endocytic compartments, and/or to aid in penetration of functional ATGL into a subcellular compartment.

As used herein, a "linker" is a short (e.g., about 1-40, e.g., 1-20 amino acids) sequence of amino acids that is not part of the ATGL sequence or of the cell penetrating peptide and/or targeting moiety sequence. A linker peptide is attached on its amino-terminal end to one polypeptide or polypeptide domain and on its carboxyl-terminal end to another polypeptide or polypeptide domain. Examples of useful linker peptides include, but are not limited to, glycine polymers ((G)n) including glycine-serine and glycine-alanine polymers where n=1-8, preferably, n=3, 4, 5, or 6).

The term "fusion protein" refers to a recombinant protein of two or more fused proteins. Fusion proteins can be produced, for example, by a nucleic acid sequence encoding one protein joined to the nucleic acid encoding another protein such that they constitute a single open-reading frame that can be translated in the cells into a single polypeptide harboring all the intended proteins. The order of arrangement of the proteins can vary. As a non-limiting example, the nucleic acid sequence encoding ATGL can be fused to either the 5' or the 3' end of the nucleic acid sequence encoding a targeting moiety and/or a penetration peptide.

In some embodiments, the targeting moiety is an antibody, including antibodies or antibody fragments. In one embodiment the antibody recognizes a viral envelope protein, a cellular receptor, or an extracellular domain of an activated receptor. Antibodies and antibody fragments, polyclonal or monoclonal, can be purchased from a variety of commercial suppliers, or may be manufactured using well-known methods, e.g., as described in Harlow et al., Antibodies: A Laboratory Manual, 2nd Ed; Cold Spring Harbor Laboratory Press, Cold Spring Harbor, N.Y. (1988).

As used herein, the term "antibody" refers to immunoglobulin molecules and immunologically active portions of immunoglobulin molecules, i.e., molecules that contain an antigen binding site that bind an antigen. The term includes antibodies comprised of two immunoglobulin heavy chains and two immunoglobulin light chains as well as a variety of forms besides antibodies; including, for example, single chain antibodies Fv, Fab, and F(ab)'2, diabodies, as well as bifunctional hybrid antibodies capable of binding the antigen or antigenic fragment of interest.

In one embodiment, the targeting moiety is a ligand of a cell surface molecule, e.g. to a cell surface receptor, or surface receptor (or molecule) found on a subcellular compartment of a cell. The cell surface receptor may be a transmembrane receptor or a non-transmembrane receptor. In one embodiment the targeting moiety is a soluble receptor. The targeting moiety may target a cell surface receptor, or subcellular compartment receptor, on or in any cell. In one embodiment, the targeting moiety targets a cell surface receptor on adipocytes, liver cells lung cells, muscle cells, or heart cells. In one embodiment, the cell surface receptor undergoes endocytosis. In one embodiment, the cell surface receptor is specific for the target cell. Examples of cell surface receptors include, but are certainly not limited to, hormone receptors e.g. epidermal growth factor receptor (EGFR), fibroblast growth factor receptor (FGFR) etc, transferrin receptors; low density lipoprotein receptor (LDLR), FC receptors, and CD receptors.

In some embodiments, the targeting moiety targets subcellular compartments within a cell (See e.g. Rajendran et al. Subcellular targeting strategies for drug design and delivery *Nature Reviews Drug Discovery* 9, 29-42 (January 2010). In one embodiment, the targeting moiety is a soluble receptor.

In one embodiment, the targeting moiety binds to lysosomes. In one embodiment, the targeting moiety binds to the mannose-6-phosphate receptor. In one embodiment, the targeting moiety comprises a proteoglycan (See, for example, Lemansky and Hasilik, Chondroitin sulfate is involved in lysosomal transport of lysozyme in U937 cells, *J. Cell Sci* 114 (2), 345-352).

In one embodiment, the targeting moiety binds to lipid droplets. For example the targeting moiety may comprise hormone-sensitive lipase (HSL), or fragment thereof, which is known to target lipid droplets within cells (Yang et al. *Cell Metabolism* 11, 194-205, Mar. 3, 2010, 194-205).

In one embodiment, the targeting moiety is tail interacting protein of 47 kDa (TIP47) [or fragment thereof], or a moiety (e.g. peptide or antibody) that binds to tail interacting protein of 47 kDa (TIP47) (Bulankina et al. J. Cell Biol. Vol. 185 No. 4 641-655).

In one embodiment the targeting moiety binds to the COPI and/or COPII coatomer proteins (Soni et al. Coatomer-dependent protein delivery to lipid droplets *J Cell Sci*. 2009 Jun. 1; 122(Pt 11):1834-41). In other embodiments, the targeting moiety comprises a PAT-domain protein, or fragment thereof, e.g. ADRP (adipophilin) and TIP47, which are known to localize to the surface of lipid droplets (Soni et al. Supra). In some embodiments, the targeting moiety binds to a PAT-domain protein. In one embodiment the targeting moiety comprises COPI or COPII, or a fragment thereof.

In one embodiment, the targeting moiety comprises an N-terminal region of comparative gene identification-58 (CGI-58) (e.g. amino acids 1-30 or portion thereof), which harbors a lipophilic tryptophan-rich stretch known to bind lipid droplets (Gruber et al. *Biol Chem* 2010 Apr. 16; 285(16): 12289-98).

In one embodiment, the targeting moiety comprises a cytoplasmic targeting/retention signal, e.g. the region of 18 amino acids within the MA of MPMV that is responsible for type D-specific morphogenesis as described in Choi et al. Identification of a Cytoplasmic Targeting/Retention Signal in a Retroviral Gag Polyprotein *J. Virol.* 1999 July; 73(7): 5431-5437).

In one embodiment, the targeting moiety comprises an amino acid sequence that targets the Golgi complex. In one embodiment, the amino acid sequence comprises a 32-amino acid segment of the putative COOH-terminal cytoplasmic domain of caveolin-3, which is known to specifically and exclusively target to the Golgi complex, as described in Luetterforst et al. Molecular Characterization of Caveolin Association with the Golgi Complex: Identification of a Cis-Golgi Targeting Domain in the Caveolin Molecule, *JCB* 1999 Jun. 28, 145 (7):1443). In one embodiment, the targeting moiety comprises the amino acid sequence AFDNVGYE (SEQ ID NO: 43) (See e.g., Braiterman et al. Apical targeting and Golgi retention signals reside within a 9-amino acid sequence in the copper-ATPase, ATP7B, *Am J Physiol* Gastrointest Liver Physiol. 2009 February; 296(2): G433-G444). In one embodiment, the targeting moiety comprises a fragment of the glycoprotein from Crimean-Congo Hemorrhagic Fever (CCHF) virus, for example as described in Haferkamp et al. Intracellular localization of Crimean-Congo Hemorrhagic Fever (CCHF) virus glycoproteins *Virology Journal*

2005, 2:42. The C-terminal region of glycoprotein $G_C$ targets the endoplasmic reticulum, while the N-terminal glycoprotein $G_N$ localizes to the Golgi.

In other embodiments, the recombinant ATGL is a fusion protein comprising functional ATGL and a cell penetration peptide.

In some embodiments of the methods described herein, the functional ATGL comprises the "patatin-like domain" common to plant acyl-transferases (Dessen et al. Crystal structure of human cytosolic phospholipase A2 reveals a novel topology and catalytic mechanism. Cell 97, 349-360; Lu et al. Differential control of ATGL-mediated lipid droplet degradation by CGI-58 and G0S2, Cell Cycle 2010 Jul. 15; 9(14): 2719-2725.). In some embodiments, the recombinant ATGL 27-mer consisting of N-terminal fragment of neuropeptide galanine and membrane interacting wasp venom peptide mastoporan (Lindgren et al., (2000), Bioconjugate Chem., 11, 619-626); a peptide derived from influenza virus hemagglutinin envelop glycoprotein (Bongartz et al., 1994, Nucleic Acids Res., 22, 468 1 4688); RGD peptide; HIV-1 TAT protein (Frankel and Pabo, (1988) Cell, 55, pp. 1189-93). See also, e.g., Morris, M. C. et al., Nature Biotechnol. 19:1173-1176 (2001); Dupont, A. J. and Prochiantz, A., CRC Handbook on Cell Penetrating Peptides, Langel, Editor, CRC Press, (2002); Chaloin, L. et al., Biochemistry 36(37):11179-87 (1997); and Lundberg, P. and Langel, U., J. Mol. Recognit. 16(5):227-233 (2003); which are each incorporated herein by reference. Non-limiting example cell penetration peptide sequences are set forth in Table 5.

TABLE 5

| PEPTIDE | SEQUENCE | SEQ ID NO: |
| --- | --- | --- |
| HIV-1 TAT (49-57) | RKKRRQRRR | SEQ ID NO: 32 |
| HIV-1 TAT (48-60) | GRKKRRQRRRTPQ | SEQ ID NO: 33 |
| HIV-1 TAT (47-57) | YGRKKRRQRRR | SEQ ID NO: 34 |
| Kaposi fibroblast growth factor | AAV ALL PAV LLA LLA P + VQR KRQ KLMP | SEQ ID NO: 35 |
| of caiman crocodylus Ig(5) light chain | MGL GLH LLV LAA ALQ GA | SEQ ID NO: 36 |
| HIV envelope glycoprotein gp41 | GAL FLG FLG AAG STM GA + PKS KRK 5 (NLS of the SV40) | SEQ ID NO: 37 |
| Drosophila Antennapedia | RQI KIW FQN RRM KWK K amide | SEQ ID NO: 38 |
| influenza virus hemagglutinin envelop glycoprotein | GLFEAIAGFIENGWEGMIDGGG YC | SEQ ID NO: 39 |
| transportan A | GWT LNS AGY LLG KIN LKA LAA LAK KIL | SEQ ID NO: 40 |
| Pre-S-peptide | (S)DH QLN PAF | SEQ ID NO: 41 |
| Somatostatin (tyr-3-octreotate) | (S)FC YWK TCT | SEQ ID NO: 42 |

(S) optional Serine for coupling
italic = optional D isomer for stability comprises the C-terminal hydrophobic domain (Kobayashi K. et al. J. Clin Endocrinol Metab. 2008 July; 93(7):2877-84). In one embodiment, the recombinant ATGL does not comprise the C-terminal hydrophobic domain.

As used herein, a "cell penetration peptide" refers to an amino acid sequence capable of crossing the lipid bilayer of a cell. Several cell penetrating peptides have been identified which can be used as carrier peptides in the methods of the invention for transporting functional ATGL across cell membranes. These peptides include, but are not limited to, the homeodomain of antennapedia, a Drosophila transcription factor (Wang et al., (1995) PNAS USA., 92, 3318-3322); a fragment representing the hydrophobic region of the signal sequence of Kaposi fibroblast growth factor with or without NLS domain (Antopolsky et al. (1999) Bioconj. Chem., 10, 598-606); a signal peptide sequence of caiman crocodylus Ig(5) light chain (Chaloin et al. (1997) Biochem. Biophys. Res. Comm., 243, 601-608); a fusion sequence of HIV envelope glycoprotein gp4114, (Morris et al. (1997) Nucleic Acids Res., 25, 2730-2736); a transportan A-achimeric In another embodiment, the cell penetrating peptide comprises a membrane signal peptide or membrane translocation sequence capable of translocating across the cell membrane. A cell penetrating "signal peptide" or "signal sequence" refers to a sequence of amino acids generally of a length of about 10 to about 50 or more amino acid residues, many (typically about 55-60%) residues of which are hydrophobic such that they have a hydrophobic, lipid-soluble portion. Generally, a signal peptide is a peptide capable of penetrating through the cell membrane to allow the import and/or export of cellular proteins. Signal peptides can be selected from the SIGPEP database (von Heijne, Protein Sequence Data Analysis 1:4142 (1987); von Heijne and Abrahmsen, L., FEBS Letters 224:439-446 (1989)). Algorithms can also predict signal peptide sequences for use in the compositions (see, e.g., SIGFIND—Signal Peptide Prediction Server version SignalP V2.0b2, Bendtsen et al. "Improved prediction of signal peptides: SignalP 3.0." J. Mol. Biol., 340:783-795, 2004; Nielsen et al. "Identification of prokaryotic and eukaryotic signal peptides and prediction of their cleavage sites."

Protein Engineering, 10:1-6, 1997; Bairoch and Boeckmann, "The SWISS-PROT protein sequence data bank: current status" Nucleic Acids Res. 22:3578-3580, 1994.).

In some embodiments of the present invention, recombinant ATGL further comprises a cell penetrating agent and/or targeting moiety as described herein, that is not present as fusion protein with ATGL. For example, the recombinant ATGL may have a cell penetrating peptide and/or targeting moiety conjugated the recombinant ATGL protein by chemical bond linkages, such as linkages by disulfide bonds or by chemical bridges. Peptide sequences of the present invention can also be linked together using non-peptide cross-linkers (Pierce 2003-2004 Applications Handbook and Catalog, Chapter 6) or other scaffolds such as HPMA, polydextran, polysaccharides, ethylene-glycol, poly-ethylene-glycol, glycerol, sugars, and sugar alcohols (e.g., sorbitol, mannitol).

In one embodiment, recombinant ATGL is incorporated within liposomes for delivery across the cell membrane, or conjugated to lipophilic moieties. A wide variety of liposomes and liposome like particles are well known to those of skill in the art.

Alternatively, the recombinant ATGL can be expressed within the cell of a subject following introduction of a DNA encoding the protein, e.g., a nucleic acid encoding the recombinant ATGL functional protein (e.g. using a plasmid or viral vectors (e.g. AAV or lentiviral vectors) well known to those of skill in the art). In some embodiments, the nucleic acid comprises a nucleic acid sequence encoding a fusion protein comprising recombinant ATGL and a cell penetration peptide and/or target moiety.

Formulations and Administration

For administration to a subject, the compounds can be administered by any means known to those of skill in the art, e.g., orally, parenterally, subcutaneously, intravenously, intramuscularly, intraperitoneally, by intranasal instillation, or by application to mucous membranes, such as, that of the nose, throat, and bronchial tubes. One method for targeting the nervous system, such as spinal cord glia, is by intrathecal delivery. The targeted compound is released into the surrounding CSF and/or tissues and the released compound can penetrate into the spinal cord parenchyma, just after acute intrathecal injections. For a comprehensive review on drug delivery strategies, See Ho et al., Curr. Opin. Mol. Ther. (1999), 1:336-3443, Groothuis et al., J. Neuro Virol. (1997), 3:387-400; and January, Drug Delivery Systems: Technologies and Commercial Opportunities, Decision Resources, 1998.

The compounds can be administered alone or with suitable pharmaceutical carriers, and can be in solid or liquid form such as, tablets, capsules, powders, solutions, suspensions, or emulsions.

As used herein, the term "administered" refers to the placement of a compound described herein, into a subject by a method or route which results in at least partial localization of the compound at a desired site. A compound described herein can be administered by any appropriate route which results in effective treatment in the subject (e.g. a significant reduction in lipid accumulation within cells), i.e. administration results in delivery to a desired location in the subject where at least a portion of the composition delivered. Exemplary modes of administration include, but are not limited to, injection, infusion, instillation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion.

In one embodiment, the compounds are administered locally to heart muscle. For example, the compound may be delivered by catherization or by direct injection. Alternatively, a delivery vehicle may be loaded with the compound and directly applied to the heart. Delivery vehicles include but are not limited to drug-impregnated or coated releasing sheets, patches, matrix, hydrogel, foam, gel, cream, spray, microsphere, microcapsule, composite and ointment, or polymeric devices. In one embodiment, the compound is delivered locally to the heart by the use of targeted vehicles, e.g. liposomes, which are modified to that target cardiac myocytes.

The compounds can be formulated in pharmaceutically acceptable compositions which comprise a therapeutically-effective amount of the compound, formulated together with one or more pharmaceutically acceptable carriers (additives) and/or diluents. The compounds can be specially formulated for administration in solid or liquid form, including those adapted for the following: (1) oral administration, for example, drenches (aqueous or non-aqueous solutions or suspensions), lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally. Additionally, compounds can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 35 3,270,960.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

Pharmaceutically-acceptable antioxidants include, but are not limited to, (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lectithin, propyl gallate, alpha-tocopherol, and the like; and (3) metal chelating agents, such as citric acid, ethylenediamine tetraacetic acid (EDTA), sorbitol, tartaric acid, phosphoric acids, and the like.

"PEG" means an ethylene glycol polymer that contains about 20 to about 2000000 linked monomers, typically about 50-1000 linked monomers, usually about 100-300. Polyethylene glycols include PEGs containing various numbers of linked monomers, e.g., PEG20, PEG30, PEG40, PEG60, PEG80, PEG100, PEG115, PEG200, PEG300, PEG400, PEG500, PEG600, PEG1000, PEG1500, PEG2000, PEG3350, PEG4000, PEG4600, PEG5000, PEG6000, PEG8000, PEG11000, PEG12000, PEG2000000 and any mixtures thereof.

The compounds can be formulated in a gelatin capsule, in tablet form, dragee, syrup, suspension, topical cream, suppository, injectable solution, or kits for the preparation of syrups, suspension, topical cream, suppository or injectable solution just prior to use. Also, compounds can be included in composites, which facilitate its slow release into the blood stream, e.g., silicon disc, polymer beads.

The formulations can conveniently be presented in unit dosage form and may be prepared by any of the methods well known in the art of pharmacy. Techniques, excipients and formulations generally are found in, e.g., *Remington's Pharmaceutical Sciences*, Mack Publishing Co., Easton, Pa. 1985, 17th edition, Nema et al., *PDA J. Pharm. Sci. Tech.* 1997 51:166-171. Methods to make invention formulations include the step of bringing into association or contacting an ActRIIB compound with one or more excipients or carriers. In general, the formulations are prepared by uniformly and intimately bringing into association one or more compounds with liquid excipients or finely divided solid excipients or both, and then, if appropriate, shaping the product.

The preparative procedure may include the sterilization of the pharmaceutical preparations. The compounds may be mixed with auxiliary agents such as lubricants, preservatives, stabilizers, salts for influencing osmotic pressure, etc., which do not react deleteriously with the compounds.

Examples of injectable form include solutions, suspensions and emulsions. Injectable forms also include sterile powders for extemporaneous preparation of injectable solutions, suspensions or emulsions. The compounds of the present invention can be injected in association with a pharmaceutical carrier such as normal saline, physiological saline, bacteriostatic water, Cremophor™ EL (BASF, Parsippany, N.J.), phosphate buffered saline (PBS), Ringer's solution, dextrose solution, ethanol, polyol (e.g., glycerol, propylene glycol, and liquid polyethylene glycol), vegetable oils, and suitable mixtures thereof, and other aqueous carriers known in the art. Appropriate non-aqueous carriers may also be used and examples include fixed oils and ethyl oleate. In all cases, the composition must be sterile and should be fluid to the extent that easy syringability exists. It must be stable under the conditions of manufacture and storage and must be preserved against the contaminating action of microorganisms such as bacteria and fungi. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatinA suitable carrier is 5% dextrose in saline. Frequently, it is desirable to include additives in the carrier such as buffers and preservatives or other substances to enhance isotonicity and chemical stability.

In some embodiments, compounds can be administrated encapsulated within liposomes. The manufacture of such liposomes and insertion of molecules into such liposomes being well known in the art, for example, as described in U.S. Pat. No. 4,522,811. Liposomal suspensions (including liposomes targeted to particular cells, e.g., a muscle cell, liver cell, heart cell etc.) can also be used as pharmaceutically acceptable carriers.

In one embodiment, the compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc.

In the case of oral ingestion, excipients useful for solid preparations for oral administration are those generally used in the art, and the useful examples are excipients such as lactose, sucrose, sodium chloride, starches, calcium carbonate, kaolin, crystalline cellulose, methyl cellulose, glycerin, sodium alginate, gum arabic and the like, binders such as polyvinyl alcohol, polyvinyl ether, polyvinyl pyrrolidone, ethyl cellulose, gum arabic, shellac, sucrose, water, ethanol, propanol, carboxymethyl cellulose, potassium phosphate and the like, lubricants such as magnesium stearate, talc and the like, and further include additives such as usual known coloring agents, disintegrators such as alginic acid and Primogel™, and the like.

The compounds can be orally administered, for example, with an inert dilutent, or with an assimilable edible carrier, or they may be enclosed in hard or soft shell capsules, or they may be compressed into tablets, or they may be incorporated directly with the food of the diet. For oral therapeutic administration, these compounds may be incorporated with excipients and used in the form of tablets, capsules, elixirs, suspensions, syrups, and the like. Such compositions and preparations should contain at least 0.1% of compound. The percentage of the agent in these compositions may, of course, be varied and may conveniently be between about 2% to about 60% of the weight of the unit. The amount of compound in such therapeutically useful compositions is such that a suitable dosage will be obtained. Preferred compositions according to the present invention are prepared so that an oral dosage unit contains between about 100 and 2000 mg of compound.

Examples of bases useful for the formulation of suppositories are oleaginous bases such as cacao butter, polyethylene glycol, lanolin, fatty acid triglycerides, witepsol (trademark, Dynamite Nobel Co. Ltd.) and the like. Liquid preparations may be in the form of aqueous or oleaginous suspension, solution, syrup, elixir and the like, which can be prepared by a conventional way using additives.

The compositions can be given as a bolus dose, to maximize the circulating levels for the greatest length of time after the dose. Continuous infusion may also be used after the bolus dose.

The compounds can also be administrated directly to the airways in the form of an aerosol. For administration by inhalation, the compounds in solution or suspension can be delivered in the form of an aerosol spray from pressured container or dispenser which contains a suitable propellant, e.g., a gas such as carbon dioxide, or hydrocarbon propellant like propane, butane or isobutene. The compounds can also be administrated in a no-pressurized form such as in an atomizer or nebulizer.

The compounds can also be administered parenterally. Solutions or suspensions of these compounds can be prepared in water suitably mixed with a surfactant, such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

It may be advantageous to formulate oral or parenteral compositions in dosage unit form for ease of administration and uniformity of dosage. As used herein, "dosage unit" refers to physically discrete units suited as unitary dosages for the subject to be treated; each unit containing a predetermined quantity of compound calculated to produce the desired therapeutic effect in association with the required pharmaceutical carrier.

Administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the compounds are formulated into ointments, salves, gels, or creams as generally known in the art.

The compounds can be administered to a subject in combination with a pharmaceutically active agent. Exemplary pharmaceutically active compound include, but are not limited to, those found in *Harrison's Principles of Internal Medicine*, 13$^{th}$ Edition, Eds. T. R. Harrison et al. McGraw-Hill N.Y., NY; Physicians Desk Reference, 50$^{th}$ Edition, 1997, Oradell N.J., Medical Economics Co.; Pharmacological Basis of Therapeutics, 8$^{th}$ Edition, Goodman and Gilman, 1990; United States Pharmacopeia, The National Formulary, USP XII NF XVII, 1990, the complete contents of all of which are incorporated herein by reference. In some embodiments, the pharmaceutically active agent is selected from the group consisting of butyrates, valproic acid, hydroxyuirae and Riluzole.

The compound and the pharmaceutically active agent may be administered to the subject in the same pharmaceutical composition or in different pharmaceutical compositions (at the same time or at different times). In some embodiments, the pharmaceutically active compound is a The amount of compound which can be combined with a carrier material to produce a single dosage form will generally be that amount of the compound which produces a therapeutic effect. Generally out of one hundred percent, this amount will range from about 0.1% to 99% of compound, preferably from about 5% to about 70%, most preferably from 10% to about 30%.

The tablets, capsules, and the like may also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it may contain, in addition to materials of the above type, a liquid carrier, such as a fatty oil.

Various other materials may be present as coatings or to modify the physical form of the dosage unit. For instance, tablets may be coated with shellac, sugar, or both. A syrup may contain, in addition to the active ingredient, sucrose as a sweetening agent, methyl and propylparabens as preservatives, a dye, and flavoring such as cherry or orange flavor.

The pharmaceutical compositions can be included in a container, pack, or dispenser together with instructions for administration.

In some embodiments, the compounds of the invention are administered in conjunction with additional therapies known to be beneficial in the treatment of symptoms of the lipid/glycogen disorder to be treated.

As used herein, the term "therapeutically effective amount" means an amount of the compound which is effective to reduce the accumulation of lipid or glycogen within cells by a significant amount as compared to an untreated control. Determination of a therapeutically effective amount is well within the capability of those skilled in the art. In one embodiment the therapeutically effective amount is an amount capable of shifting cellular energy metabolism from fatty acid oxidation to glycolysis, methods for measuring this shift are described in the examples section. Generally, a therapeutically effective amount can vary with the subject's history, age, condition, sex, as well as the severity and type of the medical condition in the subject, and administration of other agents that inhibit pathological processes in neurodegenerative disorders.

Guidance regarding the efficacy and dosage which will deliver a therapeutically effective amount of a compound to treat the lipid/glycogen storage disorders described herein can be obtained from cell culture models and the adjusted in animal models (e.g. gene knock out models) of the disorders, which are well established in the art. Non-limiting examples of animal models of glygogen storage disorder are described in: Akman et al. Animal models of glycogen storage disorders *Prog Mol Biol Transl Sci.* 2011; 100:369-88; Agnes G. A. Generalized glycogen storage and cardiomegaly in a knockout mouse model of Pompe disease Human *Molecular Genetics,* 1998, Vol. 7, No. 1 53-62; West, J. Gross, Animal models of glycogen storage conditions. Their relation to human disease. *Med.* 1975 September; 123(3): 194-201; Specht et al. Glycogen Storage Disease Type Ia in Canines: A Model for Human Metabolic and Genetic Liver Disease *Journal of Biomedicine and Biotechnology,* 2011, Article ID 646257, 9 pages; Non-limiting examples of animal models of lipid storage disorder are described in, for example: Tybulewicz et al., Gaucher's disease from targeted disruption of the mouse Glucocerebrosidase gene. *Nature* 357:407-410; Kazunori Sango et al., Mouse models of Tay-Sachs and Sandhoff diseases differ in neurologic phenotype and ganglioside metabolism, *Nature Genetics,* 1995, 11, 170-176; Wasserstein & McGovern, Genetic basis of lipid disorders, *Future Lipidology,* 2001, 3(2); 189; and ATGL knock out animal model described herein, as well as others well established in the art. Toxicity and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions that exhibit large therapeutic indices, are preferred.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized.

The therapeutically effective dose can be estimated initially from cell culture assays. A dose may be formulated in animal models to achieve a circulating plasma concentration range that includes the IC50 (i.e., the concentration of the therapeutic which achieves a half-maximal inhibition of symptoms) as determined in cell culture. Levels in plasma may be measured, for example, by high performance liquid chromatography. The effects of any particular dosage can be monitored by a suitable bioassay. Examples of suitable bioassays include DNA replication assays, transcription based assays, GDF-8 binding assays, and immunological assays.

The dosage may be determined by a physician and adjusted, as necessary, to suit observed effects of the treatment. Generally, the compositions are administered so that compound is given at a dose from 1 µg/kg to 100 mg/kg, 1 µg/kg to 50 mg/kg, 1 µg/kg to 20 mg/kg, 1 µg/kg to 10 mg/kg, 1 µg/kg to 1 mg/kg, 100 µg/kg to 100 mg/kg, 100 µg/kg to 50 mg/kg, 100 µg/kg to 20 mg/kg, 100 µg/kg to 10 mg/kg, 100 µg/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. For antibody compounds, one preferred dosage is 0.1 mg/kg of body weight (generally 10 mg/kg to 20 mg/kg). If the antibody is to act in the brain, a dosage of 50 mg/kg to 100 mg/kg is usually appropriate.

With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment or make other alteration to treatment regimen. The dosing schedule can vary from once a week to daily depending on a number of clinical factors, such as the subject's sensitivity to the polypeptides. The desired dos can be administered at one time or divided into subdoses, e.g., 2-4 subdoses and administered over a period of time, e.g., at appropriate intervals through the day or other appropriate schedule. Such sub-doses can be administered as unit dosage forms. Examples of dosing schedules are administration once a week, twice a week, three times a week, daily, twice daily, three times daily or four or more times daily.

In one embodiment, recombinant ATGL is administered in conjunction with compounds that known to upregulate mannose-6-phosphate receptors (e.g. Dexamethasone).

The compound (e.g., in a composition) can be administered to a subject, e.g., a subject in need of treatment to reduce lipid accumulation in cells. The method can include evaluating a subject, e.g., to evaluate LPD, BMI, genetic analysis, or triglyceride levels in tissue samples or cells, to thereby identify a subject as having excess, or abnormal lipid deposition.

High Throughput Screen of Compounds

In another aspect of the invention a high throughput assay for screening of compounds or agents that reduce intracellular accumulation of lipid within cells is provided, the assay comprises: (a) contacting a test population of induced pluripotent stem cells (iPSC's) derived from a somatic cell that lacks expression of wild-type adipose triglyceride lipase (ATGL), or that comprises a mutation in PNPLA2 gene, with a test compound; (b) differentiating the cells of step (a) in the presence of the test compound; and (c) selecting a compound that decreases lipid accumulation within the cells as compared to a differentiated control population of induced pluripotent stem cells (iPSC's) that has not been contacted with a test compound. The control population is derived from the same somatic cell or somatic cell type as the test population.

The intracellular lipid accumulation phenotype of NLSD-M can be quantified using colorimetric lipid staining assays and thus represents a robust surrogate phenotype for the pleiotropic disease presentation found in both clinical NLSD-M and the ATGL-KO mouse model (Pinent et al., 2008; Haemmerle et al., 2006; Kobayashi, K. et al. 2008). Furthermore, these lipid staining assays can be readily implemented in a high throughput two-dimensional culture system to facilitate screening applications. Given that excess lipid accumulation is also the molecular basis for the pathology of NLSD-M, a screen for modulators of this phenotype may suggest useful therapeutic approaches for the disease.

In some embodiments, the somatic cell is from a subject (e.g. human) that has neutral lipid storage disease with myopathy (NLSD-M), i.e. the cell has a mutation in the PNPLA2 gene.

In some embodiments, the somatic cell is from an knock out animal that has had the PNLAP2 gene for adipose triglyceride lipase (ATGL) deleted from its genome, or is a cell with a mutation in the gene for ATGL (i.e. PNLAP2).

The somatic cells can be reprogrammed into induced pluripotent stem cells using means well known those of skill in the art. For example by the use of the Yamanaka factors (Oct3/4, Sox2, Klf4, c-Myc), as described in the Examples disclosed herein. Alternative methods known to those of skill in the art can be used, e.g. as described in International patent applications; WO2007/069666; WO2008/118820; WO2008/124133; WO2008/151058; WO2009/006997; and U.S. Patent Applications US2010/0062533; US2009/0227032; US2009/0068742; US2009/0047263; US2010/0015705; US2009/0081784; US2008/0233610; U.S. Pat. No. 7,615,374; U.S. patent application Ser. No. 12/595,041, EP2145000, CA2683056, AU8236629, Ser. No. 12/602,184, EP2164951, CA2688539, US2010/0105100; US2009/0324559, US2009/0304646, US2009/0299763, US2009/0191159, EP1970446, US2009/0047263, US2009/0068742, and 2009/0227032, the contents of which are incorporated herein in their entirety by reference. The IPSC's should be clonally expanded prior to initiating differentiation and subjecting the cells to the test compounds (or for example to DMSO for control). In vitro differentiation can be initiated by plating cells either as hanging-droplets (Wobus et al., 1991) or as a monolayer in feeder-free gelatin-coated welled plates (e.g. 96 wells) (Huang and Wu, 2010). Cells are then incubated in differentiation medium for the desired number of days prior to subsequent treatment with the test compounds. The iPSC's can be differentiated into any desired cell type (e.g. skeletal muscle cells, neuronal cells, or smooth muscle cells), protocols for differentiation of iPSC's are well known to those of skill in the art, e.g. as described in Kaichi et al. *Cardiovasc Res.* 2010 Nov. 1; 88(2):314-23; Bilousova et al. *Journal of Investigative Dermatology*, 2011, 131, 857-864; Fujiwara et al., *PloS One*, 2011, 6(2) (cardiac cells), e16734; Hu et al, Proc. Natl. Acad. Sci. U.S. A., 2010, 107(9): 4335-4340 (neuronal cells); Zhang et al., *Cell Stem Cell*, 2010, 8(1): 31-45 (smooth muscle cells), which are herein incorporated by reference in their entirety.

In one embodiment, the cells are differentiated into cardiac muscle cells by incubation in differentiation medium comprising IMDM, 15% FBS, 2 mM L-glutamine, 0.001% v/v/ monothioglycerol, 50 µg/ml ascorbic acid.

In some embodiments, the test compounds or agents are not added until after about 1 day, about 2, days, about 3 days, about 4 days, about 5 days, about 6 days, or more after differentiation is initiated.

After addition of the test compounds or agents, the cells may be cultured in the presence of differentiation medium for additional time, e.g. 1 day, 2 days, 3 days, 4 days, 5 days, 6 days, 7 days, 8 days or more, prior to assessing the amount of lipid accumulation, e.g. by the use of Oil Red O (ORO) staining.

As used herein, the term "test compound or agent" refers to compounds or agents and/or compositions of the same that are to be screened for their ability to modulate (e.g. inhibit or increase) accumulation of lipids within cells The test compounds or agents can be small molecules, peptides, antibodies, antibody fragments, peptidomimetics (e.g., peptoids), amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

In some embodiments, the test compound is a small molecule. As used herein, the term "small molecule" can refer to compounds that are "natural product-like," however, the term "small molecule" is not limited to "natural product-like" compounds. Rather, a small molecule is typically characterized in that it contains several carbon-carbon bonds, and has a molecular weight of less than 5000 Daltons (5 kD), preferably less than 3 kD, still more preferably less than 2 kD, and most preferably less than 1 kD. In some cases it is preferred that a small molecule have a molecular weight equal to or less than 700 Daltons.

Nucleic acid agents, include but are not limited to, antisense oligonucleotide, RNA interfering agents (e.g. siRNA, shRNA), ribozyme, aptamers, and decoy oligonucleotides. Methods of preparing such nucleic acids are known in the art and easily available to those skilled in the art.

In some embodiments, amino acid based molecules, such a peptides, oligopeptides and proteins, can be used in screen to identify lipid modulating agents.

In some embodiments, the test agent is an antibody. As used herein, the term "antibody" includes complete immunoglobulins, antigen binding fragments of immunoglobulins, as well as antigen binding proteins that comprise antigen-binding domains of immunoglobulins. Antigen binding fragments of immunoglobulins include, for example, Fab, Fab', F(ab')2, scFv and dAbs.

The number of possible test compounds and agents runs into millions. Methods for developing small molecule, polymeric and genome based libraries are described, for example, in Ding, et al. J. Am. Chem. Soc. 124: 1594-1596 (2002) and Lynn, et al., J. Am. Chem. Soc. 123: 8155-8156 (2001). Commercially available compound libraries can be obtained from, e.g., Sigma Aldrich (St. Louis, Mo.), ArQule (Woburn, Mass.), Panvera (Madison, Wis.), Vitas-M Lab (Moscoe, Russia), Biomol International (Plymouth, Mass.). These libraries can be screened using the screening devices and methods described herein. Chemical compound libraries such as those from NIH Roadmap, Molecular Libraries Screening Centers Network (MLSCN) can also be used. The libraries may consist of a plurality of stored chemicals/agents, each chemical/agent having associated information stored in a database with information such as the chemical structure, purity, quantity, and physiochemical characteristics of the compound.

Depending upon the particular embodiment being practiced, the test compounds or agents can be provided free in solution, or may be attached to a carrier. Additionally, for the methods described herein, test compounds or agents may be screened individually, or in groups. Group screening is particularly useful where hit rates for effective test compounds are expected to be low such that one would not expect more than one positive result for a given group.

In some embodiments, the test compound or agent decreases lipid accumulation by at least 5%, 10%, 20%, 30%, 40%, 50%, 50%, 70%, 80%, 90%, 1-fold, 1.1-fold, 1.5-fold, 2-fold, 3-fold, 4-fold, 5-fold Generally, compounds can be tested at any concentration that can inhibit lipid accumulation relative to a control over an appropriate time period. In some embodiments, compounds are tested at concentration in the range of about 0.1 nM to about 1000 mM. In some embodiments, the compound is tested in the range of about 0.1 µM to about 20 µM, about 0.1 µM to about 10 µM, or about 0.1 µM to about 5 µM. In one embodiment, compounds are tested at 1 µM.

DEFINITIONS

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

Other than in the operating examples, or where otherwise indicated, all numbers expressing quantities of ingredients or reaction conditions used herein should be understood as modified in all instances by the term "about." The term "about" when used in connection with percentages may mean±1%.

The singular terms "a," "an," and the include plural referents unless context clearly indicates otherwise. Similarly, the word or is intended to include and unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

As used herein "ATGL" refers to adipose triglyceride lipase enzyme (also known as desnutrin). ATGL is expressed in a variety of tissues, including cardiac and skeletal muscle (Lake et al., 2005; Pinent et al., 2008), and as it cleaves the first ester bond in triacylglycerol (TAG), it is the rate-limiting enzyme in the breakdown of intracellular TAG droplets to provide free fatty acid for cellular energy metabolism (Haemmerle et al., 2006). *Homo sapiens* ATGL mRNA (wt) is found at Accession AY894804.1 (GI:58759050) (SEQ ID NO: 1).

Homologues and variant protein and nucleic acids of *Homo sapiens* ATGL (protein and nucleic acid encoding ATGL) are encompassed in embodiments of the invention. For example Genbank Accession No.'s: JF809663.1; RefSeq (protein) ACT09361.1; ABS58651.1; AAW81962.1; ACT09362.1; ADA57171.1; ABW93560.2; ADX66713.2; ACO05728.1; ADP24694.1; ADP24691.1; ADP24690.1; ABV04327.1 etc. As used herein, "homologous", when used to describe a polynucleotide, indicates that two polynucleotides, or designated sequences thereof, when optimally aligned and compared, are identical, with appropriate nucleotide insertions or deletions, in at least 70% of the nucleotides, usually from about 75% to 99%, and more preferably at least about 98 to 99% of the nucleotides. The term "homolog" or "homologous" as used herein also refers to homology with respect to structure and/or function. With respect to sequence homology, sequences are homologs if they are at least 50%, at least 60 at least 70%, at least 80%, at least 90%, at least 95% identical, at least 97% identical, or at least 99% identical. The term "substantially homologous" refers to sequences that are at least 90%, at least 95% identical, at least 97% identical or at least 99% identical. Homologous sequences may be the same functional gene or protein in different species.

As used herein, "functional ATGL" refers to ATGL enzyme that is capable of cleaving the first ester bond in triacylglycerol (TAG) within cells. Methods for assessing ATGL enzyme activity are well known to those of skill in the art, e.g. as described in Zimmermann et al. *Science*: Vol. 306 no. 5700 pp. 1383-1386.

As used herein, "Non-functional ATGL" refers to ATGL enzyme that is not capable of cleaving the first ester bond in triacylglycerol (TAG) within cells, or to ATGL enzyme exhibiting ATGL activity that is only "partially functional" as compared to ATGL activity observed in normal cells, i.e. the ATGL enzyme shows significantly reduced activity as compared to normal wild-type ATGL enzyme. The term "non-functional" is also intended to include ATGL enzymes, that while having enzyme activity, can not traffic to the lipid droplets within cells to perform their enzymatic activity.

As used herein, the term "PNPLA2" refers to patatin-like phospholipase domain containing 2 (PNPLA2) gene (i.e. the gene encoding adipose triglyceride lipase (ATGL) mRNA), or refers to the ATGL mRNA sequence encoded by PNPLA2. In humans PNPLA2 is located on chromosome 11 at position 15.5. The nucleotide sequence for *Homo sapiens* PNPLA2 that is found on chromosome 11 an accessible at Accession: NG_023394.1 (e.g. GI:300863141) of GeneBank. *Homo sapiens* ATGL mRNA is found at Accession AY894804.1 (GI:58759050) (SEQ ID NO: 1).

As used herein, "loss of function PNPLA2 gene mutations" refers to mutations in the PNPLA2 gene that result in loss of expression of ATGL, or that result in the expression of a non-functional or partially functional ATGL enzyme. At least five mutations in the PNPLA2 gene have been found to cause neutral lipid storage disease with myopathy. Some of these mutations cause the enzyme to function abnormally. Other mutations prevent the enzyme from ever reaching lipid droplets, so it is unable to interact with triglycerides. Non-limiting examples of loss of function PNPLA2 gene mutations include, but are not limited to, those described in Fischer et al. The gene encoding adipose triglyceride lipase (PNLPLA2) is mutated in neutral lipid storage disease with myopathy, *Nature Genetics* 39, 28-30 (2007); and in Hirano et al. Triglyceride Deposit Cardiomyovasculopathy, *N Engl. J. Med.*, 3549 (22):2396-2398 (2008), herein incorporated by reference in their entirety.

As used herein, the term "modulate" means to cause or facilitate a qualitative or quantitative change, alteration, or modification in lipid accumulation within cells. Without such change may be an increase or decrease in lipid accumulation. The term "modulator" refers to any molecule or compound that causes or facilitates a qualitative or quantitative change in lipid accumulation within cells.

As used herein, a "subject" means a human or animal. Usually the animal is a vertebrate such as a primate, rodent, domestic animal or game animal. In certain embodiments, the subject is a mammal, e.g., a primate, e.g., a human. The terms, "patient" and "subject" are used interchangeably herein.

The terms "decrease", "reduced", "reduction", "decrease" or "inhibit" are all used herein generally to mean a decrease by a statistically significant amount. In some embodiments, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90%.

The terms "increased", "increase" as used herein generally mean an increase by a statically significant amount. In some embodiments, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means a two standard deviation (2SD) below or above a reference measurement. The term refers to statistical evidence that there is a difference. It is defined as the probability of making a decision to reject the null hypothesis when the null hypothesis is actually true. The decision is often made using the p-value.

As used herein, an "RNA interference molecule" refers to a compound which interferes with or inhibits expression of a target gene or genomic sequence by RNA interference (RNAi). Such RNA interfering agents include, but are not limited to, nucleic acid molecules including RNA molecules which are homologous to the target gene or genomic sequence, or a fragment thereof, short interfering RNA (siRNA), short hairpin or small hairpin RNA (shRNA), microRNA (miRNA) and small molecules which interfere with or inhibit expression of a target gene by RNA interference (RNAi).

The term "polynucleotide" is used herein interchangeably with "nucleic acid" to indicate a polymer of nucleosides. Typically a polynucleotide of this invention is composed of nucleosides that are naturally found in DNA or RNA (e.g., adenosine, thymidine, guanosine, cytidine, uridine, deoxyadenosine, deoxythymidine, deoxyguanosine, and deoxycytidine) joined by phosphodiester bonds. However the term encompasses molecules comprising nucleosides or nucleoside analogs containing chemically or biologically modified bases, modified backbones, etc., whether or not found in naturally occurring nucleic acids, and such molecules may be preferred for certain applications. Where this application refers to a polynucleotide it is understood that both DNA, RNA, and in each case both single- and double-stranded forms (and complements of each single-stranded molecule) are provided. "Polynucleotide sequence" as used herein can refer to the polynucleotide material itself and/or to the sequence information (e.g. The succession of letters used as abbreviations for bases) that biochemically characterizes a specific nucleic acid. A polynucleotide sequence presented herein is presented in a 5' to 3' direction unless otherwise indicated.

The nucleic acid molecules that inhibit lipid accumulation can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. Proc. Natl. Acad. Sci. USA 91:3054-3057, 1994). The pharmaceutical preparation of the gene therapy vector can include the gene therapy vector in an acceptable dilutent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The terms "polypeptide" as used herein refers to a polymer of amino acids. The terms "protein" and "polypeptide" are used interchangeably herein. A peptide is a relatively short polypeptide, typically between about 2 and 60 amino acids in length. Polypeptides used herein typically contain amino acids such as the 20 L-amino acids that are most commonly found in proteins. However, other amino acids and/or amino acid analogs known in the art can be used. One or more of the amino acids in a polypeptide may be modified, for example, by the addition of a chemical entity such as a carbohydrate group, a phosphate group, a fatty acid group, a linker for conjugation, functionalization, etc. . . . A polypeptide that has a nonpolypeptide moiety covalently or noncovalently associated therewith is still considered a "polypeptide". Exemplary modifications include glycosylation and palmitoylation. Polypeptides may be purified from natural sources, produced using recombinant DNA technology, synthesized through chemical means such as conventional solid phase peptide synthesis, etc. The term "polypeptide sequence" or "amino acid sequence" as used herein can refer to the polypeptide material itself and/or to the sequence information (e.g., the succession of letters or three letter codes used as abbreviations for amino acid names) that biochemically characterizes a polypeptide. A polypeptide sequence presented herein is presented in an N-terminal to C-terminal direction unless otherwise indicated.

The term "identity" as used herein refers to the extent to which the sequence of two or more nucleic acids or polypeptides is the same. The percent identity between a sequence of interest and a second sequence over a window of evaluation, e.g., over the length of the sequence of interest, may be computed by aligning the sequences, determining the number of residues (nucleotides or amino acids) within the window of evaluation that are opposite an identical residue allowing the introduction of gaps to maximize identity, dividing by the total number of residues of the sequence of interest or the second sequence (whichever is greater) that fall within the window, and multiplying by 100. When computing the number of identical residues needed to achieve a particular percent identity, fractions are to be rounded to the nearest whole number. Percent identity can be calculated with the use of a variety of computer programs known in the art. For example, computer programs such as BLAST2, BLASTN, BLASTP, Gapped BLAST, etc., generate alignments and provide percent identity between sequences of interest. The algorithm of Karlin and Altschul (Karlin and Altschul, Proc. Natl. Acad. Sci. USA 87:22264-2268, 1990) modified as in Karlin and Altschul, Proc. Natl. Acad. Sci. USA 90:5873-5877, 1993 is incorporated into the NBLAST and XBLAST programs of Altschul et al. (Altschul, et al., J. Mol. Biol. 215:403-410, 1990). To obtain gapped alignments for comparison purposes, Gapped BLAST is utilized as described in Altschul et al. (Altschul, et al. Nucleic Acids Res. 25: 3389-3402, 1997). When utilizing BLAST and Gapped BLAST programs, the default parameters of the respective programs may be used. A PAM250 or BLOSUM62 matrix may be used. Software for performing BLAST analyses is publicly available through the National Center for Biotechnology Information (NCBI). See the Web site having URL www.ncbi.nlm.nih.gov for these programs. In a specific embodiment, percent identity is calculated using BLAST2 with default parameters as provided by the NCBI.

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

To the extent not already indicated, it will be understood by those of ordinary skill in the art that any one of the various embodiments herein described and illustrated may be further modified to incorporate features shown in any of the other embodiments disclosed herein.

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

EXAMPLES

Example 1

High Throughput Screening for Small Molecules that Modulate Intracellular Lipid Accumulation Induced pluripotent stem cells (iPSCs) hold great promise for a wide variety of biomedical applications, including regenerative medicine (Lengner, 2010), cell therapy for genetic diseases (Raya et al., 2009), and drug discovery (Gunaseeli et al., 2010). While significant progress has been made in the generation of pluripotent stem cell models to study physiological and disease processes of major organs such as the heart (Laflamme et al., 2007; van Laake et al., 2007; Moretti et al., 2010), central nervous system (Wernig et al., 2008; Dimos et al., 2008; Tsuji et al., 2010), blood (Rideout et. al, 2002; Grigoriadis et al., 2010), and pancreas (Chen et al., 2009; Kobayashi, T. et al., 2010), the successful application of iPSC-based disease modeling in high throughput drug discovery has not yet been reported. The development of iPSCs as a drug discovery platform presents a number of challenges, including the need to control lineage-specific differentiation, recapitulate complex disease phenotypes in vitro, and develop robust, quantitative measurements of these phenotypes in order to assess efficacy of drug treatment. In light of these considerations, we chose to examine neutral lipid storage disease, myopathy subtype (NLSD-M), based on several features that render it particularly amenable for iPSC¬based drug screening.

In the present study, we developed both a murine and a human iPSC model of NLSD-M for high throughput applications using fibroblasts derived from ATGL-KO mice and NLSD-M patients. Differentiation of murine ATGL-KO and human NLSD-M iPSCs recapitulated the intracellular lipid accumulation phenotype observed in vivo in humans and mice. From the mouse model, We established a robust, high throughput in vitro differentiation and small molecule screening platform, using a quantitative colorimetric assay for intracellular lipid to evaluate for reversal of the disease phenotype. Examination of the top-scoring screen hits in secondary assays confirmed their lipid-lowering effects in both mouse ATGL-KO and human NLSD-M iPSCs. Further mechanistic studies revealed that treatment with compounds that shift cellular energy metabolism from fatty acid oxidation to glycolysis led to reduced lipid accumulation. Thus, in addition to identifying pharmacological modulators of a disease phenotype, the use of an iPSC-based high throughput drug screening platform has also allowed us to explore the dysregulated metabolic processes underlying the disease. Our demonstration here of a successful application of high throughput drug screening using differentiated murine iPSCs and secondary validation using human iPSC, provides a paradigm for the utility of iPSC-based disease modeling in drug screening and novel disease pathway discovery.

Generation and Characterization of a TGL-KO and WT iPSC Lines

Figure 1:
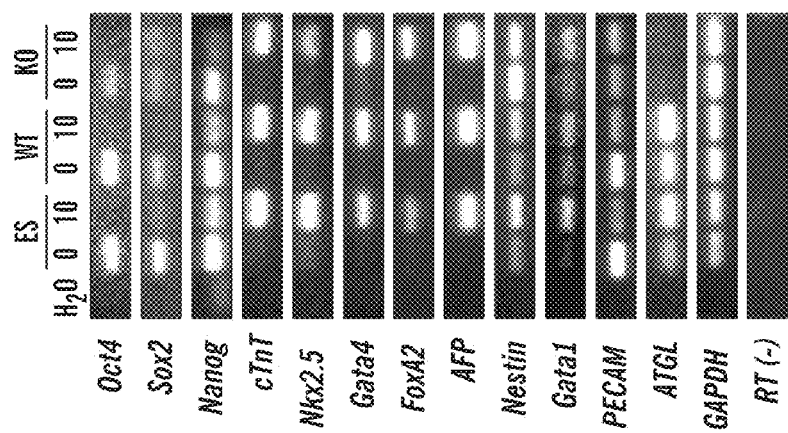
FIG. 1 shows a gel of RT-PCR products for pluripotency and germ-layer markers in WT and KO iPSCs and ES cells on days 0 and 10 of differentiation.
Figure 2C:
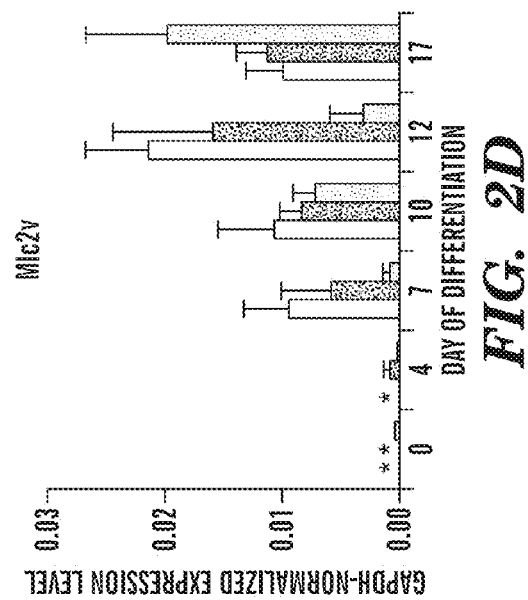
Figure 2E:
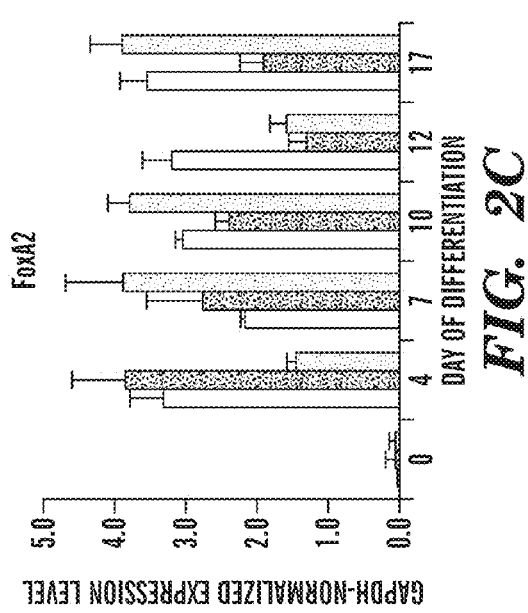
Figure 2D:
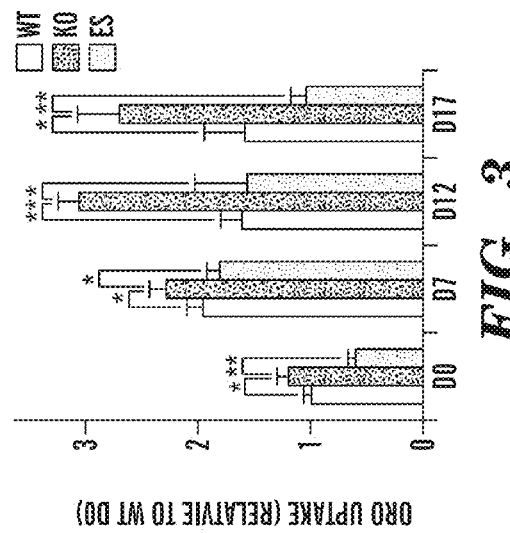

We introduced the pluripotency reprogramming factors (Oct4, Sox2, Klf4, and c-Myc) (Takahashi and Yamanaka, 2006) into embryonic fibroblasts derived from ATGL-KO and WT littermates (Haemmerle et al., 2006). When maintained in an undifferentiated state, the resulting KO and WT iPSC lines expressed pluripotency markers such as SSEA-1, Nanog, Sox2, and alkaline phosphatase at levels similar to an established undifferentiated ES cell line ((data not shown). Upon in vitro differentiation, both KO and WT iPSCs and the control ES cell line downregulated their expression of pluripotency genes (Oct4, Sox2, and Nanog) and upregulated their expression of cardiac (cTnT, NRkx2.5, Gata4), hematopoietic (Gata1), endodermal (FoxA2, AFP), and neuronal markers (Nestin) (FIG. 1). We confirmed that the KO iPSC line did not express ATGL throughout the course of differentiation (FIG. 1). Quantitative PCR confirmed the proper time-dependent expression patterns of Oct4, Brachyury, Mlc-2v, FoxA2, and Nestin in differentiating KO and WT iPSCs and control ES cells (FIG. 2), and immunocytochemistry for the expression of germ-layer markers in Nestin, AFP, and cTNT in the WT, KO iPSCs and ES cells at day 12 of differentiation confirmed the presence of cardiac troponin T—(cTnT), □-fetoprotein (AFP), and Nestin-positive cells in differentiated ATGL-KO and WT IPSC and control ES cell cultures. These data indicate that the loss of ATGL does not affect germ layer differentiation, as expected given the viable ATGL-KO mouse phenotype observed in vivo (Haemmerle et al., 2006).

Figure 3:
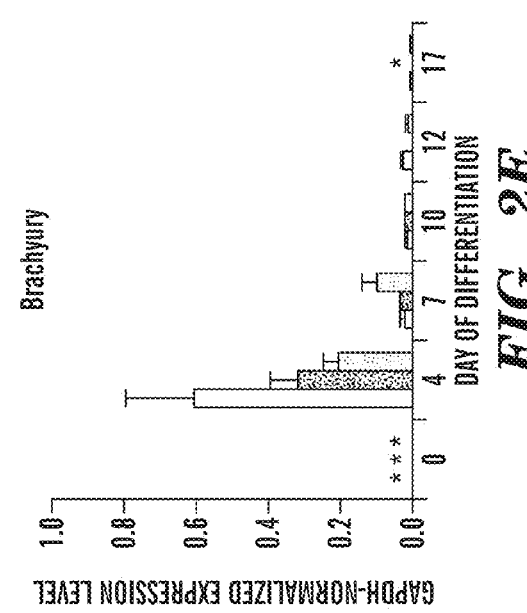
FIG. 3 depicts a bar graph of quantitative analysis of ORO levels in each cell line during in vitro differentiation; i.e. WT IPSC, ATGL-KO IPSCs, and control ES cells. Data are plotted as mean normalized ORO±s.d., n=3 (*P<0.05, **P<0.005, student's t-test), relative to the normalized ORO levels of WT day 0 samples. ATGL-KO iPSCs recapitulate intracellular lipid accumulation phenotype of ATGL¬KO mice.
Figure 4D:
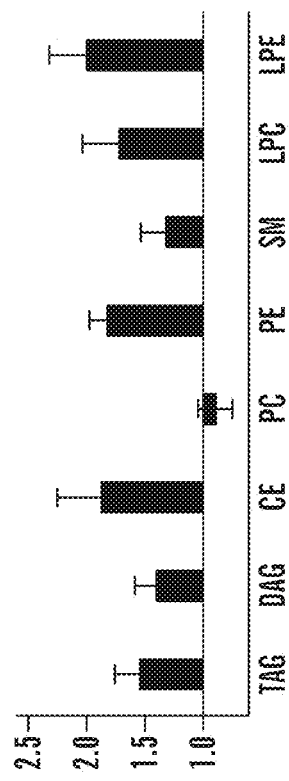

We measured the levels of intracellular lipid accumulation using Oil Red O (ORO) staining in differentiating ATGL-KO, WT, and ES cells at days 0, 7, 12, and 17. While all three cell lines exhibited a progressive increase in ORO accumulation, by day 12 this increase was significantly more pronounced in ATGL-KO iPSCs than in WT iPSCs or ES cells (data not shown). The ratio of normalized ORO levels between KO and WT iPSCs increased from 1.2±0.1-fold (mean±s.d., P<0.05) at day 0 to 1.8±0.3-fold (P<0.05) at day 17 of differentiation (FIG. 3). A detailed composition profile of the accumulated lipids in differentiated ATGL-KO iPSCs was obtained using a high sensitivity, targeted LC-MS-based analysis (Rhee et al. 2010), and it confirmed that most TAG species were elevated in KO cells compared to WT cells (FIG. 4a). Interestingly, cholesteryl esters were also elevated, while phosphatidylcholine species were decreased (FIGS. 4b-d).

Given the massive lipid accumulation in the ATGL-KO mouse heart (Haemmerle et al., 2006), we examined whether cardiomyocytes and smooth muscle cells derived from ATGL-KO iPSCs display preferential lipid uptake. Immunofluorescent and ORO co-staining of differentiated KO iPSCs for cTnT-positive cardiomyocytes revealed enhanced lipid accumulation in these cells compared with similar cells derived from WT iPSCs or ES cells (data not shown). Lipid accumulation was somewhat less pronounced in KO iPSC-derived smooth muscle cells compared to that in cardiomyocytes (data not shown), consistent with the reported in vivo phenotype of the KO mouse (Haemmerle et al., 2006). ORO staining in cTnT- and SM-MHC-positive ATGL-WT iPSC- and ES-derived cells. Immuno-costaining for ORO and cTnT and SM-MHC in ATGL-WT iPSCs and control ES cells was performed at day 12 of differentiation.

Figure 5A:
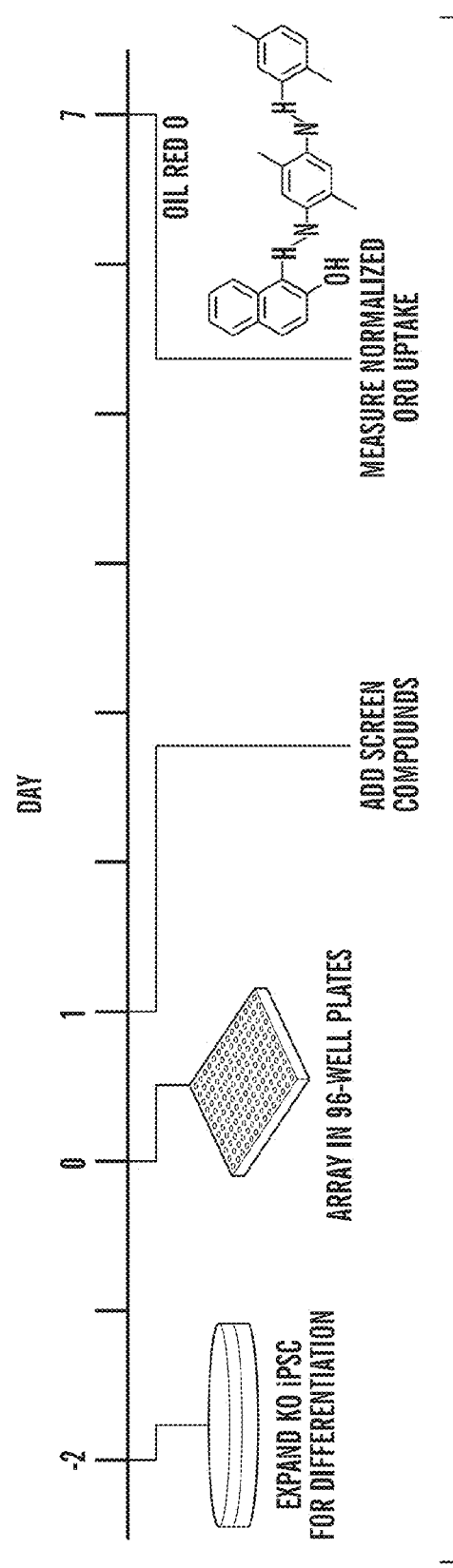
FIGS. 5a-5c show graphic illustrations of the high throughput screening for small molecule regulators of the lipid accumulation phenotype in ATGL-KO iPSCs.
Figures 5B, 5C:
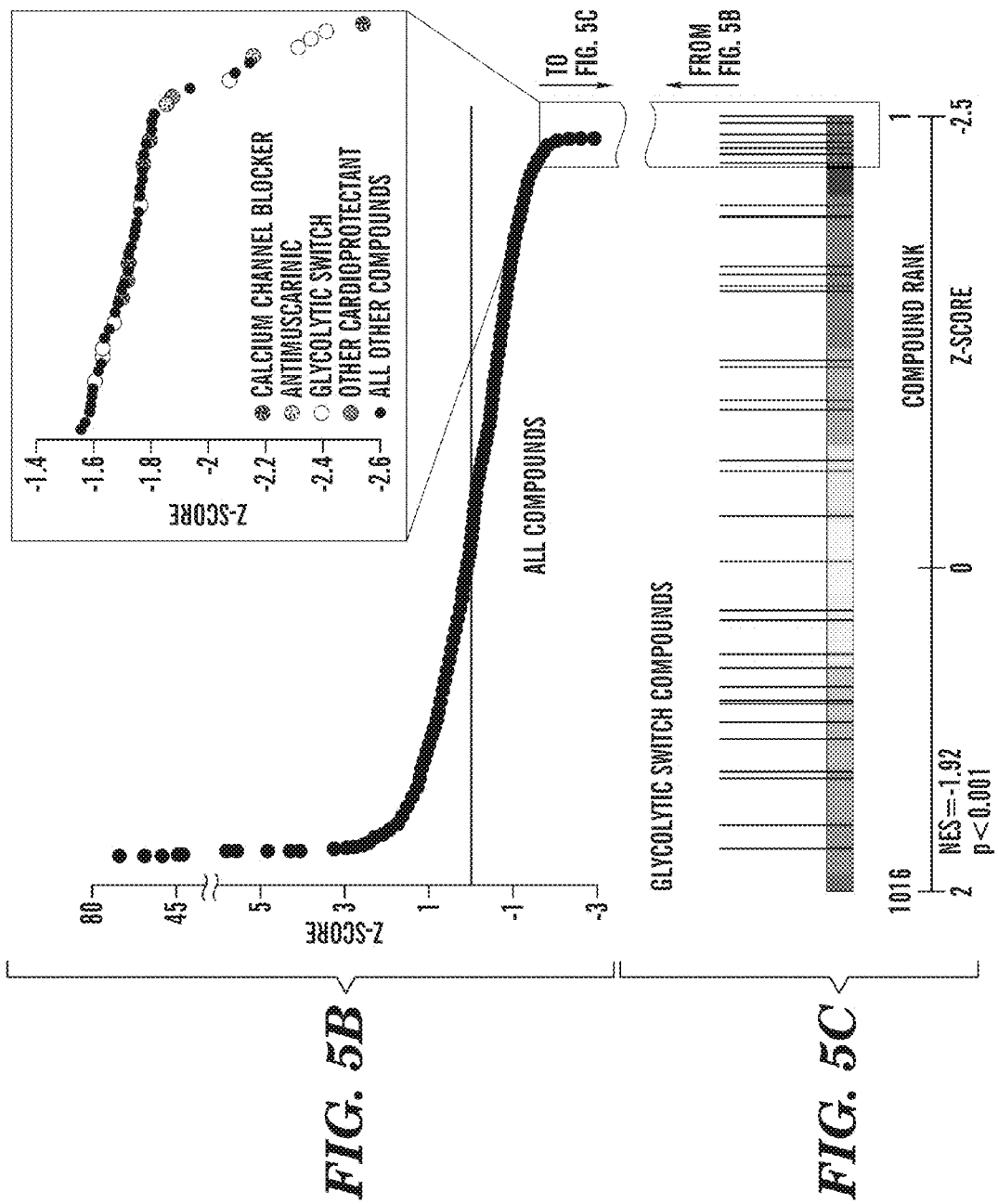

High throughput screening for small molecules that modulate intracellular lipid accumulation The ATGL-KO iPSCs were then adapted to 96-well plate cultures to facilitate screening of the Prestwick□ collection of 1118 structurally diverse, off-patent drugs, many with established bioavailability and safety profiles in humans. ATGL-KO iPSCs were differentiated in the presence of candidate compounds for 7 days, after which ORO uptake was measured in each sample and normalized against cell number, as assessed by a resazurin cell viability assay (screen protocol depicted in FIG. 5a). Individual compound results were converted to Z-scores to reflect their performances relative to DMSO-treated control cells (see Table 1). Compounds that induced a decrease in lipid accumulation while preserving cell viability resulted in negative Z-scores. Inspection of the compounds with the most negative Z-scores (the top-scoring hits) revealed several drugs that shift cellular metabolism from mitochondrial respiration towards glycolysis (either by activating glycolysis or inhibiting oxidative respiration) (Gohil et al., 2010), as well as a number of calcium channel blockers, anticholinergics of the muscarinic type, and other cardioprotectants such as antihypertensives and vasodilators (FIG. 5b).

Compounds that shift energy metabolism away from oxidative respiration towards glycolysis ("glycolytic switch inducers") may mitigate the demand for fatty acids as an energy source, which in turn could reduce the drive for fatty acid uptake or synthesis and decrease intracellular lipid accumulation. To examine this hypothesis in a more systematic manner, we tested whether compounds with potential glycolytic switch activity are statistically enriched among the top hits in our screen. We identified a set of 41 potential glycolytic switch inducers from the screening library using a previously reported data set of such compounds (Gohil et al., 2010) (Table 2). We then calculated a weighted Kolmogorov-Smirnov-like statistic, the normalized enrichment score (NES), that reflects the extent to which members of this compound set are statistically enriched among compounds with the most negative Z-scores (Shaw et al., 2010, Subramanian et al., 2005). The NES statistic revealed enrichment of glycolytic switch inducers among the top-scoring compounds; five out of the top 10 screen hits and 9 out of the top 50 were members of the glycolytic switch compound set ($p<0.001$ by random permutation of compound sets) (FIG. 5c and Table 2).

The lipid-lowering effect of seven of the top-scoring hits are listed in Table 3.

TABLE 3

Validated screen hits

| Compound | Screen concentration (M) | Known or putative functions[45] |
|---|---|---|
| Fendiline hydrochloride | 15 | $Ca^{2+}$-channel blocker; coronary vasodilator |
| Vinpocetine | 15 | Phosphodiesterase inhibitor; vasodilator; glycolytic switch[27] |
| Mefloquine hydrochloride | 12 | Antimalarial; glycolytic switch[27] |
| Perhexiline maleate glycolytic | 12 | CPT-1 inhibitor[25]; vasodilator; switch[27] |
| Dicyclomine hydrochloride | 15 | Anticholinergic (muscarinic)[35] |
| Tomatine | 5 | Antifungal |
| Clidinium bromide | 15 | Anticholinergic (muscarinic) |

Figure 6A:
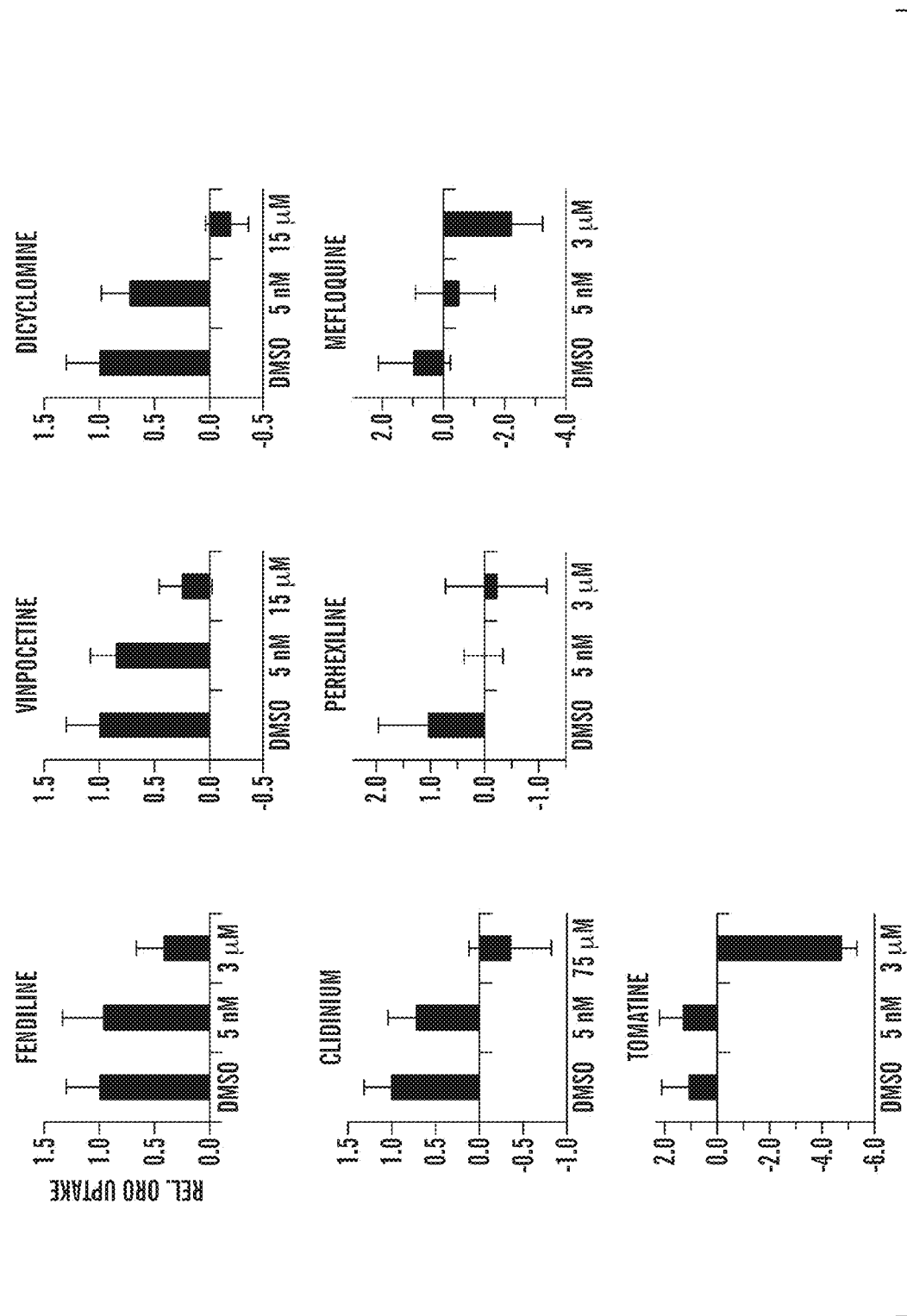
FIGS. 6a-6c depict that top-scoring screen hits demonstrate robust lipid-lowering effect in ATGL-KO iPSCs.
Figure 6B:
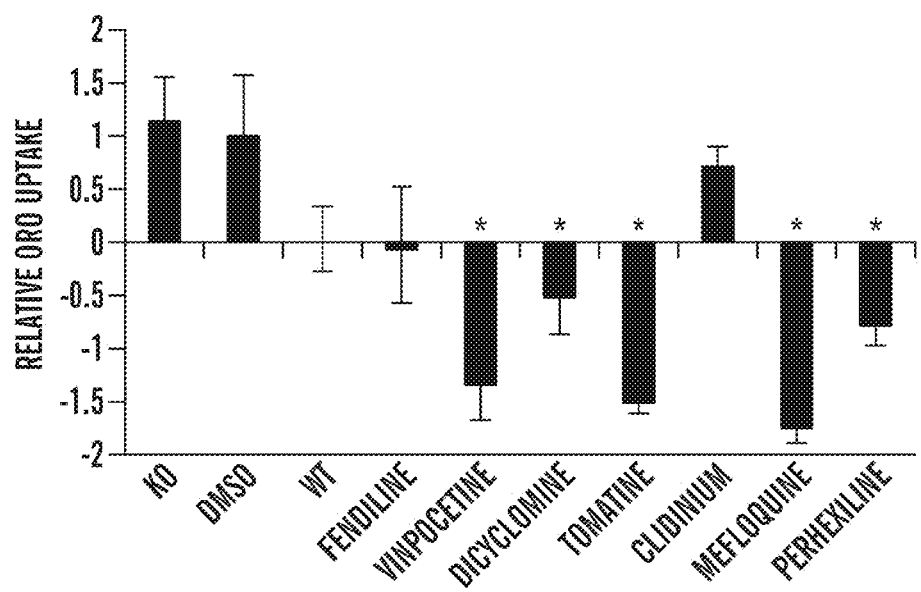
Figure 6C:
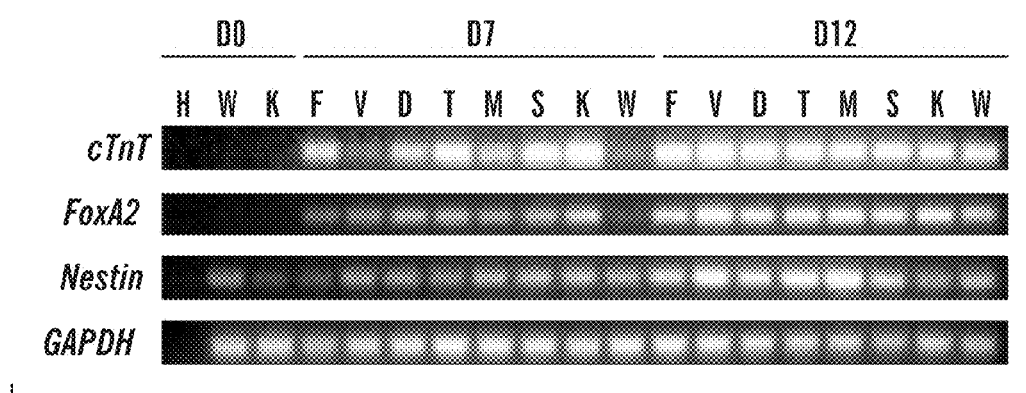

These represent a variety of functional classes, and were confirmed in secondary assays demonstrating dose-dependent effects (FIG. 6a) as well as sustained drug efficacy in older, lineage-committed ATGL-KO iPSCs (FIG. 6b). We confirmed that drug treatment did not alter the course of differentiation of the iPSCs, as assessed by the expression levels of differentiation markers (FIG. 6c).

Figure 8D:
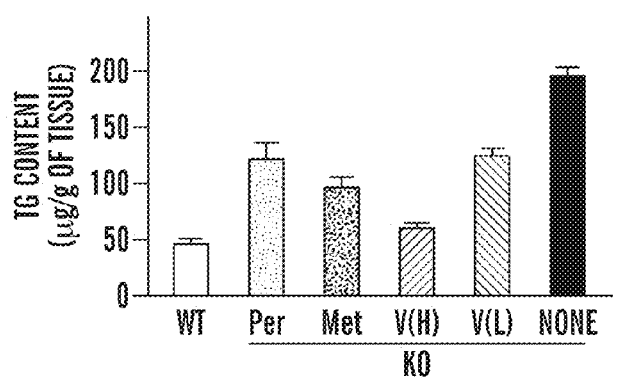
Figure 8E:
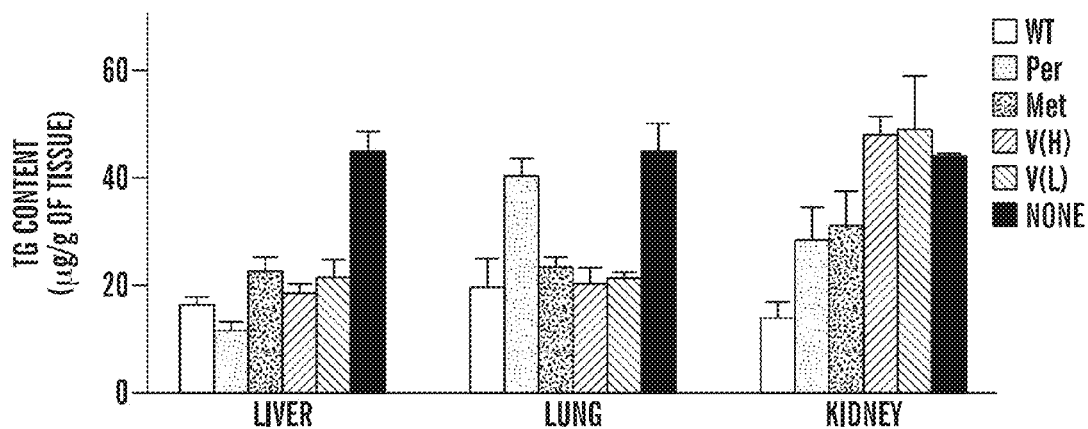
Figure 8F:
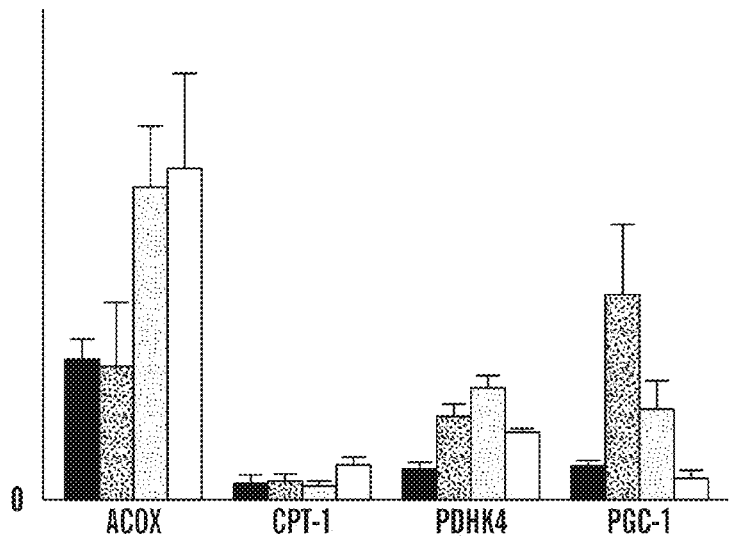

In Vivo Validation of Top Screening Candidates to Reduce Intracellular Lipid Accumulation While the ability of top screen hits to reduce intracellular lipid accumulation in vitro is encouraging, the demonstration of an effect in vivo is essential in order to translate these findings into a clinically relevant setting. We designed an 18-week observer-blinded placebo-controlled study treating both wild type and ATGL-KO mice with mefloquine, perhexyline, and high and low doses of vinpocetin starting from 3 weeks after birth. We assess the survival of each animal throughout the entire treatment course. We also measured the cardiac function of each animal before treatment and at 10 and 14 weeks of age. As shown in FIG. 8a, significant prolongation in overall survival (~30% increase) was observed in all treatment groups compared with untreated ATGL-KO animals. This was corroborated by the echocardiographic improvements in cardiac function in mefloquine and perhexyline treated animals at 14 weeks of age (data not shown and FIG. 8b). In addition, the hearts of ATGL-KO mice exhibit significant increase in triglyceride content compared with wild type mice (~190 µg/g vs 45 µg/g) (FIG. 8c). Remarkably, treatment with mefloquine, perhexyline, and vinpocetin all led to reduction in the overall triglyceride content in the heart (FIG. 8d and as determined by ORO staining of frozen heart sections, data not shown). The effect of these drugs on triglyceride content was observed variably in other tissues such as liver, lung, and kidney (FIG. 8e). While these drugs were able to elicit a similar reduction in triglyceride content, they appear to do so by recruiting genes involved in distinct pathways. (FIG. 8f)

Reduction of Intracellular Lipid Accumulation in NLSD-M Human iPSCs

Figure 9A:
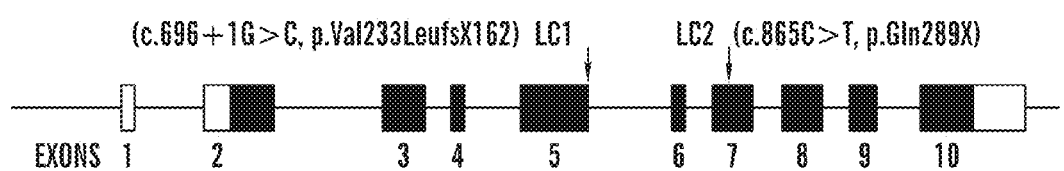
FIGS. 9a-9b show graphs of the effect of drug candidates on differentiated NLSD-M human iPSCs.

The ability of top drug screen hits to reduce intracellular lipid accumulation in the hearts of ATGL-KO mice supports the utility of these drugs to regulate metabolic pathways in patients with NLSD-M. However, the limited access to such patient population (currently only 17 patients world-wide carrying such diagnosis) makes it very challenging to validate the utility of the drug screen hits. As a proof-of-principal of the ability of our drug hits to reduced intracellular lipid accumulation in human NLSD-M, we generated human iPSC from two Japanese patients (LC1 and LC2) with NLSD-M (also known as Triglyceride Cardiomyovasculopathy (TGCV) in Japan) and demonstrated the ability of their skin fibroblasts to fully reprogram into iPSCs. that express high levels of pluripotency genes such as Nanog, Oct4, and Sox2 by immunofluresence microscopy (FIG. 9a, data not shown). Injection of these human iPSCs into immunedeficient mice resulted in the formation of teratoma that contains cells from all three germ layers as determined using hematoxylin and eosin staining (data not shown). The staining showed thae presence of chondrocyte, boney spicule, squamous cells, ciliated columnar epithelium, and neurons in teratoma (data not shown). Upon in vitro differentiation, these iPSC lines formed beating cardiomyocytes that stained positive for sarcomeric actinin usinf anti-sarcomeric actinin antibody and co-staining with oil Red O (data not shown).

Figure 9B:
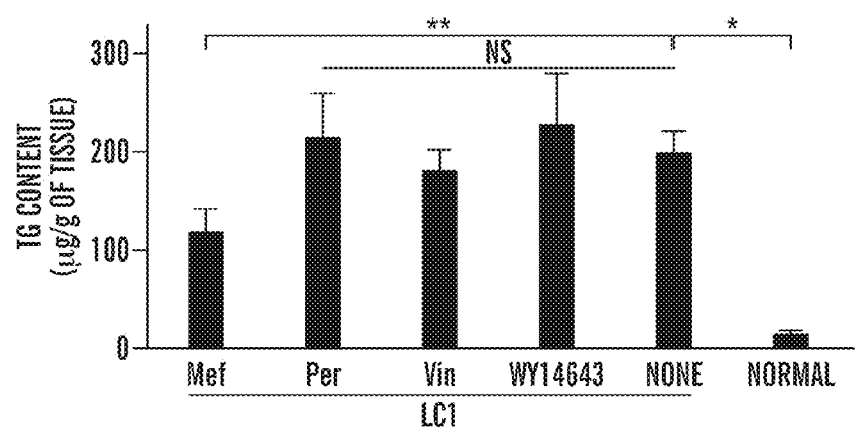

Remarkable, most of the cardiomyocytes from NLSD-M iPSCs co-stained with Oil Red O while none of the cardiomyocytes from control normal iPSCs show Oil Red O positive staining (data not shown). Given the faithful recapitulation of the lipid accumulation phenotype, we assess whether our top drug hits can reduce lipid accumulation in human cells in vitro. As shown in FIG. 9b, treatment with mefloquine appears to significantly reduce intracellular lipid content.

Metabolic and Energetic Effects of Screen Positives on a TGL-KO and WY iPSCs

Figure 7A:
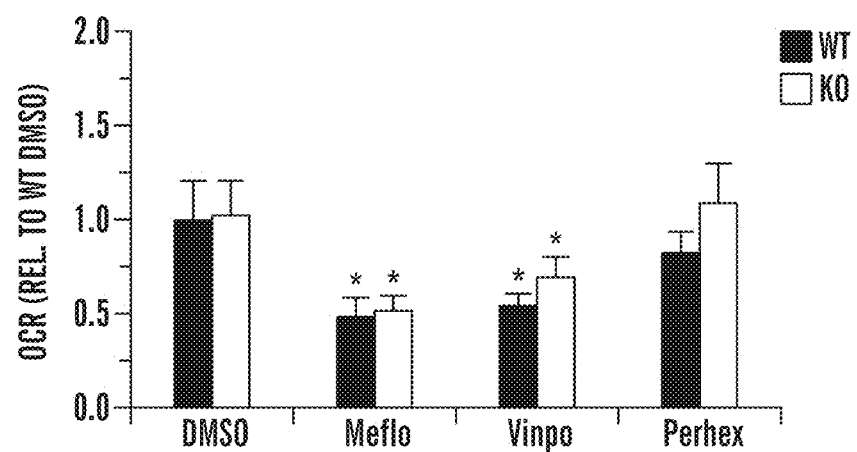
FIGS. 7a-7g depict that glycolytic switch inducers modulate the metabolic profile of WT and KO iPSCs. Measurement of (FIG. 7a) oxygen consumption rate (OCR) and (FIG. 7b) extracellular acidification rate (ECAR) in WT and KO iPSCs at day 10 of differentiation following compound pre-treatment for 16 h. Data are expressed as mean±s.d. (n=10 samples, with 3 measurements each) relative to DMSO-treated WT cells. ($*P<0.001$, student's t-test between compound-treated and DMSO¬treated cells of same type. $**P<0.001$, student's t-test between DMSO-treated WT and KO cells). Measurement of OCAR/ECAR ratios for drug-treated (FIG. 7c) WT and (FIG. 7d) KO iPSCs following treatment carbonyl cyanide m-chlorophenyl hydrazone (CCCP), at the time indicated (arrow). Antimycin, an electron transport chain inhibitor, was added to each well at the end of the assay to verify that mitochondrial function was intact in drug-treated cells. A schematic model of ATGL¬mediated lipid metabolism in shown for (FIG. 7e) WT cells, (FIG. 7f) KO cells, and (FIG. 7g) drug-treated KO cells.
Figure 7B:
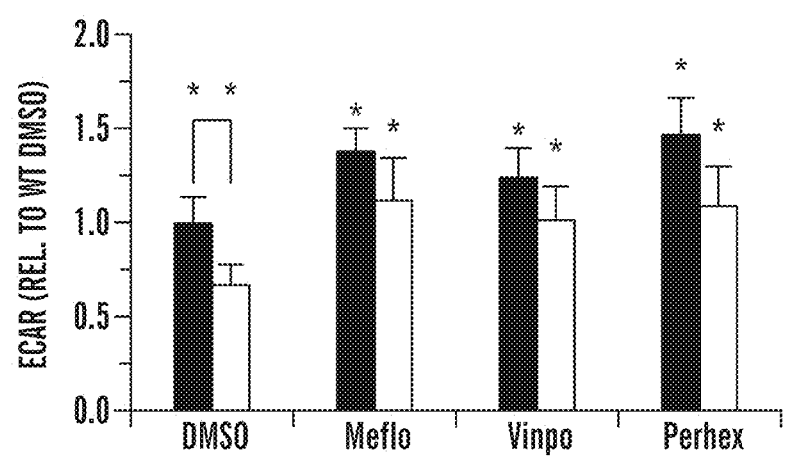

While the energy starvation and cold intolerance phenotypes of ATGL-KO mice are consistent with the decreased availability of fatty acids as an energy source, the compensatory mechanism by which KO cells generate the necessary amount of ATP for growth and survival remains unclear (Haemmerle et al., 2006). The limited availability of intracellular free fatty acid as an energy source in ATGL-KO mice suggests that these animals have adapted to greater glucose utilization. In accordance with this hypothesis, ATGL-KO mice exhibit increased glucose tolerance and uptake (Haemmerle et al., 2006). To study this adaptation at the cellular level, we measured oxygen consumption rates (OCR) and extracellular acidification rates (ECAR) on day 10 of ATGL-KO and WT iPSC differentiation. OCR and ECAR measurements reflect cellular oxidative respiration and glycolytic lactic acid production, respectively. Interestingly, we observed that WT and KO iPSCs exhibited similar OCRs (FIG. 7a), suggesting similar rates of oxidative respiration, while the ECAR of KO cells was reduced by $34\pm15\%$ (mean±s.d., $P<0.001$; FIG. 7b). This suggests either an overall decrease in glycolysis in KO iPSCs, an unlikely event given the energy starvation phenotype, or more probably, an increased adaptation to glucose and the utilization of pyruvate in the TCA cycle at the expense of its conversion to lactic acid.

We next investigated whether the top-scoring compounds with reported glycolytic switch properties could in fact modulate the OCR and ECAR of differentiated WT and KO iPSCs. We pre-treated day 9 differentiated cells overnight with mefloquine, vinpocetine, and perhexyline at their screen concentrations (Table 3) and measured the changes in OCR and ECAR. As expected, treatment with each of these compounds resulted in a decreased OCR and an increased ECAR in both WT and KO iPSCs (FIGS. 7a and 7b), suggesting that the cells have decreased rates of TCA cycle and electron transport chain utilization and increased rates of glycolysis and lactic acid production. Interestingly, perhexyline, an inhibitor of carnitine palmitoyltransferase 1 (CPT-1), which regulates mitochondrial fatty acid import/utilization via the TCA cycle (Kennedy et al., 1996), had a smaller impact on OCR in KO cells compared to WT cells. This is consistent with the increased adaptation to glucose in ATGL-KO cells.

Figure 7C:
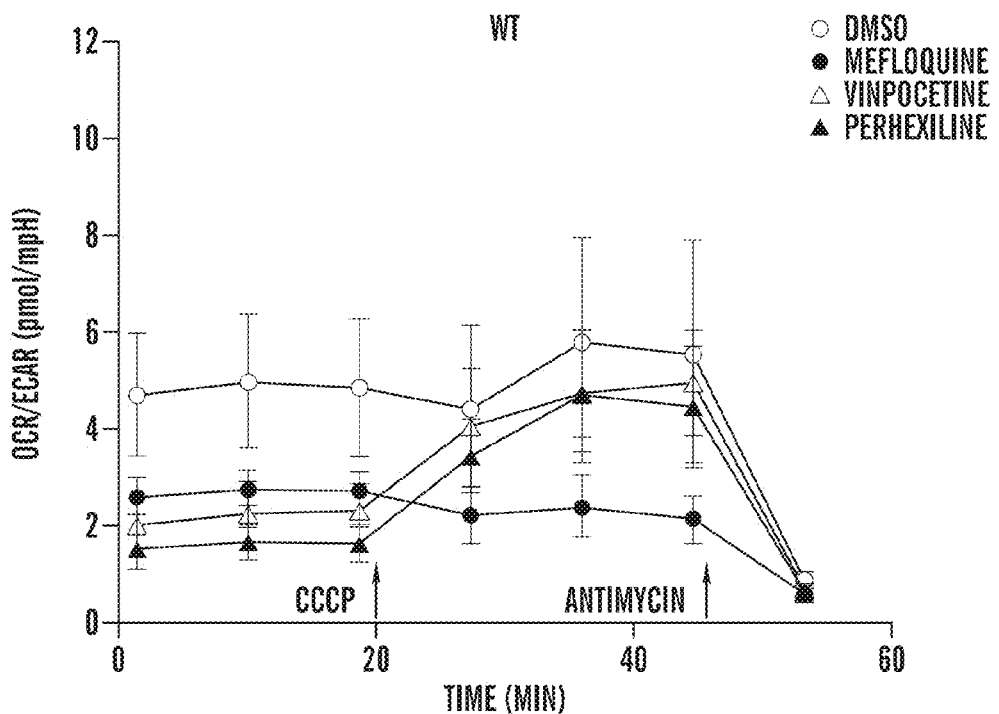
Figure 7D:
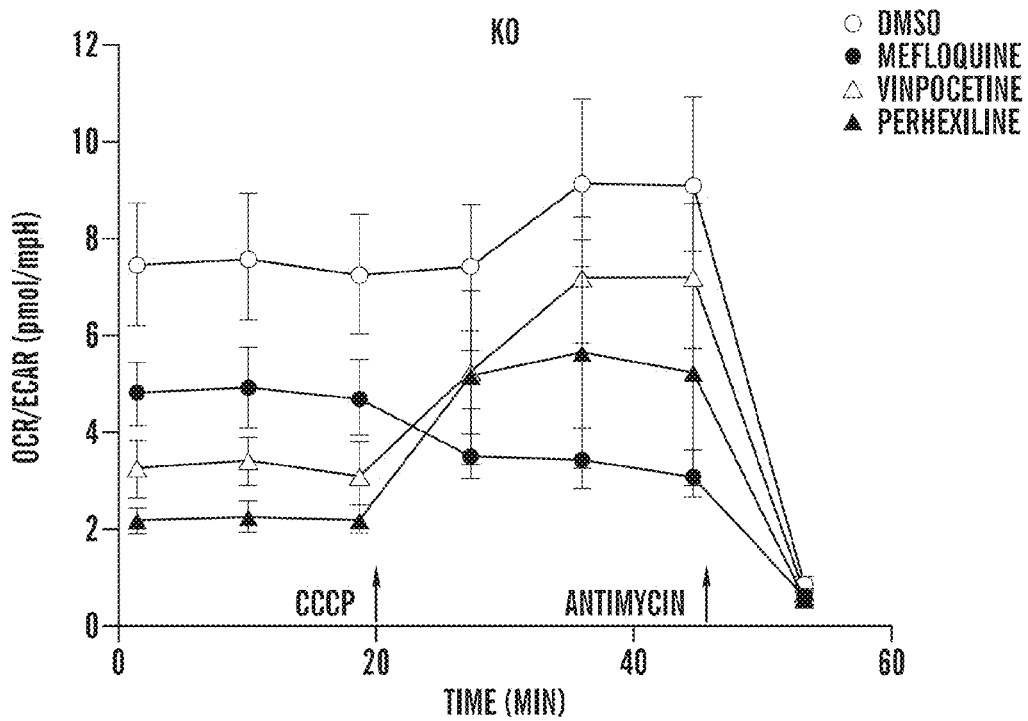

To determine whether the glycolytic switch inducers work through common or distinct mechanisms, we next examined how the responses of ATGL-KO and WT cells to challenge with carbonyl cyanide m-chlorophenyl hydrazone (CCCP) differed upon pre-treatment with glycolytic switch inducers. CCCP is an uncoupler of the mitochondrial hydrogen gradient that induces maximal cellular oxidative respiration (Goldsby et al., 1963). Interestingly, in both WT and KO differentiated iPSCs that had been pre-treated with mefloquine and vinpocetine, the addition of CCCP increased the ratio of OCAR/ECAR (FIGS. 7c and 7d), similar to the response observed in DMSO control cells. This was due entirely to an increase in OCAR, as the ECAR levels remained relatively unchanged (data not shown). However, treatment with perhexyline resulted in no increase in the OCR/ECAR ratio (FIGS. 7c and 7d), consistent with the direct inhibition of mitochondrial fatty oxidation by perhexyline. These data suggest that mefloquine and vinpocetine regulate cell metabolism via a different mechanism(s) from that of perhexyline.

Recent advances in cellular reprogramming biology have enabled the generation of patient-specific iPSCs for in vitro disease modeling. In principle, the availability of these cell lines should facilitate therapeutic screening for molecules or pathways that modulate the development of the disease phenotype (Gunaseeli et al., 2010; Ebert and Svendsen, 2010; Kiskinis and Eggan, 2010). Patient-specific iPSCs for Fanconi's anemia (Raya et al., 2009), long QT syndrome (Moretti et al., 2010), ALS (Dimos et al., 2008), familial dysautonomia (Lee et al., 2009), Type 1 diabetes (Maehr et al., 2009), and LEOPARD syndrome (Carvajal-Vergara et al., 2010) have all been recently reported. These studies demonstrate the ability of in vitro differentiated iPSCs to recapitulate relevant aspects of a disease phenotype; however, to the best of our knowledge, no report has yet been made of their use in high throughput screens to identify new molecules or pathways that regulate the disease process.

Figure 7E:
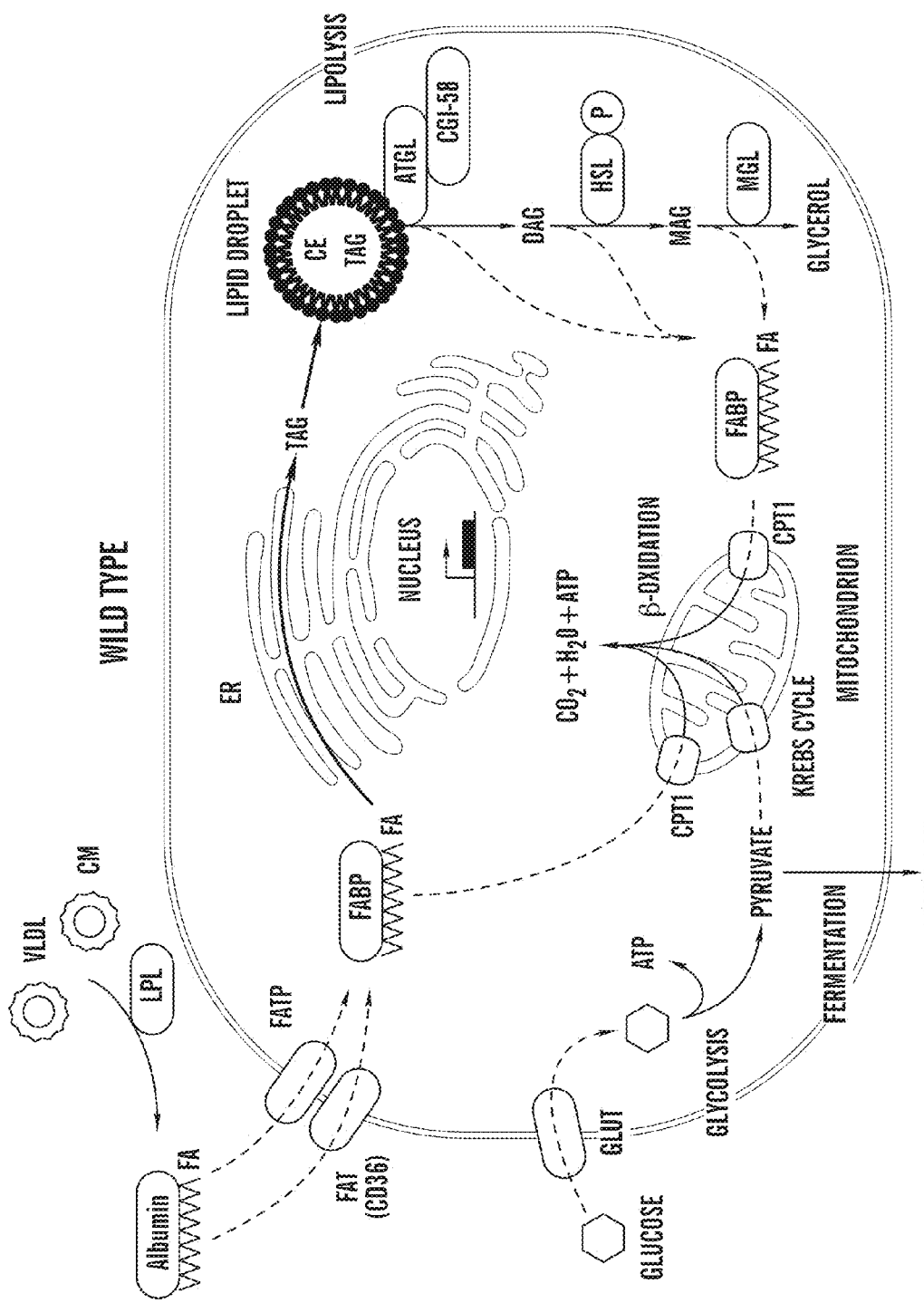
Figure 7F:
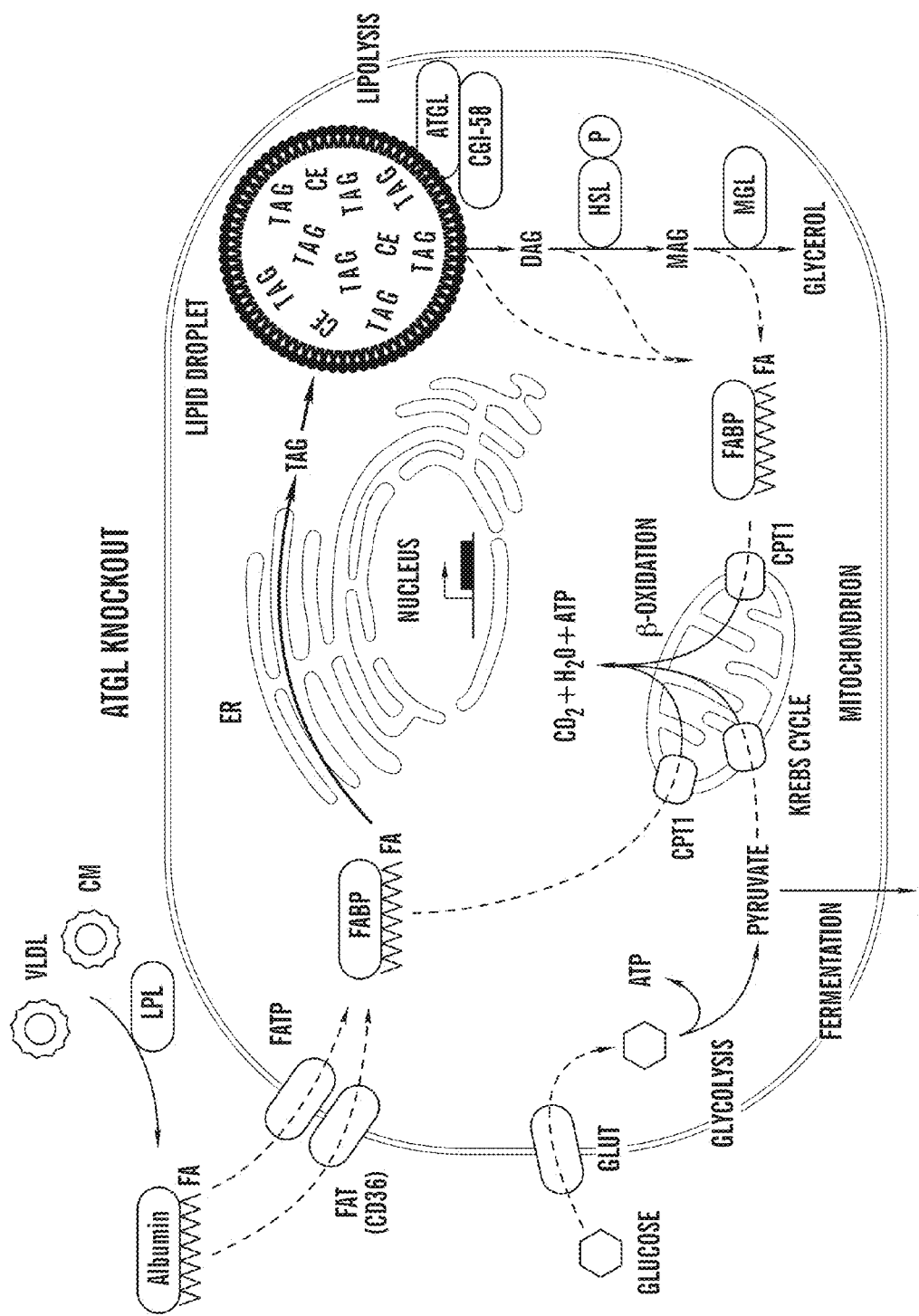
Figure 7G:
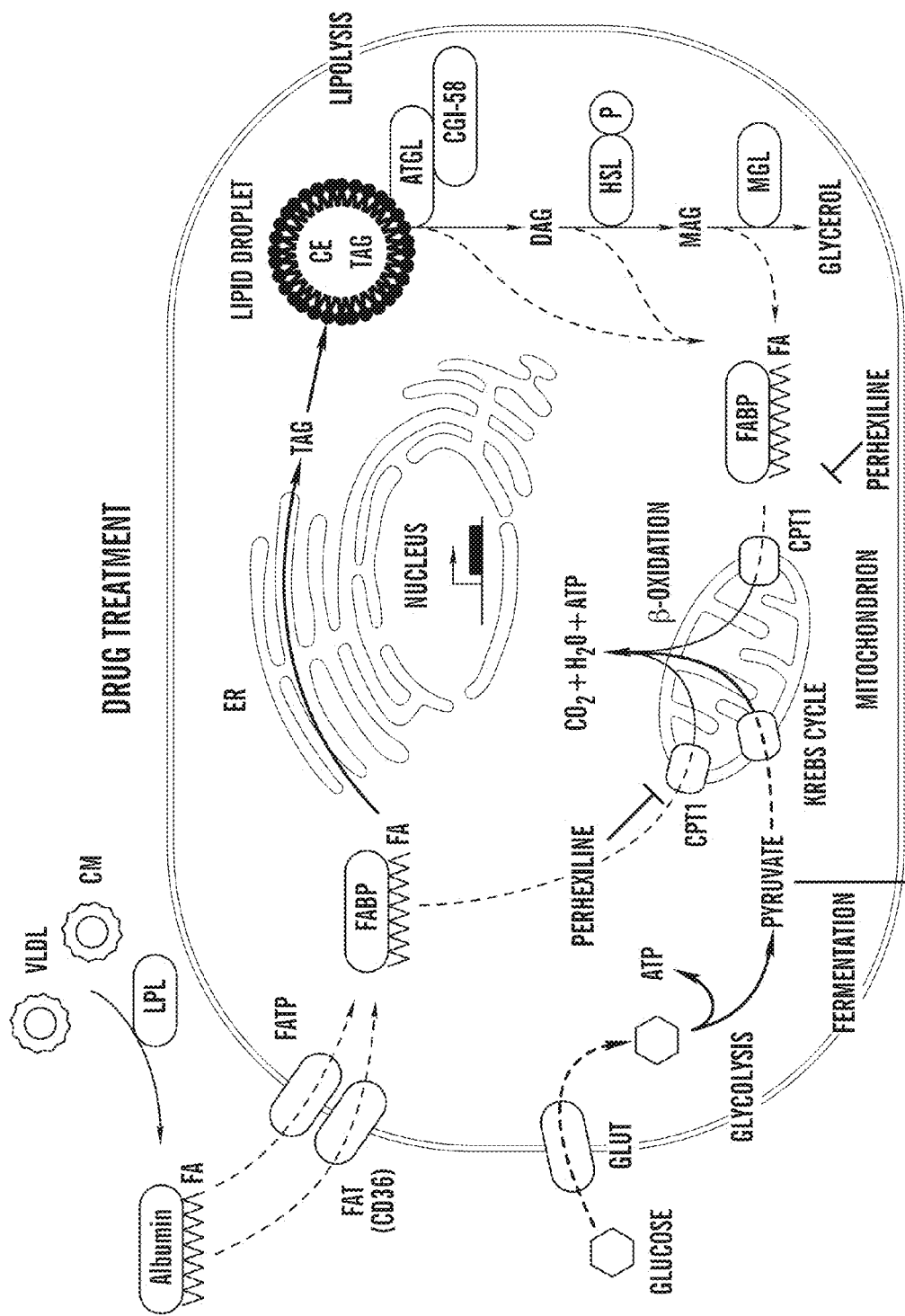

We have demonstrated here that the intracellular lipid accumulation phenotype of ATGL¬KO mice and patients with NLSD-M was faithfully recapitulated in murine ATGL-KO and human NLSD-M iPSCs, allowing for the development of an effective screening platform. From screening murine ATGL-KO iPSCs, we identified a number of mechanistically distinct families of compounds that reduce intracellular lipid accumulation. These results support the use of iPSC disease modeling not only as a platform for drug screening, but also as a tool for novel disease or physiological pathway discovery. In the case of reversing the ATGL-KO phenotype in vitro, the most effective compounds have purported activities that either directly or indirectly impact cellular energy metabolism. For example, we found that glycolytic switch inducers, the most commonly represented class of compounds among the top hits, consistently reduced lipid accumulation in ATGL-KO iPSCs. This was achieved by increased rates of glycolysis and decreased rates of oxidative respiration. These results suggest that a regulatory feedback loop may link energy substrate usage to the import or synthesis of fatty acids and thus influence overall accumulation of lipid droplets in cells (see model in FIG. 7e-f). In WT cells, this process is finely balanced against TAG hydrolysis to meet the metabolic demands of the cell. In ATGL-KO cells, impaired hydrolysis of TAG results in TAG accumulation in lipid droplets and decreases the supply of fatty acid substrate for β-oxidation, resulting in a compensatory increased in oxidation of glucose-derived pyruvate in the mitochondria. In drug-treated ATGL-KO cells, the modulation of energy metabolism towards increased glycolysis reduces the demand for fatty acid uptake and hence reduces overall lipid accumulation.

This drug-mediated change in cellular metabolism is analogous to a reversion to a fetal metabolic profile in the ATGL-KO cells, whereby glycolysis and lactate production are upregulated and fatty acid uptake and oxidation are downregulated (Girard et al. 1992). This metabolic profile may be responsible for protecting ATGL-KO mice from accumulating intracellular lipid droplets until after birth, when aerobic metabolism becomes predominant. This would explain the postnatal disease phenotype observed in the KO mice and progressive increase in lipid accumulation in the hearts of KO mice (FIG. 8c), despite the loss of ATGL function throughout embryonic development (Haemmerle et al., 2006). Reverting to the fetal metabolic profile via pharmaceutical intervention should thus be protective in these mice, and potentially, in human NLSD-M patients. In support of this, we show that iPSCs derived from patients with NLSD-M exhibit intracellular lipid accumulation in cardiomyocytes (data not shown) and this phenotype can be reversed by treatment with one of the top hits from our high throughput screen. The continued exploration of the role of metabolic programming and its molecular basis in NLSD-M will be the focus of future studies using murine and human NLSD-M iPSC models, as the clear ability of glycolytic switch inducers to reduce lipid accumulation can be used for both in vitro and in vivo therapeutic use.

Our investigation of NLSD-M using murine ATGL-KO and human iPSCs as in vitro disease models has provided novel insights into the metabolic disturbances that take place in the absence of ATGL and their recovery in the presence of small molecule modulators. In the process, we have taken care to address an important caveat to the use of iPSCs as disease models, namely, that differentiated cells derived from iPSCs are largely immature and hence may fail to display the expected disease phenotype. The fact that ATGL-KO mice do not exhibit increased lipid accumulation in tissues until after birth initially raised concerns that we would observe minimal or no disease phenotype in differentiated KO iPSCs (Haemmerle et al., 2006). Surprisingly, we found that the KO iPSCs developed robust lipid accumulation in a differentiation-dependent fashion over a relatively short period of time. This suggests that diseases that manifest clinically well after birth (i.e. in the adolescent or adult years) may still be amenable to in vitro modeling via iPSC technology. Ultimately, the most important confirmation of the utility of iPSCs for novel drug and pathway discovery will be to show that the findings identified in vitro and in animal models are relevant to treatment of human patients. The current demonstration of the feasibility of a high throughput small molecule screen utilizing disease-specific iPSCs is an important first step towards accomplishing this goal.

Experimental Procedures

Murine and Human iPSC Generation and Maintenance

Unless otherwise specified, all cell cultures were maintained in 37° C., 5% CO2 incubators. Using a previously described tetracycline-inducible lentiviral expression system (Stadtfeld et al., 2008), we generated murine ATGL-KO and WT iPSC lines from embryonic fibroblasts derived from ATGL¬KO and WT littermates (Haemmerle et al., 2006), respectively. Briefly, ATGL-KO and WT fibroblasts were infected with tet-inducible lentiviruses containing mouse cDNA sequences for c-Myc (T58A mutant), Klf4, Oct4, and Sox2, as well as a lentivirus expressing reverse tetracycline transactivator (rtTA). Forty-eight hours post-infection, the cells were plated onto a feeder layer of mitomycin c-treated mouse embryonic fibroblasts (mMEF) in ES cell medium (high-glucose DMEM, 15% FBS, 2 mM L-glutamine, 100 µM NEAA100 µM 2-mercaptoethanol, 103 units/mL LIF). Doxycycline (1 µg/mL) was added and subsequently refreshed every 2-3 days to induce viral expression. Colonies with ES cell-like morphology were observed at approximately 10 to 14 days post-infection and were manually selected for clonal expansion.

For the generation of human NLSD-M iPSCs, we infected skin fibroblasts from two patients (LC1 and LC2) with NLSD-M and one normal individual for two day with polycystronic lentiviruses containing human cDNA sequences for Oct4, Sox2, Klf4, and c-Myc. The infected cells were plated onto mMEF in embryonic fibroblasts medium followed by mTeSR® medium. Colonies with ES cell-like morphology were observed approximately 10 to 14 days post-infection and were manually selected for clonal expansion.

In Vitro iPSC Differentiation

The ATGL-KO and WT iPSC lines and a control ES cell line (NK5-2) (Wu, S. M. et al., 2006) were maintained according to a previously described protocol (Huang and Wu, 2010). In vitro differentiation was initiated by plating cells either as hanging-droplets (Wobus et al., 1991) or as a monolayer in feeder-free gelatin-coated 96-well plates (Huang and Wu, 2010). The cells were then incubated in differentiation medium (IMDM, 15% FBS, 2 mM L-glutamine, 0.001% v/v monothioglycerol, 50 µg/mL ascorbic acid) for the desired number of days prior to subsequent assays.

Gene Expression Analysis

Cells were solubilized in Trizol reagent (Invitrogen) and total RNA was purified using the RNeasy Mini Kit (Qiagen). cDNA was synthesized using iScript (BioRad), and RT-PCR was performed using GoTaq polymerase (Promega). Quantitative PCR was performed using USB SYBR-Green master mix (Affymetrix) on an EP Realplex thermal cycler (Eppendorf). Gene expression was calculated using the standard curve method and normalized against the expression of GAPDH in the same sample. A list of primers used is given in Table 4.

TABLE 4

Gene expression primers

| Target | Forward (5' to 3') | Reverse (5' to 3') |
|---|---|---|
| Oct4 | CTCCCGAGGAGTCCCAGGACAT (SEQ ID NO: 2) | GATGGTGGTCTGGCTGAACACCT (SEQ ID NO: 3) |
| Sox2 | GCGGAGTGGAAACTTTTGTCC (SEQ ID NO: 4) | CGGGAAGCGTGTACTTATCCTT (SEQ ID NO: 5) |
| Nanog | CAAGGGTCTGCTACTGAGATGCTCTG (SEQ ID NO: 6) | TTTTGTTTGGGACTGGTAGAAGAATCAG (SEQ ID NO: 7) |
| cTnT | CAGAGGAGGCCAACGTAGAAG (SEQ ID NO: 8) | CTCCATCGGGGATCTTGGGT (SEQ ID NO: 9) |
| Nkx2.5 | GACAAAGCCGAGACGGATGG (SEQ ID NO: 10) | CTGTCGCTTGCACTTGTAGC (SEQ ID NO: 11) |
| Gata4 | CTGTCATCTCACTATGGGCA SEQ ID NO: 12) | CCAAGTCCGAGCAGGAATTT (SEQ ID NO: 13) |
| FoxA2 | CCCTACGCCAACATGAACTCG (SEQ ID NO: 14) | GTTCTGCCGGTAGAAAGGGA (SEQ ID NO: 15) |
| AFP | AACTCTGGCGATGGGTGTTTA | ACACTGATGTCTTTCCACTCCA |

TABLE 4-continued

Gene expression primers

| Target | Forward (5' to 3') | Reverse (5' to 3') |
|---|---|---|
|  | (SEQ ID NO: 16) | (SEQ ID NO: 17) |
| Nestin | CCCTGAAGTCGAGGAGCTG (SEQ ID NO: 18) | CTGCTGCACCTCTAAGCGA (SEQ ID NO: 19) |
| Gata1 | ACTGGCCTACTACAGAGAAGC (SEQ ID NO: 20) | GTAGAGTGCCGTCTTGCCATA (SEQ ID NO: 21) |
| PECAM | CTGCCAGTCCGAAAATGGAAC (SEQ ID NO: 22) | CTTCATCCACCGGGGCTATC (SEQ ID NO: 23) |
| Mlc2v | GCCAAGAAGCGGATAGAAGG (SEQ ID NO: 24) | CTGTGGTTCAGGGCTCAGTC (SEQ ID NO: 25) |
| Brachyury | GCTGGATTACATGGTCCCAAG (SEQ ID NO: 26) | GGCACTTCAGAAATCGGAGGG (SEQ ID NO: 27) |
| GAPDH | AGGTCGGTGTGAACGGATTTG (SEQ ID NO: 28) | TGTAGACCATGTAGTTGAGGTCA (SEQ ID NO: 29) |
| ATGL | CAACGCCACTCACATCTACGG (SEQ ID NO: 30) | GGACACCTCAATAATGTTGGCAC (SEQ ID NO: 31) |

Immunocytochemistry

ATGL-KO and WT iPSCs and control ES cells were grown on mMEF feeders in 24-well plates and fixed in 4% PFA for immunostaining. Cells from embryoid body (EB) cultures were dissociated using collagenase (Roche Applied Science) at day 10 of differentiation and incubated on gelatin-coated chamber slides for an additional two days prior to fixation. A list of antibodies used is given in the Supplemental Procedures. In co-staining experiments with Oil Red O, antibody staining was performed first, followed by Oil Red O staining as described below. Images were captured on a Leica DM6000B or DMI4000B microscope using a Leica DFC420 (color, fluorescence) or DFC350FX camera (black and white, fluorescence).

Oil Red O Staining

Prior to ORO staining, cell cultures were first assessed for viability based on their ability to reduce resazurin (Sigma), which was added to the culture medium at a final concentration of 50-75 uM. Resazurin-treated cells were incubated for 2.5 hrs prior to reading the resofurin fluorescent signal (excitation at 560 nm, emission at 590 nm) on a TECAN Safire2 plate reader (Tecan, Durham, N.C.). The culture medium was subsequently removed, and cells were washed with PBS, fixed in 10% formalin overnight, and stained with filtered Oil Red O (Sigma) solution (60% isopropanol, 40% ddH2O). After removal of ORO solution, cells were washed multiple times with ddH2O water prior to visualization with phase-contrast microscopy. To quantify the level of ORO, ORO-equivalent volumes of 100% isopropanol were added to each well and the absorbance at 500 nm was measured using the Tecan Safire2☐ reader. The ratio of ORO absorbance units to resorufin fluorescence units (i.e. normalized ORO level) was calculated for each sample. For details of the preparation of cell cultures for resazurin/ORO staining.

High Throughput iPSC Chemical Screening

ATGL-KO iPSCs were plated in 96-well plates at an initial density of ~8000 cells/well in differentiation medium. Following one day of adherence and differentiation, the Prestwick® collection and DMSO controls were applied to the cells in duplicate wells using a CyBio Vario® automated pin-transfer robot (CyBio, Jena, Germany). The cells were then incubated for 6 additional days prior to analysis with the resazurin and ORO assays. Normalized ORO values were calculated for each compound- or DMSO-treated well and a Z-score (see Statistical analysis section below) was subsequently calculated for each compound treatment. Functional annotations of select top-scoring compounds were compiled from the NCBI PubChem database (http://pubchem.ncbi.nlm.nih.gov).

Cellular Metabolism Assays

ATGL-KO and WT iPSCs were differentiated as EBs to day 9, then collagenase-dissociated and re-plated onto gelatin-coated XF24 plates (Seahorse Bioscience, Andover, Mass.) at a density of 250,000 cells/well. Following an overnight incubation (12-16 hrs) in differentiation medium supplemented with drugs or DMSO, the cells were acclimated to atmospheric CO2 in drug-containing buffer-free medium (Wu, M. et al., 2007) for 1 hour at 37° C. Oxygen consumption rates (OCR) and extracellular acidification rates (ECAR) were measured on the Seahorse Extracellular Flux 24 Analyzer using previously established procedures (Gohil et al., 2010; Wu, M. et al., 2007) and normalized against cell number as assessed by the resazurin assay described above. In all wells, antimycin, an electron transport chain inhibitor, was added at the end of the assay to ascertain that mitochondrial function in the drug-treated cells had been intact and that the OCR and ECAR results were not due to direct mitochondrial toxicity effects from drug treatment.

Statistical Analysis

Z-scores were calculated as Z-scores were calculated as $$Z_x = \frac{O_x - \overline{O}_{DMSO}}{\sigma_{DMSO}},$$

where $O_x$=normalized ORO level of ATGL-KO cells treated with compound x, $\overline{O}_{DMSO}$=mean normalized ORO level of DMSO-treated cells, and $\sigma_{DMSO}$=standard deviation of normalized ORO levels in DMSO-treated samples. For all other analyses, the significance between two populations was determined using a two-tailed student's-test assuming normal distribution and unequal variances. A compound-set enrichment analysis, analogous to a gene set enrichment analysis (Shaw et al., 2010; Subramanian et al., 2005), was performed to assess overrepresentation of glycolysis switch inducers in the top-scoring screen hits.

Lipidomics Assay

The lipidomic profiles for ATGL-KO and -WT iPSCs differentiated to day 12 were obtained using LC-MS as described previously (Rhee et al., 2010), with the following modifications for cultured cells. Cellular lipids were extracted from pelleted EB cultures (~106 cells) with 250 L HPLC grade isopropanol (Sigma), and 2 L of the supernatant was directly injected onto a reversed-phase 150×3.0 mm Prosphere HP C4 column (Grace, Columbia, Md.) for separation prior to analysis by a 4000 QTRAP triple quadrupole mass spectrometer (Applied Biosystems/Sciex, Foster City, Calif.). MultiQuant software (version 1.1, Applied Biosystems/Sciex) was used for automated peak integration and peaks were manually reviewed for quality of integration.

Immunocytochemistry

Primary antibodies used included those against Sox2 (Abcam 59776-100), Nanog (CosmoBio REC-RCAB0002 PF), SSEA-1 (Hybridoma Bank MC-480), cTnT (NeoMarkers MS-295-p1), sarcomeric actinin (Sigma A781 1), smooth muscle myosin heavy chain (Biomedical Technologies BT-562), AFP (Santa Cruz 15375), and nestin (Abcam 6142). Alexafluor-488 conjugated secondary antibodies (Molecular Probes) were used for visualization.

Oil Red O Staining

To prepare differentiating ATGL-KO and -WT iPSCs for Oil Red O (ORO) staining, EBs were dissociated at day 6 using 0.25% trypsin/EDTA (Invitrogen, Carlsbad, Calif.) and re-plated onto gelatin-coated 35-mm plates in serial dilutions to allow for similar cell numbers at different time points of staining. For certain experiments, the re-plated iPSCs were incubated in the presence of select compounds from the high throughput screen prior to staining. Cells differentiated and treated as monolayers in 96-well plates were stained in situ. Resazurin was added to the culture medium at a final concentration of 50 or 75 M for 96-well or 35-mm plates, respectively. For 35-mm plate samples, aliquots of medium were transferred to blank 96-well plates after the incubation period to enable reading on the TECAN machine. The culture medium was subsequently removed, and cells were washed with PBS, fixed in 10% formalin overnight, and stained with 35 μL (per well of a 96-well plate) or 1 mL (per 35-mm plate) of filtered Oil Red O solution (60% isopropanol, 40% ddH2O) for 3 or 5 minutes, respectively. After removal of ORO solution, cells were washed multiple times with ddH2O water prior to elution with OR equivalent volumes of 100% isopropanol.

Compound Set Enrichment Analysis (CSEA)

CSEA is adapted from the Gene Set Enrichment Algorithm developed to identify sets of coordinately regulated genes within gene expression data (Shaw et al., 2010; Subramanian et al., 2005). Given a list of compounds ranked according to normalized ORO score, and a pre-specified set of compounds S (defined by a shared attribute), CSEA asks if members of set S are randomly distributed throughout the ranked list, or are enriched at the top or bottom. A normalized enrichment score (NES) is calculated by walking down the ranked list, increasing a running-sum statistic whenever a member of set S is encountered, and decreasing the running-sum statistic whenever a compound not in set S is encountered. The enrichment score is a weighted Kolmogorov-Smirnov-like statistic.

Our ranked list consisted of all screened compounds, but excluded those that significantly impaired cell viability (i.e. Z-score for ORO assay>2, or the extreme tail of the Z-score distribution (see FIG. 7b). This resulted in 1016/1118 compounds being included in the analysis. The glycolytic switch set was obtained from a published dataset of such compounds (Gohil et al., 2010). The top 41 compounds from the published dataset that were also in our ranked list (representing ~1% of total compounds in Gohil et al., 2010) were analyzed (Table S2).

Calculations were performed using the GSEA module of the GenePattern software suite (http://www.broadinstitute.org/cancer/software/genepattern/) (Reich et al., 2006) using standard settings for pre-ranked lists. P-value for the glycolytic switch set was calculated by randomly generating 1000 compound sets with the same number of compounds as our glycolytic switch set, and generating a null distribution from the enrichment scores for these 1000 random compound sets.

REFERENCES

Carvajal-Vergara, X., Sevilla, A., D'Souza, S. L., Ang, Y. S., Schaniel, C., Lee, D. F., Yang, L., Kaplan, A. D., Adler, E. D., Rozov, R., et al. (2010). Patient-specific induced pluripotent stem cell-derived models of LEOPARD syndrome. Nature 465, 808-812.

Chen, S., Borowiak, M., Fox, J. L., Maehr, R., Osafune, K., Davidow, L., Lam, K., Peng, L. F., Schreiber, S. L., Rubin, L. L., et al. (2009). A small molecule that directs differentiation of human ESCs into the pancreatic lineage. Nat. Chem. Biol. 5, 258-265.

Dimos, J. T., Rodolfa, K. T., Niakan, K. K., Weisenthal, L. M., Mitsumoto, H., Chung, W., Croft, G. F., Saphier, G., Leibel, R., Goland, R., et al. (2008). Induced pluripotent stem cells generated from patients with ALS can be differentiated into motor neurons. Science 321, 1218-1221.

Ebert, A. D., and Svendsen, C. N. (2010). Human stem cells and drug screening: opportunities and challenges. Nat. Rev. Drug. Discov. 5, 367-372.

Fischer, J., Lefèvre, C., Morava, E., Mussini, J. M., Laforêt, P., Negre-Salvayre, A., Lathrop, M., and Salvayre, R. (2007). The gene encoding adipose triglyceride lipase (PNPLA2) is mutated in neutral lipid storage disease with myopathy. Nat. Genet. 39, 28-30.

Girard, J., Ferré, P., Pégorier, J. P., and Duée, P. H. (1992). Adaptations of glucose and fatty acid metabolism during perinatal period and suckling-weaning transition. Physiol. Rev. 72, 507-562.

Gohil, V. M., Sheth, S. A., Nilsson, R., Wojtovich, A. P., Lee, J. H., Perocchi, F., Chen, W., Clish, C. B., Ayata, C., Brookes, P. S., et al. (2010). Nutrient-sensitized screening for drugs that shift energy metabolism from mitochondrial respiration to glycolysis. Nat. Biotech. 28, 249-255.

Goldsby, R. A., and Heytler, P. G. (1963). Uncoupling of oxidative phosphorylation by carbonyl cyanide phenylhydrazones. IL Effects of carbonyl cyanide m-chlorophenylhydrazone on mitochondrial respiration. Biochemistry 2, 1142-1147.

Grigoriadis, A. E., Kennedy, M., Bozec, A., Brunton, F., Stenbeck, G., Park, I. H., Wagner, E. F., and Keller, G. M. (2010). Directed differentiation of hematopoietic precursors and functional osteoclasts from human ES and iPS cells. Blood 115, 2769-2776.

Gunaseeli, I., Doss, M. X., Antzelevitch, C., Hescheler, J., and Sachinidis, A. Induced pluripotent stem cells as a model for accelerated patient- and disease-specific drug discovery. (2010). Curr. Med. Chem. 17, 759-766.

Haemmerle, G., Lass, A., Zimmermann, R., Gorkiewicz, G., Meyer, C., Rozman, J., Heldmaier, G., Maier, R., Theussl, C., Eder, S., et al. (2006). Defective lipolysis and altered energy metabolism in mice lacking adipose triglyceride lipase. Science 312, 734-737.

Huang, X. and Wu, S. M. (2010). Isolation and characterization of cardiac progenitor cells from pluripotent stem cells. Curr. Protoc. Stem. Cell. Biol. In Press.

Kennedy, J. A., Unger, S. A., and Horowitz, J. D. (1996). Inhibition of carnitine palmitoyltransferase-1 in rat heart and liver by perhexyline and amiodarone. Biochem. Pharmacol. 52, 273-280.

Kiskinis, E. and Eggan, K. (2010). Progress toward the clinical application of patient-specific pluripotent stem cells. J. Clin. Invest. 120, 51-59.

Kobayashi, K., Inoguchi, T., Maeda, Y., Nakashima, N., Kuwano, A., Eto, E., Ueno, N., Sasaki, S., Sawada, F., Fujii, M., et al. (2008). The lack of the C-terminal domain of adipose triglyceride lipase causes neutral lipid storage disease through impaired interactions with lipid droplets. J. Clin. Endocrinol. Metab. 93, 2877-2884.

Kobayashi, T., Yamaguchi, T., Hamanaka, S., Kato-Itoh, M., Yamazaki, Y., Ibata, M., Sato, H., Lee, Y. S., Usui, J., Knisely, A. S., et al. (2010). Generation of rat pancreas in mouse by interspecific blastocyst injection of pluripotent stem cells. Cell 142, 787-799.

Laflamme, M. A., Chen, K. Y., Naumova, A. V., Muskheli, V., Fugate, J. A., Dupras, S. K., Reinecke, H., Xu, C., Hassanipour, M., Police, S., et al. (2007). Cardiomyocytes derived from human embryonic stem cells in pro-survival factors enhance function of infarcted rat hearts. Nat. Biotechnol. 25, 1015-1024.

Lake, A. C., Sun, Y., Li, J. L., Kim, J. E., Johnson, J. W., Li, D., Revett, T., Shih, H. H., Liu, W., Paulsen, J. E., et al. (2005). Expression, regulation, and triglyceride hydrolase activity of adiponutrin family members. J. Lipid Res. 46, 2477-2487.

Lee, G., Papapetrou, E. P., Kim, H., Chambers, S. M., Tomishima, M. J., Fasano, C. A., Ganat, Y. M., Menon, J., Shimizu, F., Viale, A., et al. (2009). Modelling pathogenesis and treatment of familial dysautonomia using patient-specific iPSCs. Nature 461, 402-406.

Lengner, C. J. (2010). iPS cell technology in regenerative medicine. Ann. N.Y. Acad. Sci. 1192, 38-44.

Maehr, R., Chen, S., Snitow, M., Ludwig, T., Yagasaki, L., Goland, R., Leibel, R. L., Melton, D. A. (2009). Generation of pluripotent stem cells from patients with type 1 diabetes. Proc. Natl. Acad. Sci. USA 106, 15768-15773.

Moretti, A., Bellin, M., Welling, A., Jung, C. B., Lam, J. T., Bott-Flügel, L., Dorn, T., Goedel, A., Höhnke, C., Hofmann, F., et al. (2010). Patient-Specific Induced Pluripotent Stem-Cell Models for Long-QT Syndrome. N. Engl. J. Med. 363, 1397-1409.

Pinent, M., Hackl, H., Burkard, T. R., Prokesch, A., Papak, C., Scheideler, M., Hämmerle, G., Zechner, R., Trajanoski, Z., and Strauss, J. G. (2008). Differential transcriptional modulation of biological processes in adipocyte triglyceride lipase and hormone-sensitive lipase-deficient mice. Genomics 92, 26-32.

Raya, A., Rodríguez-Pizà, I., Guenechea, G., Vassena, R., Navarro, S., Barrero, M. J., Consiglio, A., Castellà, M., Río, P., Sleep, E., et al. (2009). Disease-corrected haematopoietic progenitors from Fanconi anaemia induced pluripotent stem cells. Nature 460, 53-59.

Rhee, E. P., Souza, A., Farrell, L., Pollak, M. R., Lewis, G. D., Steele, D. J., Thadhani, R., Clish, C. B., Greka, A., and Gerszten, R. E. (2010). Metabolite profiling identifies markers of uremia. J. Am. Soc. Nephrol. 21, 1041-1051.

Rideout, W. M. 3rd, Hochedlinger, K., Kyba, M., Daley, G. Q., Jaenisch, R. (2002). Correction of a genetic defect by nuclear transplantation and combined cell and gene therapy. Cell 109, 17-27.

Shaw, S. Y., Blodgett, D. M., Ma, M. S., Westly, E. C., Clemons, P. A., Subramanian, A., and Schreiber, S. L. (2010). Disease allele-dependent small-molecule sensitivities in blood cells from monogenic diabetes. Proc. Natl. Acad. Sci. USA, in press.

Stadtfeld, M., Brennand, K., and Hochedlinger, K. (2008). Reprogramming of pancreatic Wobus, A. M., Wallukat, G. and Hescheler, J. (1991). Pluripotent mouse embryonic stem cells are able to differentiate into cardiomyocytes expressing chronotropic responses to adrenergic and cholinergic agents and Ca2+ channel blockers. Differentiation 48, 173-182.

Wu, M., Neilson, A., Swift, A. L., Moran, R., Tamagnine, J., Parslow, D., Armistead, S., Lemire, K., Orrell, J., Teich, J., et al. (2007). Multiparameter metabolic analysis reveals a close link between attenuated mitochondrial bioenergetic function and enhanced glycolysis dependency in human tumor cells. Am. J. Physiol. Cell Physiol. 292, C125-C136.

Wu, S. M., Fujiwara, Y., Cibulsky, S. M., Clapham, D. E., Lien, C. L., Schultheiss, T. M., and Orkin, S. H. (2006). Developmental Origin of a Bipotential Myocardial and Smooth Muscle Cell Precursor in the Mammalian Heart. Cell 127, 1137-1150.

Reich, M., Liefeld, T., Gould, J., Lerner, J., Tamayo, P., and Mesirov, J. P. (2006). GenePattern 2.0 Nat. Genet. 38, 500-501.

TABLE 1

Rank order of compounds according to their z-score

| Compound Name | Z-score |
| --- | --- |
| Fendiline hydrochloride | −2.53 |
| Vinpocetine | −2.4105 |
| Mefloquine hydrochloride | −2.3573 |
| Perhexiline maleate | −2.3117 |
| Dicyclomine hydrochloride | −2.1533 |
| Tacrine hydrochloride hydrate | −2.143 |
| Tomatine | −2.0901 |
| Gossypol | −2.0704 |
| 2-Aminobenzenesulfonamide | −1.9389 |
| Napelline | −1.869 |
| Clidinium bromide | −1.8548 |
| Estrone | −1.8166 |
| Zuclopenthixol hydrochloride | −1.8038 |
| Cortisone | −1.8033 |
| Bepridil hydrochloride | −1.7961 |
| Monocrotaline | −1.7819 |
| Solanine alpha | −1.7798 |
| Nitrendipine | −1.7782 |
| Metyrapone | −1.7744 |
| Estropipate | −1.7711 |
| Lorglumide sodium salt | −1.7664 |
| Spironolactone | −1.7632 |
| Butylparaben | −1.7629 |
| Epitiostanol | −1.7564 |
| Seneciphylline | −1.7519 |
| Caffeic acid | −1.7446 |
| Ethopropazine hydrochloride | −1.7382 |
| Monobenzone | −1.7289 |
| Cromolyn disodium salt | −1.7273 |
| Beta-Escin | −1.7261 |
| Tocopherol (R,S) | −1.721 |
| Nadolol | −1.7201 |
| Nisoxetine hydrochloride | −1.699 |
| Nimodipine | −1.6971 |
| Spiperone | −1.6819 |
| Chenodiol | −1.6767 |
| Clotrimazole | −1.6708 |

TABLE 1-continued

Rank order of compounds according to their z-score

| Compound Name | Z-score |
|---|---|
| Dioxybenzone | −1.6584 |
| Tracazolate hydrochloride | −1.6368 |
| Fluspirilen | −1.6301 |
| Sertraline hydrochloride | −1.6299 |
| Cefoxitin sodium salt | −1.629 |
| L(−)-vesamicol hydrochloride | −1.6146 |
| Cinnarizine | −1.6064 |
| Fenofibrate | −1.6051 |
| Cyproheptadine hydrochloride | −1.6013 |
| Benzthiazide | −1.594 |
| Tetrahydroxy-1,4-quinone monohydrate | −1.5885 |
| Iocetamic acid | −1.5742 |
| Novobiocin sodium salt | −1.5591 |
| Nilutamide | −1.5582 |
| Ebselen | −1.5273 |
| Perphenazine | −1.5218 |
| Clioquinol | −1.5195 |
| Trigonelline | −1.518 |
| Ribavirin | −1.5081 |
| Labetalol hydrochloride | −1.5017 |
| Pantothenic acid calcium salt monohydrate | −1.5008 |
| Acenocoumarol | −1.4804 |
| Idazoxan hydrochloride | −1.447 |
| Ethynodiol diacetate | −1.4458 |
| Mevalonic-D, L acid lactone | −1.4333 |
| Ricinine | −1.4299 |
| Dyclonine hydrochloride | −1.4276 |
| Promethazine hydrochloride | −1.4251 |
| Ifosfamide | −1.424 |
| Indoprofen | −1.4204 |
| Trimeprazine tartrate | −1.418 |
| Karakoline | −1.4178 |
| Pipemidic acid | −1.4165 |
| Betulin | −1.4148 |
| Delcorine | −1.4115 |
| Cyclopenthiazide | −1.4107 |
| S-(+)-ibuprofen | −1.4076 |
| (cis-) Nanophine | −1.4074 |
| Gabexate mesilate | −1.4041 |
| Sulfinpyrazone | −1.4016 |
| Flurbiprofen | −1.4 |
| Bumetanide | −1.3983 |
| Ampicillin trihydrate | −1.3793 |
| Cyclosporin A | −1.3785 |
| THIP Hydrochloride | −1.3776 |
| Piribedil hydrochloride | −1.3522 |
| Mianserine hydrochloride | −1.3517 |
| Oxalamine citrate salt | −1.3452 |
| Reserpinic acid hydrochloride | −1.3417 |
| Lymecycline | −1.3365 |
| Hesperetin | −1.3358 |
| Delsoline | −1.3301 |
| Suxibuzone | −1.3282 |
| Cyanocobalamin | −1.3236 |
| Ciprofloxacin hydrochloride | −1.3212 |
| Lynestrenol | −1.3181 |
| Sulfamonomethoxine | −1.3171 |
| Nomifensine maleate | −1.3149 |
| Dexamethasone acetate | −1.3076 |
| Acetylsalicylsalicylic acid | −1.3067 |
| Triamterene | −1.3039 |
| Pyrilamine maleate | −1.3015 |
| Pizotifen malate | −1.2994 |
| Danazol | −1.2973 |
| Deltaline | −1.2966 |
| Urapidil hydrochloride | −1.2828 |
| Heliotrine | −1.2812 |
| Esculin Hydrate | −1.2808 |
| Nortriptyline hydrochloride | −1.28 |
| Corticosterone | −1.2709 |
| Carbenoxolone disodium salt | −1.2656 |
| Prilocaine hydrochloride | −1.2624 |
| Dimaprit dihydrochloride | −1.2574 |
| Isoconazole | −1.2562 |
| Cyproterone acetate | −1.2528 |
| N-Acetyl-L-leucine | −1.2512 |
| Memantine Hydrochloride | −1.2487 |
| Fosfosal | −1.2351 |
| Fluvoxamine maleate | −1.2293 |
| Skimmianine | −1.2252 |
| Thiethylperazine malate | −1.2229 |
| Adenosine 5'-monophosphate monohydrate | −1.2202 |
| Iodixanol | −1.2199 |
| (−)-Cinchonidine | −1.2185 |
| Antazoline hydrochloride | −1.2181 |
| Picotamide monohydrate | −1.2123 |
| Trichlormethiazide | −1.2081 |
| Meclofenamic acid sodium salt monohydrate | −1.2044 |
| Triflusal | −1.2041 |
| Trolox | −1.1986 |
| Pivampicillin | −1.1929 |
| Tetrandrine | −1.1905 |
| Tamoxifen citrate | −1.1882 |
| Proadifen hydrochloride | −1.1876 |
| Diethylcarbamazine citrate | −1.1872 |
| Chrysene-1,4-quinone | −1.1808 |
| Haloperidol | −1.1776 |
| Biperiden hydrochloride | −1.1752 |
| Methylprednisolone, 6-alpha | −1.1745 |
| Harpagoside | −1.174 |
| Oxybenzone | −1.1732 |
| Triamcinolone | −1.1722 |
| Cinchonine | −1.1697 |
| Fluorocurarine chloride | −1.1648 |
| Azlocillin sodium salt | −1.1617 |
| Isotretinoin | −1.1597 |
| Pentoxifylline | −1.1547 |
| Meglumine | −1.1536 |
| Disopyramide | −1.1535 |
| Dizocilpine maleate | −1.1505 |
| Methylatropine nitrate | −1.1494 |
| Cephalexin monohydrate | −1.1486 |
| Famotidine | −1.1457 |
| Hippeastrine hydrobromide | −1.1441 |
| Methocarbamol | −1.1429 |
| Diclofenac sodium | −1.137 |
| Apramycin | −1.1349 |
| Aminohippuric acid | −1.1341 |
| Nitrocaramiphen hydrochloride | −1.1255 |
| Thioridazine hydrochloride | −1.1212 |
| Ungerine nitrate | −1.1174 |
| Oxyphenbutazone | −1.1165 |
| Cefsulodin sodium salt | −1.1155 |
| Benfluorex hydrochloride | −1.1069 |
| Iohexol | −1.1016 |
| Nalbuphine hydrochloride | −1.0996 |
| Oxybutynin chloride | −1.0993 |
| Pirenzepine dihydrochloride | −1.096 |
| Rilmenidine hemifumarate | −1.0936 |
| Levopropoxyphene napsylate | −1.0896 |
| Benzamil hydrochloride | −1.083 |
| Convolamine hydrochloride | −1.0829 |
| Metoclopramide monohydrochloride | −1.0824 |
| Idoxuridine | −1.0734 |
| Bacitracin | −1.0707 |
| Ticlopidine hydrochloride | −1.0702 |
| Proscillaridin A | −1.0698 |
| Eburnamonine (−) | −1.0688 |
| Equilin | −1.0652 |
| Triprolidine hydrochloride | −1.0644 |
| Meptazinol hydrochloride | −1.0631 |
| Spiramycin | −1.0612 |
| Pipenzolate bromide | −1.06 |
| Xylazine | −1.0585 |
| Sulfasalazine | −1.0569 |
| Aminophylline | −1.0552 |
| Fluoxetine hydrochloride | −1.0533 |
| Digoxigenin | −1.0521 |
| S(−)-terguride hydrogen maleate | −1.0498 |
| Oxolinic acid | −1.0488 |
| (+,−)-Synephrine | −1.0448 |
| Etifenin | −1.0427 |

TABLE 1-continued

Rank order of compounds according to their z-score

| Compound Name | Z-score |
|---|---|
| Tolmetin sodium salt dihydrate | −1.0425 |
| Metanephrine hydrochloride DL | −1.0419 |
| Yohimbine hydrochloride | −1.0356 |
| Hexestrol | −1.0339 |
| D-cycloserine | −1.0332 |
| Pyrazinamide | −1.0312 |
| Lanatoside C | −1.0291 |
| Clemastine fumarate | −1.0269 |
| Thalidomide | −1.026 |
| Roxithromycin | −1.026 |
| Adrenosterone | −1.025 |
| Graveoline | −1.0242 |
| Tiapride hydrochloride | −1.0178 |
| Azacyclonol | −1.0159 |
| Fluticasone propionate | −1.0154 |
| Nimesulide | −1.0153 |
| Flunixin meglumine | −1.0122 |
| Doxazosin mesylate | −1.0121 |
| GBR 12909 dihydrochloride | −1.0102 |
| Cloxacillin sodium salt | −1.0101 |
| Luteolin | −1.0098 |
| Doxepin hydrochloride | −1.0091 |
| Oxaprozin | −1.009 |
| Phthalylsulfathiazole | −1.0074 |
| Dehydrocholic acid | −1.006 |
| Salbutamol | −0.9959 |
| Flecainide acetate | −0.9948 |
| Ganciclovir | −0.9945 |
| Clopamide | −0.9945 |
| Ethionamide | −0.9932 |
| Bucladesine sodium salt | −0.9927 |
| Fludrocortisone acetate | −0.9911 |
| Propantheline bromide | −0.9862 |
| Chlorprothixene hydrochloride | −0.9824 |
| Diloxanide furoate | −0.9785 |
| Catechin-(+,−) hydrate | −0.9777 |
| Fusaric acid | −0.977 |
| Diethylstilbestrol | −0.977 |
| Fipexide hydrochloride | −0.9747 |
| Diltiazem hydrochloride | −0.974 |
| Clomipramine hydrochloride | −0.9732 |
| Avermectin B1 | −0.9704 |
| Methylhydantoin-5-(L) | −0.97 |
| Conessine | −0.969 |
| Propofol | −0.9649 |
| Pentolinium bitartrate | −0.9629 |
| Meprylcaine hydrochloride | −0.9597 |
| Trimethoprim | −0.9568 |
| Tiratricol, 3,3′,5-triiodothyroacetic acid | −0.9554 |
| Estradiol-17 beta | −0.9541 |
| Felbinac | −0.9529 |
| Alverine citrate salt | −0.9516 |
| Oxethazaine | −0.9515 |
| Talampicillin hydrochloride | −0.9508 |
| Gliquidone | −0.9495 |
| Dimethadione | −0.9493 |
| Ambroxol hydrochloride | −0.9433 |
| LidocaOne hydrochloride | −0.9429 |
| Prednicarbate | −0.9408 |
| Mephenesin | −0.9401 |
| Ajmaline | −0.937 |
| Ethynylestradiol 3-methyl ether | −0.93 |
| Esculetin | −0.9295 |
| Butacaine | −0.9284 |
| Digitoxigenin | −0.9264 |
| Cyclizine hydrochloride | −0.9231 |
| Naftopidil dihydrochloride | −0.9212 |
| Paroxetine Hydrochloride | −0.9182 |
| Alprostadil | −0.9154 |
| Piperacillin sodium salt | −0.9149 |
| Tetrahydrozoline hydrochloride | −0.9102 |
| Hydroxyzine dihydrochloride | −0.9071 |
| Metaraminol bitartrate | −0.9024 |
| Acemetacin | −0.9005 |
| Pronethalol hydrochloride | −0.9002 |
| Ajmalicine hydrochloride | −0.8989 |
| Prednisolone | −0.8986 |
| Trimethadione | −0.8958 |
| Flucytosine | −0.8908 |
| alpha-Santonin | −0.8908 |
| Terfenadine | −0.8896 |
| Beta-sistosterol | −0.8867 |
| Chlorambucil | −0.8818 |
| Dextromethorphan hydrobromide monohydrate | −0.8776 |
| Cefazolin sodium salt | −0.8698 |
| Serotonin hydrochloride | −0.8664 |
| Nitrofural | −0.866 |
| Quercetine dihydrate | −0.8659 |
| Clorgyline hydrochloride | −0.8658 |
| Flumequine | −0.8648 |
| Nitrarine dihydrochloride | −0.8582 |
| Raloxifene hydrochloride | −0.8574 |
| Levamisole hydrochloride | −0.8539 |
| Cefmetazole sodium salt | −0.8537 |
| Econazole nitrate | −0.8488 |
| 3-Acetylcoumarin | −0.8473 |
| Naphazoline hydrochloride | −0.8458 |
| Cefotiam hydrochloride | −0.8453 |
| Etofylline | −0.8406 |
| Calycanthine | −0.8381 |
| Ketorolac tromethamine | −0.8373 |
| Cefalonium | −0.8363 |
| Carbimazole | −0.836 |
| Epiandrosterone | −0.835 |
| Cefotaxime sodium salt | −0.8289 |
| Niacin | −0.8285 |
| Tolfenamic acid | −0.8256 |
| Homochlorcyclizine dihydrochloride | −0.8178 |
| Amoxapine | −0.8161 |
| Digoxin | −0.815 |
| Flufenamic acid | −0.8139 |
| Metixene hydrochloride | −0.8136 |
| Tolbutamide | −0.8086 |
| Pempidine tartrate | −0.8069 |
| Methacholine chloride | −0.8044 |
| Hydrocotarnine hydrobromide | −0.8038 |
| Benfotiamine | −0.7979 |
| beta-Belladonnine dichloroethylate | −0.7978 |
| Benzylpenicillin sodium | −0.794 |
| Galanthamine hydrobromide | −0.7931 |
| Lisuride (S)(−) | −0.7927 |
| Isoetharine mesylate salt | −0.7902 |
| Norethynodrel | −0.7872 |
| Indomethacin | −0.7862 |
| Rolipram | −0.7794 |
| Anabasine | −0.7781 |
| Dimenhydrinate | −0.7776 |
| Vigabatrin | −0.7771 |
| Iopanoic acid | −0.7767 |
| Bromocryptine mesylate | −0.775 |
| Homosalate | −0.7744 |
| Sulfamethizole | −0.7734 |
| Hymecromone | −0.7731 |
| SR-95639A | −0.7703 |
| Isocorydine (+) | −0.7668 |
| Isoxicam | −0.7646 |
| Mometasone furoate | −0.7613 |
| Moxalactam disodium salt | −0.7608 |
| Zimelidine dihydrochloride monohydrate | −0.7577 |
| Suprofen | −0.7501 |
| Pimozide | −0.7483 |
| Metolazone | −0.7452 |
| Fenoterol hydrobromide | −0.7445 |
| Imipenem | −0.7436 |
| Folinic acid calcium salt | −0.7409 |
| Enoxacin | −0.7386 |
| Aminopurine, 6-benzyl | −0.7385 |
| Tomatidine | −0.7378 |
| Pargyline hydrochloride | −0.735 |
| Foliosidine | −0.7349 |
| S(−)Eticlopride hydrochloride | −0.7335 |
| Ethotoin | −0.7327 |

TABLE 1-continued

Rank order of compounds according to their z-score

| Compound Name | Z-score |
|---|---|
| Proxyphylline | −0.7317 |
| Diphenidol hydrochloride | −0.7294 |
| Bergenin monohydrate | −0.7293 |
| (+)-Isoproterenol (+)-bitartrate salt | −0.728 |
| Astemizole | −0.7215 |
| Tribenoside | −0.7171 |
| Rauwolscine hydrochloride | −0.7161 |
| Chrysin | −0.7142 |
| Halcinonide | −0.7085 |
| Dydrogesterone | −0.7044 |
| Retinoic acid | −0.7042 |
| Sisomicin sulfate | −0.7041 |
| Methantheline bromide | −0.7033 |
| Dihydroergotamine tartrate | −0.7032 |
| Epirizole | −0.7031 |
| Loxapine succinate | −0.6976 |
| Dehydroisoandosterone 3-acetate | −0.697 |
| Zardaverine | −0.6963 |
| Fursultiamine Hydrochloride | −0.696 |
| Asiaticoside | −0.6936 |
| Ondansetron Hydrochloride | −0.6933 |
| Amyleine hydrochloride | −0.692 |
| Amiprilose hydrochloride | −0.6893 |
| Moxonidine | −0.6893 |
| Carteolol hydrochloride | −0.6876 |
| Ozagrel hydrochloride | −0.6787 |
| Nabumetone | −0.6754 |
| Indapamide | −0.6747 |
| Nystatine | −0.6743 |
| Norethindrone | −0.6688 |
| Sulconazole nitrate | −0.6576 |
| Chlorotrianisene | −0.6534 |
| Chlormezanone | −0.6525 |
| Acetaminophen | −0.6512 |
| Azapropazone | −0.6493 |
| Propafenone hydrochloride | −0.6438 |
| Niflumic acid | −0.6436 |
| Bromperidol | −0.6428 |
| Alfaxalone | −0.6412 |
| Boldine | −0.6389 |
| Benserazide hydrochloride | −0.638 |
| Naftifine hydrochloride | −0.6354 |
| Mifepristone | −0.6348 |
| Glycocholic acid | −0.6342 |
| Lobelanidine hydrochloride | −0.6306 |
| Ethambutol dihydrochloride | −0.6303 |
| Tiaprofenic acid | −0.6271 |
| Penbutolol sulfate | −0.627 |
| Methylhydantoin-5-(D) | −0.6204 |
| Pirlindole mesylate | −0.619 |
| Glycopyrrolate | −0.6161 |
| Thioperamide maleate | −0.6114 |
| Naltrexone hydrochloride dihydrate | −0.609 |
| Procyclidine hydrochloride | −0.6071 |
| Diperodon hydrochloride | −0.6048 |
| Norcyclobenzaprine | −0.6046 |
| Demecarium bromide | −0.6009 |
| Hexamethonium dibromide dihydrate | −0.5997 |
| Droperidol | −0.5996 |
| Ciprofibrate | −0.5993 |
| TetracaOne hydrochloride | −0.5979 |
| Josamycin | −0.5964 |
| Roxarsone | −0.5936 |
| Acetopromazine maleate salt | −0.5926 |
| Vancomycin hydrochloride | −0.5906 |
| 2-Chloropyrazine | −0.5863 |
| Omeprazole | −0.5848 |
| Clindamycin hydrochloride | −0.5846 |
| Austricine | −0.5795 |
| Harmaline hydrochloride dihydrate | −0.5714 |
| Cefamandole sodium salt | −0.5703 |
| Clemizole hydrochloride | −0.5701 |
| Canavanine sulfate monohydrate (L,+) | −0.5687 |
| (−)-Levobunolol hydrochloride | −0.5665 |
| Ethamivan | −0.565 |
| Ranitidine hydrochloride | −0.5642 |
| Cefaclor | −0.5619 |
| Clofazimine | −0.5584 |
| Bicuculline (+) | −0.5556 |
| Hydrastinine hydrochloride | −0.5549 |
| Mesoridazine besylate | −0.5525 |
| Laudanosine (R,S) | −0.5493 |
| Chlortetracycline hydrochloride | −0.5479 |
| Flutamide | −0.5472 |
| Bephenium hydroxynaphthoate | −0.5444 |
| Aceclofenac | −0.5442 |
| Lobeline alpha (−) hydrochoride | −0.5438 |
| Troleandomycin | −0.5429 |
| Cefadroxil | −0.5419 |
| Chlorpromazine hydrochloride | −0.5417 |
| Ioxaglic acid | −0.54 |
| Chlorpheniramine maleate | −0.5399 |
| Solasodine | −0.5386 |
| Flupentixol dihydrochloride cis-(Z) | −0.5309 |
| N6-methyladenosine | −0.5287 |
| Hydroxytacrine maleate (R,S) | −0.525 |
| Rifampicin | −0.5227 |
| Procaine hydrochloride | −0.5215 |
| Praziquantel | −0.5159 |
| Lactobionic acid | −0.5092 |
| Kawain | −0.5048 |
| Colistin sulfate | −0.5041 |
| Securinine | −0.5036 |
| Tenoxicam | −0.5016 |
| Midodrine hydrochloride | −0.5001 |
| Quinethazone | −0.4993 |
| Prenylamine lactate | −0.492 |
| Piperidolate hydrochloride | −0.4895 |
| Pimethixene maleate | −0.4872 |
| Nalidixic acid sodium salt hydrate | −0.4868 |
| Zaprinast | −0.4842 |
| Vincamine | −0.4826 |
| Piperacetazine | −0.4798 |
| (−)-Eseroline fumarate salt | −0.478 |
| Harmane hydrochloride | −0.4768 |
| Ribostamycin sulfate salt | −0.4737 |
| Dobutamine hydrochloride | −0.4732 |
| Moxisylyte hydrochoride | −0.4722 |
| Lansoprazole | −0.4696 |
| Gelsemine | −0.4693 |
| Fenoprofen calcium salt dihydrate | −0.4668 |
| Guanadrel sulfate | −0.4661 |
| Sertaconazole nitrate | −0.4658 |
| Remoxipride Hydrochloride | −0.4559 |
| Alfadolone acetate | −0.4554 |
| Furaltadone hydrochloride | −0.4516 |
| (R)-Propranolol hydrochloride | −0.4494 |
| Vidarabine | −0.443 |
| (S)-(−)-Cycloserine | −0.4402 |
| Metoprolol-(+,−) (+)-tartrate salt | −0.4304 |
| Brinzolamide | −0.419 |
| Rimexolone | −0.4134 |
| Iproniazide phosphate | −0.4106 |
| Butoconazole nitrate | −0.4077 |
| Zidovudine, AZT | −0.4063 |
| Sulfamethoxazole | −0.4061 |
| Dapsone | −0.4061 |
| Thioproperazine dimesylate | −0.4051 |
| Glafenine hydrochloride | −0.4014 |
| Tinidazole | −0.3977 |
| Diflunisal | −0.3972 |
| Atractyloside potassium salt | −0.3937 |
| Naloxone hydrochloride | −0.3899 |
| Fenbufen | −0.3877 |
| Bethanechol chloride | −0.3853 |
| Metaproterenol sulfate, orciprenaline sulfate | −0.3842 |
| Lysergol | −0.3809 |
| Terconazole | −0.3786 |
| Diprophylline | −0.3767 |
| Cetirizine dihydrochloride | −0.3764 |
| Tiabendazole | −0.3752 |
| Naproxen | −0.3678 |

TABLE 1-continued

Rank order of compounds according to their z-score

| Compound Name | Z-score |
|---|---|
| Guanabenz acetate | −0.3551 |
| Bemegride | −0.3526 |
| Sparteine (−) | −0.3524 |
| Rolitetracycline | −0.3523 |
| Benzbromarone | −0.349 |
| Benzydamine hydrochloride | −0.3467 |
| Practolol | −0.3373 |
| Dantrolene sodium salt | −0.3347 |
| Evoxine | −0.3336 |
| Pergolide mesylate | −0.3289 |
| Hydrastine hydrochloride | −0.3277 |
| Iodipamide | −0.3225 |
| Chlorthalidone | −0.3195 |
| Sulfacetamide sodic hydrate | −0.3059 |
| Propoxycaine hydrochloride | −0.3049 |
| Orphenadrine hydrochloride | −0.3046 |
| Ethacrynic acid | −0.302 |
| Dacarbazine | −0.3016 |
| Ampyrone | −0.2996 |
| Heptaminol hydrochloride | −0.2987 |
| Glipizide | −0.2981 |
| Tropine | −0.2952 |
| Isopropamide iodide | −0.2928 |
| Menadione | −0.29 |
| Sulfaphenazole | −0.2854 |
| Milrinone | −0.2851 |
| Methionine sulfoximine (L) | −0.2829 |
| Pilocarpine nitrate | −0.2819 |
| Ergocryptine-alpha | −0.2816 |
| Beclomethasone dipropionate | −0.2791 |
| Phenformin hydrochloride | −0.2777 |
| Canrenoic acid potassium salt | −0.274 |
| Iobenguane sulfate | −0.2715 |
| Benperidol | −0.2696 |
| Captopril | −0.2654 |
| Gemfibrozil | −0.2634 |
| R(−) Apomorphine hydrochloride hemihydrate | −0.2622 |
| Tetracycline hydrochloride | −0.2579 |
| Bezafibrate | −0.2571 |
| Ethisterone | −0.2541 |
| Corynanthine hydrochloride | −0.2498 |
| Phenazopyridine hydrochloride | −0.2483 |
| Gabapentin | −0.2478 |
| Leucomisine | −0.2458 |
| Mefenamic acid | −0.2407 |
| Verteporfin | −0.2331 |
| Procainamide hydrochloride | −0.2319 |
| Tranylcypromine hydrochloride | −0.2314 |
| Azathymine, 6 | −0.2304 |
| Repaglinide | −0.2231 |
| Apigenin | −0.2208 |
| Ketoprofen | −0.219 |
| Pivmecillinam hydrochloride | −0.219 |
| Sulpiride | −0.2187 |
| Hydrocortisone base | −0.2176 |
| Mefexamide hydrochloride | −0.2169 |
| Cimetidine | −0.2141 |
| Antipyrine | −0.2127 |
| Neomycin sulfate | −0.2127 |
| (−)-MK 801 hydrogen maleate | −0.2074 |
| Oxprenolol hydrochloride | −0.2057 |
| Chlorothiazide | −0.1987 |
| Denatonium benzoate | −0.1971 |
| Amoxicillin | −0.1957 |
| Pyrantel tartrate | −0.1933 |
| Dicloxacillin sodium salt | −0.1893 |
| Betamethasone | −0.1891 |
| 3-alpha-Hydroxy-5-beta-androstan-17-one | −0.187 |
| Methapyrilene hydrochloride | −0.1861 |
| Loperamide hydrochloride | −0.1814 |
| (+)-Levobunolol hydrochloride | −0.1813 |
| Mesalamine | −0.1803 |
| Picrotoxinin | −0.1703 |
| Betazole hydrochloride | −0.1702 |
| Flumethasone | −0.1671 |
| Levodopa | −0.1655 |
| Medrysone | −0.1611 |
| Clorsulon | −0.1576 |
| Levonordefrin | −0.1555 |
| Ursolic acid | −0.1541 |
| Khellin | −0.1533 |
| Moricizine hydrochloride | −0.1525 |
| Sulfameter | −0.1501 |
| Nafcillin sodium salt monohydrate | −0.1498 |
| Ticarcillin sodium | −0.1446 |
| Cyclobenzaprine hydrochloride | −0.1421 |
| Gabazine | −0.1416 |
| Xamoterol hemifumarate | −0.1402 |
| Furazolidone | −0.1396 |
| Trimipramine maleate salt | −0.138 |
| Nizatidine | −0.1369 |
| Etidronic acid, disodium salt | −0.1368 |
| Protriptyline hydrochloride | −0.1298 |
| Spectinomycin dihydrochloride | −0.1287 |
| Trapidil | −0.1226 |
| Sulfadoxine | −0.1202 |
| Quipazine dimaleate salt | −0.1189 |
| Mepenzolate bromide | −0.115 |
| Helveticoside | −0.1112 |
| Clebopride maleate | −0.108 |
| Ipratropium bromide | −0.1032 |
| Ginkgolide A | −0.1024 |
| Sulfamerazine | −0.0984 |
| Deptropine citrate | −0.0889 |
| Decamethonium bromide | −0.0864 |
| Propylthiouracil | −0.0857 |
| Phenethicillin potassium salt | −0.0851 |
| Buspirone hydrochloride | −0.0845 |
| Reserpine | −0.083 |
| Guanfacine hydrochloride | −0.0783 |
| Harmol hydrochloride monohydrate | −0.0757 |
| Terazosin hydrochloride | −0.0723 |
| Panthenol (D) | −0.069 |
| Risperidone | −0.0533 |
| Sulfisoxazole | −0.0512 |
| Ethoxyquin | −0.0471 |
| Meticrane | −0.0455 |
| Drofenine hydrochloride | −0.0455 |
| Buflomedil hydrochloride | −0.0451 |
| Flurandrenolide | −0.0402 |
| Kaempferol | −0.0374 |
| Nefopam hydrochloride | −0.0308 |
| Yohimbinic acid monohydrate | −0.0239 |
| Sulfamethoxypyridazine | −0.0234 |
| Miconazole | −0.018 |
| Paromomycin sulfate | −0.0138 |
| Acyclovir | −0.0091 |
| Vitexin | −0.0089 |
| Primidone | −0.0045 |
| Enilconazole | −0.0014 |
| Lomefloxacin hydrochloride | 0.00477 |
| Parthenolide | 0.00611 |
| Ceftazidime pentahydrate | 0.00611 |
| Dosulepin hydrochloride | 0.00689 |
| Streptozotocin | 0.0088 |
| Promazine hydrochloride | 0.01386 |
| Bupivacaine hydrochloride | 0.0187 |
| Tridihexethyl chloride | 0.01977 |
| Cisapride | 0.02062 |
| Urosiol | 0.02187 |
| Methyldopa (L,−) | 0.02395 |
| Methylergometrine maleate | 0.02492 |
| Phensuximide | 0.02844 |
| Citalopram Hydrobromide | 0.03052 |
| Isopyrin hydrochloride | 0.0325 |
| Bisoprolol fumarate | 0.03425 |
| Pindolol | 0.03656 |
| Maprotiline hydrochloride | 0.03741 |
| Trazodone hydrochloride | 0.03974 |
| Clonidine hydrochloride | 0.04408 |
| Triflupromazine hydrochloride | 0.04449 |
| Ethamsylate | 0.04738 |

TABLE 1-continued

Rank order of compounds according to their z-score

| Compound Name | Z-score |
|---|---|
| Mephentermine hemisulfate | 0.04889 |
| Moroxidine hydrochloride | 0.05075 |
| Prednisone | 0.05393 |
| Tranexamic acid | 0.05824 |
| Natamycin | 0.06039 |
| Benzonatate | 0.06563 |
| Minoxidil | 0.06676 |
| 3-Acetamidocoumarin | 0.06786 |
| Methazolamide | 0.06841 |
| Estriol | 0.06999 |
| Doxylamine succinate | 0.07172 |
| Baclofen (R,S) | 0.07861 |
| Methiothepin maleate | 0.08061 |
| Melatonin | 0.08162 |
| Ioversol | 0.08392 |
| Retrorsine | 0.08676 |
| Theobromine | 0.09359 |
| Bacampicillin hydrochloride | 0.09702 |
| Sulfadiazine | 0.09783 |
| Biotin | 0.1016 |
| Glimepiride | 0.10429 |
| Mebeverine hydrochloride | 0.10965 |
| Nifenazone | 0.11312 |
| Amiodarone hydrochloride | 0.11386 |
| Epivincamine | 0.11611 |
| Riboflavine | 0.1165 |
| Oxymetazoline hydrochloride | 0.11989 |
| Sulfathiazole | 0.12264 |
| Betonicine | 0.12346 |
| Proglumide | 0.12348 |
| Chloropyramine hydrochloride | 0.124 |
| Dienestrol | 0.12678 |
| Fluorometholone | 0.1317 |
| Tetramisole hydrochloride | 0.13328 |
| Arecoline hydrobromide | 0.13727 |
| Nadide | 0.13852 |
| Etilefrine hydrochloride | 0.13978 |
| Quinacrine dihydrochloride dihydrate | 0.141 |
| Zoxazolamine | 0.14233 |
| Guaifenesin | 0.14397 |
| Chlorogenic acid | 0.14857 |
| Torsemide | 0.15409 |
| Kynurenine, 3-hydroxy (R,S) | 0.15671 |
| Dichlorphenamide | 0.16242 |
| Enalapril maleate | 0.16449 |
| Aztreonam | 0.17282 |
| N-Acetyl-DL-homocysteine Thiolactone | 0.17718 |
| Arbutin | 0.18061 |
| Hydroflumethiazide | 0.18552 |
| Bambuterol hydrochloride | 0.18583 |
| Pseudopelletierine hydrochloride | 0.19111 |
| Liothyronine | 0.19538 |
| Thyroxine (L) | 0.19553 |
| Dilazep dihydrochloride | 0.19669 |
| (−)-Adenosine 3',5'-cyclic monophosphate | 0.1984 |
| Chlorpropamide | 0.19899 |
| Phenoxybenzamine hydrochloride | 0.20314 |
| Adamantamine fumarate | 0.20847 |
| Butirosin disulfate salt | 0.21213 |
| Desipramine hydrochloride | 0.21679 |
| Carbinoxamine maleate salt | 0.21805 |
| 6-Furfurylaminopurine | 0.21921 |
| Flunarizine dihydrochloride | 0.22066 |
| Debrisoquin sulfate | 0.22275 |
| Flunisolide | 0.22409 |
| Stachydrine hydrochloride | 0.22476 |
| Telenzepine dihydrochloride | 0.22572 |
| Etomidate | 0.22737 |
| Dibucaine | 0.22741 |
| Sotalol hydrochloride | 0.2363 |
| Benzathine benzylpenicillin | 0.23801 |
| Dubinidine | 0.23846 |
| Clenbuterol hydrochloride | 0.23905 |
| Gliclazide | 0.24038 |
| (1-[(4-Chlorophenyl)phenyl-methyl]-4-methylpiperazine) | 0.241 |
| Nicergoline | 0.24329 |
| Tolnaftate | 0.24408 |
| Diphenylpyraline hydrochloride | 0.24596 |
| Iopromide | 0.24811 |
| Nifurtimox | 0.24846 |
| Piretanide | 0.25211 |
| Imidurea | 0.25671 |
| Calciferol | 0.25816 |
| Piromidic acid | 0.26041 |
| Phenylpropanolamine hydrochloride | 0.26251 |
| Gentamicine sulfate | 0.26288 |
| Myosmine | 0.26499 |
| Phenindione | 0.26543 |
| Trichlorfon | 0.2655 |
| Pancuronium bromide | 0.27081 |
| Griseofulvin | 0.27278 |
| Isradipine | 0.27371 |
| Althiazide | 0.28156 |
| Fenspiride hydrochloride | 0.28266 |
| Glutethimide, para-amino | 0.28575 |
| Carbamazepine | 0.28917 |
| Butamben | 0.29028 |
| Merbromin | 0.29325 |
| Sulfanilamide | 0.29595 |
| Isoxsuprine hydrochloride | 0.30138 |
| Carbarsone | 0.30387 |
| Harmine hydrochloride | 0.30855 |
| Glibenclamide | 0.31123 |
| Condelphine | 0.31433 |
| Pheniramine maleate | 0.31528 |
| Pinacidil | 0.31625 |
| Cephalosporanic acid, 7-amino | 0.32239 |
| Arcaine sulfate | 0.32368 |
| Phentolamine hydrochloride | 0.32447 |
| Tolazoline hydrochloride | 0.32559 |
| Amodiaquin dihydrochloride dihydrate | 0.33145 |
| Capsaicin | 0.33827 |
| Amidopyrine | 0.34699 |
| Syrosingopine | 0.35193 |
| Flavoxate hydrochloride | 0.35347 |
| Alcuronium chloride | 0.35398 |
| Tremorine dihydrochloride | 0.35834 |
| Acetohexamide | 0.35837 |
| Ascorbic acid | 0.35986 |
| Nitrofurantoin | 0.36312 |
| (S)-propranolol hydrochloride | 0.36801 |
| Ritodrine hydrochloride | 0.37869 |
| Fluocinonide | 0.38463 |
| Harmalol hydrochloride dihydrate | 0.38884 |
| Sulfadimethoxine | 0.40771 |
| Sulmazole | 0.40971 |
| Betulinic acid | 0.41189 |
| Trimethylcolchicinic acid | 0.41268 |
| Clozapine | 0.4154 |
| Acacetin | 0.4211 |
| Methoxamine hydrochloride | 0.42389 |
| Dipyridamole | 0.42819 |
| Minaprine dihydrochloride | 0.42897 |
| Fluphenazine dihydrochloride | 0.4317 |
| Benoxinate hydrochloride | 0.43982 |
| Verapamyl hydrochloride | 0.44356 |
| Salmeterol | 0.45025 |
| Edrophonium chloride | 0.4533 |
| Alfuzosin hydrochloride | 0.45337 |
| Acebutolol hydrochloride | 0.45776 |
| Chlorphensin carbamate | 0.45833 |
| Timolol maleate salt | 0.45917 |
| Dimethisoquin hydrochloride | 0.46311 |
| Cholecalciferol | 0.47012 |
| Isoquinoline, 6,7-dimethoxy-1-methyl-1,2,3,4-tetrahydro, hydrochloride | 0.47558 |
| Bisacodyl | 0.47699 |
| Cefoperazone dihydrate | 0.48465 |
| Meclofenoxate hydrochloride | 0.49445 |
| Mebhydroline 1,5-naphtalenedisulfonate | 0.49991 |
| Phenacetin | 0.49998 |
| Pyrithyldione | 0.50424 |

TABLE 1-continued

Rank order of compounds according to their z-score

| Compound Name | Z-score |
|---|---|
| Methyldopate hydrochloride | 0.5054 |
| Oleandomycin phosphate | 0.50691 |
| Furosemide | 0.50742 |
| Tropicamide | 0.50832 |
| Isosorbide dinitrate | 0.50835 |
| Racecadotril | 0.51604 |
| Pramoxine hydrochloride | 0.51947 |
| Antipyrine, 4-hydroxy | 0.51999 |
| Amphotericin B | 0.5223 |
| Flucloxacillin sodium | 0.52413 |
| Sulfapyridine | 0.52561 |
| Trifluoperazine dihydrochloride | 0.5386 |
| 6-Hydroxytropinone | 0.54003 |
| Lisinopril | 0.54031 |
| Metergoline | 0.54738 |
| Midecamycin | 0.55145 |
| Carisoprodol | 0.55907 |
| Altretamine | 0.5601 |
| Ketotifen fumarate | 0.56811 |
| Sulfaquinoxaline sodium salt | 0.579 |
| Meropenem | 0.58062 |
| Diazoxide | 0.59695 |
| Scopoletin | 0.60268 |
| Tocainide hydrochloride | 0.60385 |
| Diphemanil methylsulfate | 0.6045 |
| Vitamin K2 | 0.61285 |
| Isometheptene mucate | 0.61974 |
| Atovaquone | 0.62901 |
| Metampicillin sodium salt | 0.63804 |
| Dropropizine (R,S) | 0.63963 |
| Cotinine (−) | 0.64395 |
| Loracarbef | 0.64573 |
| Deoxycorticosterone | 0.65231 |
| Nafronyl oxalate | 0.65457 |
| Riluzole hydrochloride | 0.65742 |
| Lumicolchicine gamma | 0.65958 |
| Prazosin hydrochloride | 0.65967 |
| Pentylenetetrazole | 0.66528 |
| Homatropine hydrobromide (R,S) | 0.66534 |
| (±)-Nipecotic acid | 0.66549 |
| Norfloxacin | 0.66664 |
| Phenelzine sulfate | 0.66718 |
| Etanidazole | 0.66812 |
| Letrozole | 0.66925 |
| Strophanthidin | 0.67316 |
| Bufexamac | 0.67799 |
| Amitryptiline hydrochloride | 0.67811 |
| Nialamide | 0.67945 |
| Carcinine | 0.68382 |
| Diflorasone Diacetate | 0.68417 |
| Hexylcaine hydrochloride | 0.68701 |
| Famprofazone | 0.69114 |
| Methimazole | 0.69343 |
| Chicago sky blue 6B | 0.69581 |
| Lincomycin hydrochloride | 0.69604 |
| Theophylline monohydrate | 0.70008 |
| Metronidazole | 0.71596 |
| Bupropion hydrochloride | 0.71934 |
| Piroxicam | 0.72535 |
| Carbachol | 0.73838 |
| Testosterone propionate | 0.74885 |
| Probenecid | 0.75398 |
| Aspartic acid, N-acetyl (R,S) | 0.75587 |
| Dinoprost trometamol | 0.76121 |
| Fillalbin | 0.76212 |
| Ofloxacin | 0.76233 |
| Cloperastine hydrochloride | 0.76609 |
| Metformin hydrochloride | 0.76638 |
| Xylometazoline hydrochloride | 0.76862 |
| (S)-(−)-Atenolol | 0.77869 |
| Ornidazole | 0.78241 |
| Aconitine | 0.79071 |
| Aminocaproic acid | 0.80001 |
| Cinoxacin | 0.80088 |
| Adiphenine hydrochloride | 0.80097 |
| Guanethidine sulfate | 0.80139 |
| Lithocholic acid | 0.80216 |
| Piracetam | 0.80376 |
| Gibberellic acid | 0.80894 |
| Cefuroxime sodium salt | 0.81772 |
| Chlorzoxazone | 0.82522 |
| Allantoin | 0.82559 |
| Chloroquine diphosphate | 0.83011 |
| Amprolium hydrochloride | 0.83287 |
| Articaine hydrochloride | 0.83604 |
| Ifenprodil tartrate | 0.83989 |
| Mafenide hydrochloride | 0.84681 |
| Cephalothin sodium salt | 0.85664 |
| Gallamine triethiodide | 0.86436 |
| Salsolinol hydrobromide | 0.87725 |
| Acetazolamide | 0.87732 |
| Zomepirac sodium salt | 0.87942 |
| Mephenytoin | 0.88643 |
| Noscapine | 0.89477 |
| Tubocurarine chloride pentahydrate (+) | 0.89614 |
| Conessine | 0.89622 |
| Eserine sulfate, physostigmine sulfate | 0.89896 |
| Mimosine | 0.90752 |
| Pentetic acid | 0.90771 |
| Eucatropine hydrochloride | 0.91331 |
| Dihydroergocristine mesylate | 0.91569 |
| Hecogenin | 0.92076 |
| Alprenolol hydrochloride | 0.92386 |
| Epicatechin-(−) | 0.92513 |
| Proparacaine hydrochloride | 0.93675 |
| Alclometasone dipropionate | 0.93751 |
| Ivermectin | 0.94188 |
| Isoniazid | 0.94728 |
| Bromopride | 0.94863 |
| Tyloxapol | 0.95711 |
| Trimetazidine dihydrochloride | 0.96543 |
| Spaglumic acid | 0.96658 |
| Scopolamine hydrochloride | 0.96721 |
| (+,−)-Octopamine hydrochloride | 0.97366 |
| (R)-(+)-Atenolol | 0.9856 |
| Fusidic acid sodium salt | 0.99728 |
| Scopolamin-N-oxide hydrobromide | 0.99975 |
| Morantel tartrate | 1.00459 |
| Saquinavir mesylate | 1.02698 |
| Cytisine (−) | 1.04863 |
| Sulfaguanidine | 1.05018 |
| Mexiletine hydrochloride | 1.05417 |
| Trimethobenzamide hydrochloride | 1.06005 |
| Dipyrone | 1.06107 |
| Netilmicin sulfate | 1.06215 |
| Finasteride | 1.06736 |
| Ethosuximide | 1.07586 |
| Pregnenolone | 1.07634 |
| Levocabastine hydrochloride | 1.07813 |
| Rescinnamin | 1.09684 |
| Quinic acid | 1.0976 |
| Clomiphene citrate (Z,E) | 1.10749 |
| Iopamidol | 1.10767 |
| Muramic acid, N-acetyl | 1.12835 |
| Erythromycin | 1.13118 |
| Sulfachloropyridazine | 1.13444 |
| Succinylsulfathiazole | 1.13893 |
| Benzocaine | 1.14853 |
| Androsterone | 1.15571 |
| Cefepime hydrochloride | 1.17243 |
| Hydrochlorothiazide | 1.18029 |
| Atracurium besylate | 1.18219 |
| Atropine sulfate monohydrate | 1.18251 |
| Oxytetracycline dihydrate | 1.18459 |
| Ramipril | 1.18844 |
| Methoxy-6-harmalan | 1.20104 |
| Hyoscyamine (L) | 1.20354 |
| Clocortolone pivalate | 1.21739 |
| Dihydroergotoxine mesylate | 1.21744 |
| Ketoconazole | 1.22425 |
| Hydroquinine hydrobromide hydrate | 1.2243 |
| Meclozine dihydrochloride | 1.22725 |

TABLE 1-continued

Rank order of compounds according to their z-score

| Compound Name | Z-score |
|---|---|
| Thiorphan | 1.24462 |
| Cyclopentolate hydrochloride | 1.25184 |
| Dihydrostreptomycin sulfate | 1.25288 |
| Folic acid | 1.25318 |
| Ketanserin tartrate hydrate | 1.25564 |
| Leflunomide | 1.25767 |
| Trihexyphenidyl-D,L Hydrochloride | 1.25802 |
| Pepstatin A | 1.26143 |
| Nifuroxazide | 1.27857 |
| Pralidoxime chloride | 1.281 |
| Tiletamine hydrochloride | 1.2858 |
| Diphenhydramine hydrochloride | 1.30809 |
| (−)-Quinpirole hydrochloride | 1.31073 |
| Chloramphenicol | 1.31761 |
| Naringenine | 1.33643 |
| Felodipine | 1.33682 |
| Trioxsalen | 1.35921 |
| Megestrol acetate | 1.36176 |
| Dipivefrin hydrochloride | 1.36276 |
| Pyridoxine hydrochloride | 1.36599 |
| Neostigmine bromide | 1.38596 |
| Betaxolol hydrochloride | 1.39325 |
| Hexetidine | 1.39587 |
| Norgestrel-(−)-D | 1.41243 |
| Streptomycin sulfate | 1.41669 |
| Lidoflazine | 1.41971 |
| Oxantel pamoate | 1.42185 |
| Sulfamethazine sodium salt | 1.43137 |
| Niridazole | 1.44644 |
| Sulindac | 1.45062 |
| Nicardipine hydrochloride | 1.45096 |
| Imipramine hydrochloride | 1.45873 |
| Halofantrine hydrochloride | 1.45911 |
| Nifedipine | 1.51575 |
| Cefixime | 1.52068 |
| Rifabutin | 1.52087 |
| Ronidazole | 1.5256 |
| Amrinone | 1.53481 |
| Dirithromycin | 1.53969 |
| Azaperone | 1.54327 |
| Methotrimeprazine maleat salt | 1.54806 |
| Isoflupredone acetate | 1.54992 |
| Nomegestrol acetate | 1.55165 |
| Tolazamide | 1.55441 |
| Betahistine mesylate | 1.55566 |
| Thiamine hydrochloride | 1.57589 |
| Carbetapentane citrate | 1.58129 |
| Dorzolamide hydrochloride | 1.58737 |
| Piperine | 1.58811 |
| Gramine | 1.61758 |
| Probucol | 1.62604 |
| Etodolac | 1.6287 |
| Viomycin sulfate | 1.64015 |
| Procarbazine hydrochloride | 1.67535 |
| Tobramycin | 1.69428 |
| Molsidomine | 1.76131 |
| Demeclocycline hydrochloride | 1.78735 |
| Prochlorperazine dimaleate | 1.82024 |
| Brompheniramine maleate | 1.88454 |
| Metrizamide | 1.8943 |
| Protoveratrine A | 1.89499 |
| Bretylium tosylate | 1.9055 |
| Isocarboxazid | 1.91031 |
| Ceforanide | 1.92883 |
| Methoxy-8-psoralen | 1.94157 |
| Amiloride hydrochloride dihydrate | 1.95465 |
| Sulfabenzamide | 1.95989 |
| Dicumarol | 1.96616 |
| Pridinol methanesulfonate salt | 1.96964 |
| Propranolol hydrochloride | 2.04985 |
| Clobetasol propionate | 2.1955 |
| (R)-Naproxen sodium salt | 2.24257 |
| Hesperidin | 2.25367 |
| Molindone hydrochloride | 2.26252 |
| Terbutaline hemisulfate | 2.27824 |
| Selegiline hydrochloride | 2.27886 |
| Bendroflumethiazide | 2.29669 |
| Clofibric acid | 2.29712 |
| Methacycline hydrochloride | 2.30871 |
| Zalcitabine | 2.32288 |
| Progesterone | 2.34418 |
| Doxycycline hydrochloride | 2.35563 |
| Cyclacillin | 2.40237 |
| Kanamycin A sulfate | 2.43561 |
| Amikacin hydrate | 2.44368 |
| Domperidone maleate | 2.55153 |
| Mecamylamine hydrochloride | 2.56274 |
| Cefotetan | 2.58364 |
| Naringin hydrate | 2.67993 |
| Thonzonium bromide | 2.814 |
| Crotamiton | 2.88584 |
| Hemicholinium bromide | 2.90974 |
| Azaguanine-8 | 2.94804 |
| Pyrimethamine | 2.95897 |
| Strophantine octahydrate | 3.18827 |
| (d,l)-Tetrahydroberberine | 3.2577 |
| Propidium iodide | 4.01365 |
| (−)-Isoproterenol hydrochloride | 4.26697 |
| Artemisinin | 4.80061 |
| Primaquine diphosphate | 5.50982 |
| Minocycline hydrochloride | 5.77623 |
| Quinidine hydrochloride monohydrate | 6.79757 |
| Palmatine chloride | 6.90475 |
| Lovastatin | 6.93472 |
| Coralyne chloride hydrate | 7.27498 |
| Methotrexate | 7.69712 |
| Benzethonium chloride | 8.10467 |
| Meclocycline sulfosalicylate | 8.32605 |
| Hydralazine hydrochloride | 9.34227 |
| Papaverine hydrochloride | 9.54198 |
| Lasalocid sodium salt | 9.89818 |
| Fluvastatin sodium salt | 9.99343 |
| Thiocolchicoside | 11.5611 |
| Resveratrol | 11.669 |
| Methyl benzethonium chloride | 12.6356 |
| Berberine chloride | 12.68 |
| Deferoxamine mesylate | 12.8786 |
| Clofilium tosylate | 13.6063 |
| Thiostrepton | 13.9158 |
| Pentamidine isethionate | 14.9126 |
| Simvastatin | 15.173 |
| Disulfiram | 15.5036 |
| Amethopterin (R,S) | 15.6786 |
| Proguanil hydrochloride | 16.0329 |
| Azacytidine-5 | 16.1728 |
| Fenbendazole | 16.3822 |
| Piperlongumine | 16.6479 |
| Thiamphenicol | 16.8903 |
| Chelidonine (+) | 16.9912 |
| Azathioprine | 17.2224 |
| Ethaverine hydrochloride | 17.3528 |
| Nocodazole | 18.0445 |
| Monensin sodium salt | 18.1768 |
| Thioguanosine | 18.3737 |
| Cantharidin | 18.9862 |
| Budesonide | 19.1411 |
| Methiazole | 19.8245 |
| Scoulerine | 19.9884 |
| Hycanthone | 20.1467 |
| Trifluridine | 21.7513 |
| Lycorine hydrochloride | 21.7885 |
| Suloctidil | 21.8147 |
| Camptothecine (S,+) | 21.8871 |
| Chlorhexidine | 24.4911 |
| Niclosamide | 25.4633 |
| Cephaeline dihydrochloride heptahydrate | 26.5614 |
| Myricetin | 27.33 |
| Daunorubicin hydrochloride | 28.7571 |
| Anisomycin | 30.3787 |
| Antimycin A | 30.555 |
| Sanguinarine | 31.0936 |
| Florfenicol | 31.4352 |

TABLE 1-continued

Rank order of compounds according to their z-score

| Compound Name | Z-score |
|---|---|
| Doxorubicin hydrochloride | 32.6438 |
| Emetine dihydrochloride | 32.7653 |
| Colchicine | 35.6417 |
| Mycophenolic acid | 36.1922 |
| Ellipticine | 36.711 |
| Parbendazole | 39.1106 |
| Etoposide | 39.4033 |
| Ciclopirox ethanolamine | 40.334 |
| Albendazole | 41.6509 |
| Dequalinium dichloride | 42.6725 |
| Alexidine dihydrochloride | 43.2376 |
| Mitoxantrone dihydrochloride | 45.2169 |
| Podophyllotoxin | 46.4771 |
| Pyrvinium pamoate | 47.9867 |
| Paclitaxel | 48.9183 |
| Mebendazole | 49.935 |
| Cycloheximide | 56.1385 |
| Puromycin dihydrochloride | 74.4112 |

TABLE 2

List of Glycolytic Switch Compounds

| Rank* | Compound Name |
|---|---|
| 1 | Fendiline hydrochloride |
| 2 | Vinpocetine |
| 3 | Mefloquine hydrochloride |
| 4 | Perhexiline maleate |
| 8 | Gossypol |
| 23 | Butylparaben |
| 37 | Clotrimazole |
| 40 | Fruspirilen |
| 44 | Cinnarizine |
| 52 | Ebselen |
| 61 | Ethynodiol diacetate |
| 118 | Thiethylperazine malate |
| 130 | Tamoxifen citrate |
| 133 | Chrysene-1,4-quinone |
| 135 | Biperiden hydrochloride |
| 197 | Clemastine fumarate |
| 208 | GBR 12909 dihydrochloride |
| 223 | Chlorprothixene hydrochloride |
| 230 | Clomipramine hydrochloride |
| 320 | Homosalate |
| 330 | Pimozide |
| 372 | Sulconazole nitrate |
| 383 | Naftifine hydrochloride |
| 449 | Piperidolate hydrochloride |
| 464 | Sertaconazole nitrate |
| 517 | Menadione |
| 524 | Phenformin hydrochloride |
| 579 | Cyclobenzaprine hydrochloride |
| 644 | Triflupromazine hydrochloride |
| 658 | Methiothepin maleate |
| 702 | Phenoxybenzamine hydrochloride |
| 720 | (1-[(4-Chlorophenyl)phenyl-methyl]-4-methylpiperazine) |
| 743 | Merbromin |
| 764 | Ascorbic acid |
| 791 | Bisacodyl |
| 814 | Altretamine |
| 857 | Testosterone propionate |
| 863 | Cloperastine hydrochloride |
| 924 | Pregnenolone |
| 928 | Clomiphene citrate (Z, E) |
| 957 | Nifuroxazide |

*Rank in normalized ORO score from screen

SEQUENCES

Homo sapiens adipose triglyceride lipase (ATGL) mRNA, complete cds.
ACCESSION AY894804
VERSION AY894804.1 GI:58759050

(SEQ ID NO; 1)

```
  1 atgtttcccc gcgagaagac gtggaacatc tcgttcgcgg gctgcggctt cctcggcgtc
 61 tactacgtcg gcgtggcctc ctgcctccgc gagcacgcgc ccttcctggt ggccaacgcc
121 acgcacatct acggcgcctc ggccggggcg ctcacggcca cggcgctggt caccggggtc
181 tgcctgggtg aggctggtgc caagttcatt gaggtatcta aagaggcccg gaagcggttc
241 ctgggccccc tgcacccctc cttcaacctg gtaaagatca tccgcagttt cctgctgaag
301 gtcctgcctg ctgatagcca tgagcatgcc agtgggcgcc tgggcatctc cctgacccgc
361 gtgtcagacg gcgagaatgt cattatatcc cacttcaact ccaaggacga gctcatccag
421 gccaatgtct gcagcggttt catcccgtg tactgtgggc tcatccctcc ctccctccag
481 ggggtgcgct acgtggatgg tggcatttca gacaacctgc cactctatga gcttaagaac
541 accatcacag tgtcccccctt ctcgggcgag agtgacatct gtccgcagga cagctccacc
601 aacatccacg agctgcgggt caccaacacc agcatccagt tcaacctgcg caacctctac
661 cgcctctcca aggccctctt cccgccggag ccctggtgc tgcgagagat gtgcaagcag
721 ggataccggg atggcctgcg ctttctgcag cggaacggcc tcctgaaccg gcccaacccc
781 ttgctggcgt tgccccccgc ccgccccac ggcccagagg acaaggacca ggcagtggag
841 agcgcccaag cggaggatta ctcgcagctg cggggagaag atcacgtcct ggagcacctg
901 cccgccggc tcaatgaggc cctgctggag gcctgcgtgg agcccacgga cctgctgacc
```

-continued

```
 961 accctctcca acatgctgcc tgtgcgtctg gccacggcca tgatggtgcc ctacacgctg 1021 ccgctggaga gcgctctgtc cttcaccatc tgcttgctgg agtggctgcc cgacgttccc 1081 gaggacatcc ggtggatgaa ggagcagacg ggcagcatct gccagtacct ggtgatgcgc 1141 gccaagagga agctgggcag gcacctgccc tccaggctgc cggagcaggt ggagctgcgc 1201 cgcgtccagt cgctgccgtc cgtgccgctg tcctgcgccg cctacagaga ggcaccgccc 1261 ggctggatgc gcaacaacct ctcgctgggg gacgcgctgg ccaagtggga ggagtgccag 1321 cgccagctgc tgctcggcct cttctgcacc aacgtggcct tcccgcccga agctctgcgc 1381 atgcgcgcac ccgccgaccc ggctcccgcc ccgcggacc cagcatcccc gcagcaccag 1441 ctggccgggc ctgcccccctt gctgagcacc cctgctcccg aggcccggcc cgtgatcggg 1501 gccctggggc tgtga
```

I claim:

1. A method for reducing intracellular lipid accumulation in a cell comprising contacting the cell in vitro or in vivo with an effective amount of a compound selected from Table 3, wherein the effective amount of the compound shifts cellular energy metabolism from fatty acid oxidation to glycolysis, thereby reducing intracellular lipid accumulation within the cell, wherein the cell has reduced Adipose Triglyceride Lipase (ATGL) function due to a loss of function mutation in the gene PNPLA2.

2. The method of claim 1, wherein the cell is selected from the group consisting of: a skeletal muscle cell, a heart muscle cell, a smooth muscle cell, a neuronal cell, a leukocyte cell, a bone marrow cell, an epithelial cell, and an endothelial cell.

3. The method of claim 1, wherein the contact is in vivo.

4. The method of claim 1, wherein the compound further comprises a pharmaceutically acceptable carrier.

5. The method of claim 3, wherein the in vivo contact is in a human subject.

6. The method of claim 3, wherein the in vivo contact comprises administering the compound using an administration route selected from the group consisting of: oral, subcutaneous, intravenous, intramuscular, intraperitoneal, intranasal, and topical.

7. The method of claim 5, wherein the human subject has Neutral Lipid Storage Disease associated with myopathy (NLSD-M).

8. The method of claim 1, wherein the compound is Mefloquine hydrochloride.

9. The method of claim 1, wherein the effective amount of the compound ranges from about 0.1 µM to about 20 µM.

* * * * *

SEQUENCE LISTING

<160> NUMBER OF SEQ ID NOS: 44

<210> SEQ ID NO 1
<211> LENGTH: 1515
<212> TYPE: DNA
<213> ORGANISM: Homo sapiens

<400> SEQUENCE: 1

```
atgtttcccc gcgagaagac gtggaacatc tcgttcgcgg gctgcggctt cctcggcgtc    60
tactacgtcg gcgtggcctc ctgcctccgc gagcacgcgc ccttcctggt ggccaacgcc   120
acgcacatct acggcgcctc ggccggggcg ctcacggcca cggcgctggt caccggggtc   180
tgcctgggtg aggctggtgc caagttcatt gaggtatcta agaggcccg gaagcggttc    240 ctgggccccc tgcacccctc cttcaacctg gtaaagatca tccgcagttt cctgctgaag   300
gtcctgcctg ctgatagcca tgagcatgcc agtgggcgcc tgggcatctc cctgaccccg c  360 gtgtcagacg gcgagaatgt cattatatcc cacttcaact ccaaggacga gctcatccag    420
gccaatgtct gcagcggttt catccccgtg tactgtgggc tcatccctcc ctccctccag    480
ggggtgcgct acgtggatgg tggcattttca gacaacctgc cactctatga gcttaagaac   540
accatcacag tgtccccctt ctcgggcgag agtgacatct gtccgcagga cagctccacc    600
aacatccacg agctgcgggt caccaacacc agcatccagt tcaacctgcg caacctctac    660
cgcctctcca aggccctctt cccgccgag ccctggtgc tgcgagagat gtgcaagcag    720
ggataccggg atggcctgcg cttctgcag cggaacggcc tcctgaaccg gcccaacccc    780
ttgctggcgt tgccccccgc ccgccccac ggcccagagg acaaggacca ggcagtggag    840
agcgcccaag cggaggatta ctcgcagctg ccgggagaag atcacgtcct ggagcacctg    900
cccgcccggc tcaatgaggc cctgctggag gcctgcgtgg agcccacgga cctgctgacc    960
accctctcca acatgctgcc tgtgcgtctg gccacggcca tgatggtgcc ctacacgctg   1020
ccgctggaga gcgctctgtc cttcaccatc tgcttgctgg agtggctgcc cgacgttccc   1080
gaggacatcc ggtggatgaa ggagcagacg ggcagcatct gccagtacct ggtgatgcgc   1140
gccaagagga agctgggcag gcacctgccc tccaggctgc cggagcaggt ggagctgcgc   1200
cgcgtccagt cgctgccgtc cgtgccgctg tcctgcgccg cctacagaga ggcaccgccc   1260
ggctggatgc gcaacaacct ctcgctgggg gacgcgctgg ccaagtggga ggagtgccag   1320
cgccagctgc tgctcggcct cttctgcacc aacgtggcct tcccgcccga agctctgcgc   1380
```

```
atgcgcgcac cgccgaccc ggctcccgcc ccgcggacc cagcatcccc gcagcaccag    1440
ctggccgggc ctgccccctt gctgagcacc cctgctcccg aggcccggcc cgtgatcggg    1500
gccctggggc tgtga                                                    1515

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ctcccgagga gtcccaggac at                                             22

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gatggtggtc tggctgaaca cct                                            23

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gcggagtgga aactttttgtc c                                             21

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cgggaagcgt gtacttatcc tt                                             22

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
caagggtctg ctactgagat gctctg                                         26

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 7
ttttgtttgg gactggtaga agaatcag                                          28

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cagaggaggc aacgtagaa g                                                  21

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ctccatcggg gatcttgggt                                                   20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gacaaagccg agacggatgg                                                   20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ctgtcgcttg cacttgtagc                                                   20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ctgtcatctc actatgggca                                                   20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 13
ccaagtccga gcaggaattt                                          20

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ccctacgcca acatgaactc g                                        21

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gttctgccgg tagaaaggga                                          20

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
aactctggcg atgggtgttt a                                        21

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
acactgatgt ctttccactc ca                                       22

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ccctgaagtc gaggagctg                                           19

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
```
ctgctgcacc tctaagcga                                           19

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
actggcctac tacagagaag c                                        21

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gtagagtgcc gtcttgccat a                                        21

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ctgccagtcc gaaaatggaa c                                        21

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cttcatccac cggggctatc                                          20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gccaagaagc ggatagaagg                                          20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25

```
ctgtggttca gggctcagtc                                               20
```

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26

```
gctggattac atggtcccaa g                                             21
```

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27

```
ggcacttcag aaatcggagg g                                             21
```

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28

```
aggtcggtgt gaacggattt g                                             21
```

<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29

```
tgtagaccat gtagttgagg tca                                           23
```

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30

```
caacgccact cacatctacg g                                             21
```

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31

```
ggacacctca ataatgttgg cac                                           23
```

```
<210> SEQ ID NO 32
<211> LENGTH: 9
<212> TYPE: PRT
<213> ORGANISM: Human immunodeficiency virus 1

<400> SEQUENCE: 32

Arg Lys Lys Arg Arg Gln Arg Arg Arg
1               5

<210> SEQ ID NO 33
<211> LENGTH: 13
<212> TYPE: PRT
<213> ORGANISM: Human immunodeficiency virus 1

<400> SEQUENCE: 33

Gly Arg Lys Lys Arg Arg Gln Arg Arg Arg Thr Pro Gln
1               5                   10

<210> SEQ ID NO 34
<211> LENGTH: 11
<212> TYPE: PRT
<213> ORGANISM: Human immunodeficiency virus 1

<400> SEQUENCE: 34

Tyr Gly Arg Lys Lys Arg Arg Gln Arg Arg
1               5                   10

<210> SEQ ID NO 35
<211> LENGTH: 26
<212> TYPE: PRT
<213> ORGANISM: Homo sapiens

<400> SEQUENCE: 35

Ala Ala Val Ala Leu Leu Pro Ala Val Leu Leu Ala Leu Leu Ala Pro
1               5                   10                  15

Val Gln Arg Lys Arg Gln Lys Leu Met Pro
            20                  25

<210> SEQ ID NO 36
<211> LENGTH: 17
<212> TYPE: PRT
<213> ORGANISM: Caiman crocodylus

<400> SEQUENCE: 36

Met Gly Leu Gly Leu His Leu Leu Val Leu Ala Ala Ala Leu Gln Gly
1               5                   10                  15

Ala

<210> SEQ ID NO 37
<211> LENGTH: 23
<212> TYPE: PRT
<213> ORGANISM: Human immunodeficiency virus 1

<400> SEQUENCE: 37

Gly Ala Leu Phe Leu Gly Phe Leu Gly Ala Ala Gly Ser Thr Met Gly
1               5                   10                  15

Ala Pro Lys Ser Lys Arg Lys
            20

<210> SEQ ID NO 38
<211> LENGTH: 16
<212> TYPE: PRT
```

```
<213> ORGANISM: Drosophila sp.

<400> SEQUENCE: 38

Arg Gln Ile Lys Ile Trp Phe Gln Asn Arg Arg Met Lys Trp Lys Lys
1               5                   10                  15

<210> SEQ ID NO 39
<211> LENGTH: 24
<212> TYPE: PRT
<213> ORGANISM: Influenza virus

<400> SEQUENCE: 39

Gly Leu Phe Glu Ala Ile Ala Gly Phe Ile Glu Asn Gly Trp Glu Gly
1               5                   10                  15

Met Ile Asp Gly Gly Gly Tyr Cys
            20

<210> SEQ ID NO 40
<211> LENGTH: 27
<212> TYPE: PRT
<213> ORGANISM: Unknown
<220> FEATURE:
<223> OTHER INFORMATION: Description of Unknown: Transportan A peptide

<400> SEQUENCE: 40

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 41
<211> LENGTH: 9
<212> TYPE: PRT
<213> ORGANISM: Unknown
<220> FEATURE:
<223> OTHER INFORMATION: Description of Unknown: Pre-S-peptide
<220> FEATURE:
<221> NAME/KEY: MOD_RES
<222> LOCATION: (1)..(1)
<223> OTHER INFORMATION: May or may not be present

<400> SEQUENCE: 41

Ser Asp His Gln Leu Asn Pro Ala Phe
1               5

<210> SEQ ID NO 42
<211> LENGTH: 9
<212> TYPE: PRT
<213> ORGANISM: Unknown
<220> FEATURE:
<223> OTHER INFORMATION: Description of Unknown: Somatostatin
      (tyr-3-octreotate) peptide
<220> FEATURE:
<221> NAME/KEY: MOD_RES
<222> LOCATION: (1)..(1)
<223> OTHER INFORMATION: May or may not be present
<220> FEATURE:
<221> NAME/KEY: MOD_RES
<222> LOCATION: (2)..(2)
<223> OTHER INFORMATION: May be L-Phe or D-Phe
<220> FEATURE:
<221> NAME/KEY: MOD_RES
<222> LOCATION: (5)..(5)
<223> OTHER INFORMATION: May be L-Trp or D-Trp

<400> SEQUENCE: 42

Ser Phe Cys Tyr Trp Lys Thr Cys Thr
1               5
```

```
<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ala Phe Asp Asn Val Gly Tyr Glu
1               5

<210> SEQ ID NO 44
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(8)
<223> OTHER INFORMATION: This peptide may be 1-8 residues in length

<400> SEQUENCE: 44

Gly Gly Gly Gly Gly Gly Gly Gly
1               5
```